United States Patent
Koltermann et al.

(10) Patent No.: US 8,859,247 B2
(45) Date of Patent: Oct. 14, 2014

(54) PROCESS FOR CELL-FREE PRODUCTION OF CHEMICALS

(75) Inventors: Andre Koltermann, Icking (DE); Ulrich Kettling, Munich (DE); Volker Sieber, Nandlstadt (DE)

(73) Assignee: Süd-Chemie IP GmbH & Co. KG, Munich (DE)

( * ) Notice: Subject to any disclaimer, the term of this patent is extended or adjusted under 35 U.S.C. 154(b) by 0 days.

(21) Appl. No.: 13/143,019

(22) PCT Filed: Dec. 28, 2009

(86) PCT No.: PCT/EP2009/067954
§ 371 (c)(1), (2), (4) Date: Sep. 8, 2011

(87) PCT Pub. No.: WO2010/076305
PCT Pub. Date: Jul. 8, 2010

(65) Prior Publication Data
US 2011/0312052 A1    Dec. 22, 2011

(30) Foreign Application Priority Data

Dec. 30, 2008    (EP) .................................... 08022558

(51) Int. Cl.
*C12P 7/02* (2006.01)
*C12P 7/06* (2006.01)
*C12P 7/16* (2006.01)

(52) U.S. Cl.
CPC .. *C12P 7/16* (2013.01); *Y02E 50/10* (2013.01); *Y02E 50/17* (2013.01); *C12P 7/06* (2013.01)
USPC ............................. 435/155; 435/160; 435/161

(58) Field of Classification Search
None
See application file for complete search history.

(56) References Cited

PUBLICATIONS

Richter, FW (ed.), *Biotechnology: Research, Technology and Applications* New York 2008, Chapter 6 (Zhang et al. "Biofuels Production by Cell Free Synthetic Enzymatic Technology").
Welch P., et al., "Studies on Cell-Free Metabolism Ethanol Production by a Yeast Glycolytic System Reconstituted from Purified Enzymes" *J. Biotechnol.* 2(5): 257-274 (1985).
Algar EM, et al., "Studies on Cell-Free Metabolism Ethanol Production by Extracts of *Zymomonas mobilis*" *J. Biotechnol.* 2(5):275-288 (1985).
Lamble HJ et al., "Metabolic Pathway Promiscuity in the Archaeon *Sulfolobus solfataricus* Revealed by Studies on Glucose Dehydrogenase and 2-Keto-3-deoxygluconate Aldolase" *J. Biol. Chem.* 278(36): 34066-34072 (2003).
Ezeji et al., "Bioproduction of Butanol from Biomass: From Genes to Bioreactors" *Curr. Op. Biotechnol.* 18(3): 220-227 (2007).
Allain EJ, "Cell-Free Ethanol Production: The Future of Fuel Ethanol?" J. Chem. Technol. Biotechnol. 82(2): 117-120 (2007).

*Primary Examiner* — Nashaat Nashed
(74) *Attorney, Agent, or Firm* — McCarter & English, LLP; Danielle L. Herritt

(57) ABSTRACT

An enzymatic process is described for the production of chemicals from carbon sources. In particular, according to one aspect, a process for the production of a target organic compound from a carbon source by a cell-free enzyme system is disclosed.

15 Claims, 1 Drawing Sheet

Scheme of process
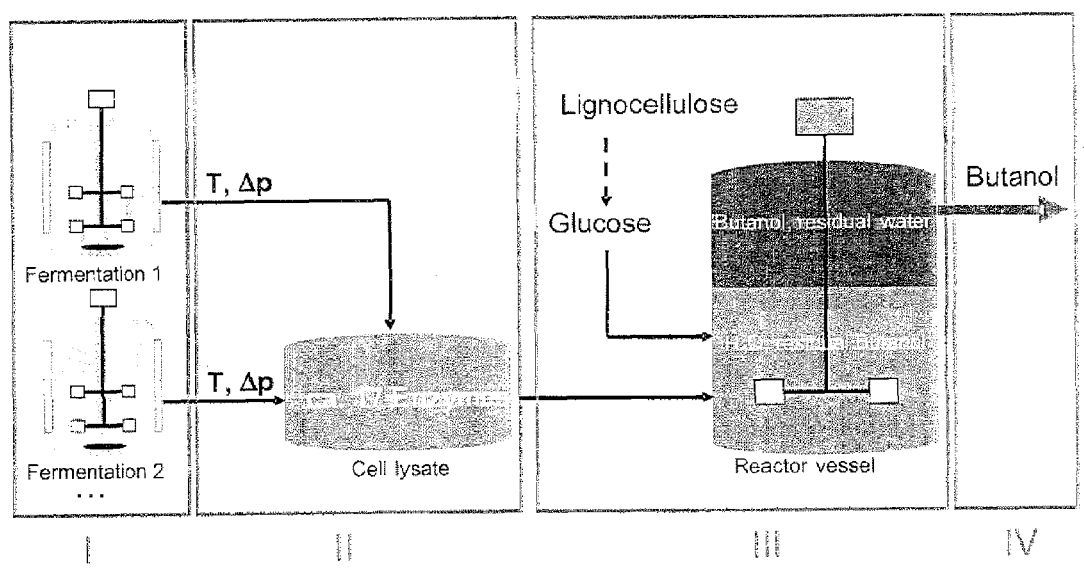

SEQUENCE LISTING

<160> NUMBER OF SEQ ID NOS: 39

<210> SEQ ID NO 1
<211> LENGTH: 392
<212> TYPE: PRT
<213> ORGANISM: Clostridium acetobutylicum

<400> SEQUENCE: 1

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320
```

```
Ala Gln Ser Leu Ala Val Lys Asp Leu Lys Phe Asp Met Asn Lys
            325                 330                 335

Val Asn Val Asn Gly Gly Ala Ile Ala Leu Gly His Pro Ile Gly Ala
        340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gln Gly
        370                 375                 380

Thr Ala Ile Leu Leu Glu Lys Cys
385                 390
```

<210> SEQ ID NO 2
<211> LENGTH: 282
<212> TYPE: PRT
<213> ORGANISM: Clostridium acetobutylicum

<400> SEQUENCE: 2

```
Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280
```

<210> SEQ ID NO 3

-continued

```
<211> LENGTH: 261
<212> TYPE: PRT
<213> ORGANISM: Clostridium acetobutylicum

<400> SEQUENCE: 3
```

| | | | | | | | | | | | | | | |
|---|---|---|---|---|---|---|---|---|---|---|---|---|---|---|
| Met | Glu | Leu | Asn | Asn | Val | Ile | Leu | Glu | Lys | Glu | Gly | Lys | Val | Ala | Val |
| 1 | | | | 5 | | | | | 10 | | | | | 15 | |
| Val | Thr | Ile | Asn | Arg | Pro | Lys | Ala | Leu | Asn | Ala | Leu | Asn | Ser | Asp | Thr |
| | | | 20 | | | | | 25 | | | | | 30 | | |
| Leu | Lys | Glu | Met | Asp | Tyr | Val | Ile | Gly | Glu | Ile | Glu | Asn | Asp | Ser | Glu |
| | | 35 | | | | | 40 | | | | | 45 | | | |
| Val | Leu | Ala | Val | Ile | Leu | Thr | Gly | Ala | Gly | Lys | Ser | Phe | Val | Ala | |
| | 50 | | | | | 55 | | | | | 60 | | | | |
| Gly | Ala | Asp | Ile | Ser | Glu | Met | Lys | Glu | Met | Asn | Thr | Ile | Glu | Gly | Arg |
| 65 | | | | | 70 | | | | | 75 | | | | | 80 |
| Lys | Phe | Gly | Ile | Leu | Gly | Asn | Lys | Val | Phe | Arg | Arg | Leu | Glu | Leu | Leu |
| | | | | 85 | | | | | 90 | | | | | 95 | |
| Glu | Lys | Pro | Val | Ile | Ala | Ala | Val | Asn | Gly | Phe | Ala | Leu | Gly | Gly | Gly |
| | | | 100 | | | | | 105 | | | | | 110 | | |
| Cys | Glu | Ile | Ala | Met | Ser | Cys | Asp | Ile | Arg | Ile | Ala | Ser | Ser | Asn | Ala |
| | | | | 115 | | | | | 120 | | | | | 125 | |
| Arg | Phe | Gly | Gln | Pro | Glu | Val | Gly | Leu | Gly | Ile | Thr | Pro | Gly | Phe | Gly |
| | 130 | | | | | 135 | | | | | 140 | | | | |
| Gly | Thr | Gln | Arg | Leu | Ser | Arg | Leu | Val | Gly | Met | Gly | Met | Ala | Lys | Gln |
| 145 | | | | | 150 | | | | | 155 | | | | | 160 |
| Leu | Ile | Phe | Thr | Ala | Gln | Asn | Ile | Lys | Ala | Asp | Glu | Ala | Leu | Arg | Ile |
| | | | | 165 | | | | | 170 | | | | | 175 | |
| Gly | Leu | Val | Asn | Lys | Val | Val | Glu | Pro | Ser | Glu | Leu | Met | Asn | Thr | Ala |
| | | | 180 | | | | | 185 | | | | | 190 | | |
| Lys | Glu | Ile | Ala | Asn | Lys | Ile | Val | Ser | Asn | Ala | Pro | Val | Ala | Val | Lys |
| | | | | 195 | | | | | 200 | | | | | 205 | |
| Leu | Ser | Lys | Gln | Ala | Ile | Asn | Arg | Gly | Met | Gln | Cys | Asp | Ile | Asp | Thr |
| | 210 | | | | | 215 | | | | | 220 | | | | |
| Ala | Leu | Ala | Phe | Glu | Ser | Glu | Ala | Phe | Gly | Glu | Cys | Phe | Ser | Thr | Glu |
| 225 | | | | | 230 | | | | | 235 | | | | | 240 |
| Asp | Gln | Lys | Asp | Ala | Met | Thr | Ala | Phe | Ile | Glu | Lys | Arg | Lys | Ile | Glu |
| | | | | 245 | | | | | 250 | | | | | 255 | |
| Gly | Phe | Lys | Asn | Arg | | | | | | | | | | | |
| | | | 260 | | | | | | | | | | | | |

```
<210> SEQ ID NO 4
<211> LENGTH: 379
<212> TYPE: PRT
<213> ORGANISM: Clostridium acetobutylicum

<400> SEQUENCE: 4
```

| | | | | | | | | | | | | | | | |
|---|---|---|---|---|---|---|---|---|---|---|---|---|---|---|---|
| Met | Asp | Phe | Asn | Leu | Thr | Arg | Glu | Gln | Glu | Leu | Val | Arg | Gln | Met | Val |
| 1 | | | | 5 | | | | | 10 | | | | | 15 | |
| Arg | Glu | Phe | Ala | Glu | Asn | Glu | Val | Lys | Pro | Ile | Ala | Ala | Glu | Ile | Asp |
| | | | 20 | | | | | 25 | | | | | 30 | | |
| Glu | Thr | Glu | Arg | Phe | Pro | Met | Glu | Asn | Val | Lys | Lys | Met | Gly | Gln | Tyr |
| | | 35 | | | | | 40 | | | | | 45 | | | |
| Gly | Met | Met | Gly | Ile | Pro | Phe | Ser | Lys | Glu | Tyr | Gly | Gly | Ala | Gly | Gly |
| | 50 | | | | | 55 | | | | | 60 | | | | |
| Asp | Val | Leu | Ser | Tyr | Ile | Ile | Ala | Val | Glu | Glu | Leu | Ser | Lys | Val | Cys |
| 65 | | | | | 70 | | | | | 75 | | | | | 80 |

Gly Thr Thr Gly Val Ile Leu Ser Ala His Thr Ser Leu Cys Ala Ser
                85                  90                  95

Leu Ile Asn Glu His Gly Thr Glu Glu Gln Lys Gln Lys Tyr Leu Val
            100                 105                 110

Pro Leu Ala Lys Gly Glu Lys Ile Gly Ala Tyr Gly Leu Thr Glu Pro
        115                 120                 125

Asn Ala Gly Thr Asp Ser Gly Ala Gln Gln Thr Val Ala Val Leu Glu
    130                 135                 140

Gly Asp His Tyr Val Ile Asn Gly Ser Lys Ile Phe Ile Thr Asn Gly
145                 150                 155                 160

Gly Val Ala Asp Thr Phe Val Ile Phe Ala Met Thr Asp Arg Thr Lys
                165                 170                 175

Gly Thr Lys Gly Ile Ser Ala Phe Ile Ile Glu Lys Gly Phe Lys Gly
            180                 185                 190

Phe Ser Ile Gly Lys Val Glu Gln Lys Leu Gly Ile Arg Ala Ser Ser
        195                 200                 205

Thr Thr Glu Leu Val Phe Glu Asp Met Ile Val Pro Val Glu Asn Met
    210                 215                 220

Ile Gly Lys Glu Gly Lys Gly Phe Pro Ile Ala Met Lys Thr Leu Asp
225                 230                 235                 240

Gly Gly Arg Ile Gly Ile Ala Ala Gln Ala Leu Gly Ile Ala Glu Gly
                245                 250                 255

Ala Phe Asn Glu Ala Arg Ala Tyr Met Lys Glu Arg Lys Gln Phe Gly
            260                 265                 270

Arg Ser Leu Asp Lys Phe Gln Gly Leu Ala Trp Met Met Ala Asp Met
        275                 280                 285

Asp Val Ala Ile Glu Ser Ala Arg Tyr Leu Val Tyr Lys Ala Ala Tyr
    290                 295                 300

Leu Lys Gln Ala Gly Leu Pro Tyr Thr Val Asp Ala Ala Arg Ala Lys
305                 310                 315                 320

Leu His Ala Ala Asn Val Ala Met Asp Val Thr Thr Lys Ala Val Gln
                325                 330                 335

Leu Phe Gly Gly Tyr Gly Tyr Thr Lys Asp Tyr Pro Val Glu Arg Met
            340                 345                 350

Met Arg Asp Ala Lys Ile Thr Glu Ile Tyr Glu Gly Thr Ser Glu Val
        355                 360                 365

Gln Lys Leu Val Ile Ser Gly Lys Ile Phe Arg
    370                 375

<210> SEQ ID NO 5
<211> LENGTH: 468
<212> TYPE: PRT
<213> ORGANISM: Clostridium beijerinckii

<400> SEQUENCE: 5

Met Asn Lys Asp Thr Leu Ile Pro Thr Thr Lys Asp Leu Lys Leu Lys
1               5                   10                  15

Thr Asn Val Glu Asn Ile Asn Leu Lys Asn Tyr Lys Asp Asn Ser Ser
            20                  25                  30

Cys Phe Gly Val Phe Glu Asn Val Glu Asn Ala Ile Asn Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Val

```
          65                  70                  75                  80
Leu Ala Thr Met Ile Leu Glu Glu Thr His Met Gly Arg Tyr Glu Asp
                    85                  90                  95
Lys Ile Leu Lys His Glu Leu Val Ala Lys Tyr Thr Pro Gly Thr Glu
                100                 105                 110
Asp Leu Thr Thr Thr Ala Trp Ser Gly Asp Asn Gly Leu Thr Val Val
                115                 120                 125
Glu Met Ser Pro Tyr Gly Val Ile Gly Ala Ile Thr Pro Ser Thr Asn
            130                 135                 140
Pro Thr Glu Thr Val Ile Cys Asn Ser Ile Gly Met Ile Ala Ala Gly
145                 150                 155                 160
Asn Ala Val Val Phe Asn Gly His Pro Gly Ala Lys Lys Cys Val Ala
                    165                 170                 175
Phe Ala Ile Glu Met Ile Asn Lys Ala Ile Ile Ser Cys Gly Gly Pro
                180                 185                 190
Glu Asn Leu Val Thr Thr Ile Lys Asn Pro Thr Met Glu Ser Leu Asp
                195                 200                 205
Ala Ile Ile Lys His Pro Leu Ile Lys Leu Leu Cys Gly Thr Gly Gly
            210                 215                 220
Pro Gly Met Val Lys Thr Leu Leu Asn Ser Gly Lys Lys Ala Ile Gly
225                 230                 235                 240
Ala Gly Ala Gly Asn Pro Pro Val Ile Val Asp Asp Thr Ala Asp Ile
                    245                 250                 255
Glu Lys Ala Gly Lys Ser Ile Ile Glu Gly Cys Ser Phe Asp Asn Asn
                260                 265                 270
Leu Pro Cys Ile Ala Glu Lys Glu Val Phe Val Phe Glu Asn Val Ala
            275                 280                 285
Asp Asp Leu Ile Ser Asn Met Leu Lys Asn Asn Ala Val Ile Ile Asn
            290                 295                 300
Glu Asp Gln Val Ser Lys Leu Ile Asp Leu Val Leu Gln Lys Asn Asn
305                 310                 315                 320
Glu Thr Gln Glu Tyr Phe Ile Asn Lys Lys Trp Val Gly Lys Asp Ala
                    325                 330                 335
Lys Leu Phe Ser Asp Glu Ile Asp Val Glu Ser Pro Ser Asn Ile Lys
                340                 345                 350
Cys Ile Val Cys Glu Val Asn Ala Asn His Pro Phe Val Met Thr Glu
            355                 360                 365
Leu Met Met Pro Ile Leu Pro Ile Val Arg Val Lys Asp Ile Asp Glu
370                 375                 380
Ala Val Lys Tyr Thr Lys Ile Ala Glu Gln Asn Arg Lys His Ser Ala
385                 390                 395                 400
Tyr Ile Tyr Ser Lys Asn Ile Asp Asn Leu Asn Arg Phe Glu Arg Glu
                    405                 410                 415
Ile Asp Thr Thr Ile Phe Val Lys Asn Ala Lys Ser Phe Ala Gly Val
                420                 425                 430
Gly Tyr Glu Ala Glu Gly Phe Thr Thr Phe Thr Ile Ala Gly Ser Thr
            435                 440                 445
Gly Glu Gly Ile Thr Ser Ala Arg Asn Phe Thr Arg Gln Arg Arg Cys
        450                 455                 460

Val Leu Ala Gly
465

<210> SEQ ID NO 6
```

<211> LENGTH: 390
<212> TYPE: PRT
<213> ORGANISM: Clostridium acetobutylicum

<400> SEQUENCE: 6

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
        50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
            85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
            165                 170                 175

Pro Thr Tyr Thr Tyr Thr Val Pro Thr Asn Gln Thr Ala Ala Gly Thr
        180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
            245                 250                 255

Thr Tyr Gly Lys Asp Thr Asn Trp Ser Val His Leu Met Glu His Glu
        260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
            325                 330                 335

Val Asn Val Leu Gly Leu Pro Ser Arg Leu Arg Asp Val Gly Ile Glu
        340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
370                 375                 380

Ile Phe Lys Lys Ser Val
```

<210> SEQ ID NO 7
<211> LENGTH: 259
<212> TYPE: PRT
<213> ORGANISM: Clostridium acetobutylicum

<400> SEQUENCE: 7

Met Asn Ile Val Val Cys Leu Lys Gln Val Pro Asp Thr Ala Glu Val
1               5                   10                  15

Arg Ile Asp Pro Val Lys Gly Thr Leu Ile Arg Glu Gly Val Pro Ser
            20                  25                  30

Ile Ile Asn Pro Asp Asp Lys Asn Ala Leu Glu Glu Ala Leu Val Leu
        35                  40                  45

Lys Asp Asn Tyr Gly Ala His Val Thr Val Ile Ser Met Gly Pro Pro
50                  55                  60

Gln Ala Lys Asn Ala Leu Val Glu Ala Leu Ala Met Gly Ala Asp Glu
65                  70                  75                  80

Ala Val Leu Leu Thr Asp Arg Ala Phe Gly Gly Ala Asp Thr Leu Ala
                85                  90                  95

Thr Ser His Thr Ile Ala Ala Gly Ile Lys Lys Leu Lys Tyr Asp Ile
            100                 105                 110

Val Phe Ala Gly Arg Gln Ala Ile Asp Gly Asp Thr Ala Gln Val Gly
        115                 120                 125

Pro Glu Ile Ala Glu His Leu Gly Ile Pro Gln Val Thr Tyr Val Glu
130                 135                 140

Lys Val Glu Val Asp Gly Asp Thr Leu Lys Ile Arg Lys Ala Trp Glu
145                 150                 155                 160

Asp Gly Tyr Glu Val Val Glu Val Lys Thr Pro Val Leu Leu Thr Ala
                165                 170                 175

Ile Lys Glu Leu Asn Val Pro Arg Tyr Met Ser Val Glu Lys Ile Phe
            180                 185                 190

Gly Ala Phe Asp Lys Glu Val Lys Met Trp Thr Ala Asp Asp Ile Asp
        195                 200                 205

Val Asp Lys Ala Asn Leu Gly Leu Lys Gly Ser Pro Thr Lys Val Lys
210                 215                 220

Lys Ser Ser Thr Lys Glu Val Lys Gly Gln Gly Glu Val Ile Asp Lys
225                 230                 235                 240

Pro Val Lys Glu Ala Ala Ala Tyr Val Val Ser Lys Leu Lys Glu Glu
                245                 250                 255

His Tyr Ile

<210> SEQ ID NO 8
<211> LENGTH: 336
<212> TYPE: PRT
<213> ORGANISM: Clostridium acetobutylicum

<400> SEQUENCE: 8

Met Asn Lys Ala Asp Tyr Lys Gly Val Trp Val Phe Ala Glu Gln Arg
1               5                   10                  15

Asp Gly Glu Leu Gln Lys Val Ser Leu Glu Leu Leu Gly Lys Gly Lys
            20                  25                  30

Glu Met Ala Glu Lys Leu Gly Val Gly Leu Thr Ala Val Leu Leu Gly
        35                  40                  45

His Asn Thr Glu Lys Met Ser Lys Asp Leu Leu Ser His Gly Ala Asp
50                  55                  60

Lys Val Leu Ala Ala Asp Asn Glu Leu Leu Ala His Phe Ser Thr Asp
65                  70                  75                  80

Gly Tyr Ala Lys Val Ile Cys Asp Leu Val Asn Glu Arg Lys Pro Glu
                85                  90                  95

Ile Leu Phe Ile Gly Ala Thr Phe Ile Gly Arg Asp Leu Gly Pro Arg
            100                 105                 110

Ile Ala Ala Arg Leu Ser Thr Gly Leu Thr Ala Asp Cys Thr Ser Leu
            115                 120                 125

Asp Ile Asp Val Glu Asn Arg Asp Leu Leu Ala Thr Arg Pro Ala Phe
130                 135                 140

Gly Gly Asn Leu Ile Ala Thr Ile Val Cys Ser Asp His Arg Pro Gln
145                 150                 155                 160

Met Ala Thr Val Arg Pro Gly Val Phe Glu Lys Leu Pro Val Asn Asp
                165                 170                 175

Ala Asn Val Ser Asp Asp Lys Ile Glu Lys Val Ala Ile Lys Leu Thr
            180                 185                 190

Ala Ser Asp Ile Arg Thr Lys Val Ser Lys Val Val Lys Leu Ala Lys
            195                 200                 205

Asp Ile Ala Asp Ile Gly Glu Ala Lys Val Leu Val Ala Gly Gly Arg
210                 215                 220

Gly Val Gly Ser Lys Glu Asn Phe Glu Lys Leu Glu Glu Leu Ala Ser
225                 230                 235                 240

Leu Leu Gly Gly Thr Ile Ala Ala Ser Arg Ala Ala Ile Glu Lys Glu
                245                 250                 255

Trp Val Asp Lys Asp Leu Gln Val Gly Gln Thr Gly Lys Thr Val Arg
            260                 265                 270

Pro Thr Leu Tyr Ile Ala Cys Gly Ile Ser Gly Ala Ile Gln His Leu
            275                 280                 285

Ala Gly Met Gln Asp Ser Asp Tyr Ile Ile Ala Ile Asn Lys Asp Val
            290                 295                 300

Glu Ala Pro Ile Met Lys Val Ala Asp Leu Ala Ile Val Gly Asp Val
305                 310                 315                 320

Asn Lys Val Val Pro Glu Leu Ile Ala Gln Val Lys Ala Ala Asn Asn
                325                 330                 335

<210> SEQ ID NO 9
<211> LENGTH: 584
<212> TYPE: PRT
<213> ORGANISM: Thermotoga maritima

<400> SEQUENCE: 9

Met Val His Val Lys Met Lys Gly Ser Lys Met Leu Phe Glu Ala Leu
1               5                   10                  15

Leu Lys Glu Gly Val Asp Thr Ile Phe Gly Ile Pro Gly Gly Ala Ile
                20                  25                  30

Ile Asn Val Tyr Asp Glu Leu Cys Asn Tyr Glu Asp Lys Ile Asn Phe
            35                  40                  45

Tyr Leu Phe Arg His Glu Gln Gly Ala Thr His Ala Ala Asp Gly Tyr
50                  55                  60

Ala Arg Val Thr Gly Lys Pro Gly Val Val Ile Val Thr Ser Gly Pro
65                  70                  75                  80

Gly Ala Thr Asn Thr Val Thr Gly Ile Ala Thr Ala Tyr Met Asp Ser
                85                  90                  95

Ile Pro Ile Val Val Ile Thr Gly Gln Val Pro Thr Ser Phe Ile Gly

-continued

```
                100                 105                 110
Thr Asp Ala Phe Gln Glu Val Asp Val Thr Gly Ile Thr Met Pro Ile
            115                 120                 125
Thr Lys His Asn His Leu Val Thr Ser Ile Glu Glu Leu Pro Tyr Ala
            130                 135                 140
Ile Lys Glu Met Phe Tyr Val Ala Thr Thr Gly Arg Pro Gly Pro Val
145                 150                 155                 160
Leu Leu Asp Phe Pro Lys Asp Ile Gln Thr Ala Glu Gly Glu Phe Asn
                165                 170                 175
Tyr Pro Asp Thr Val Glu Ile Pro Gly Tyr Lys Pro Thr Val Lys Gly
                180                 185                 190
His Pro Lys Gln Ile Lys Lys Ala Val Glu Leu Leu Lys Glu Ser Lys
            195                 200                 205
Arg Pro Val Val Ile Val Gly Gly Gly Ala Asn Leu Ser Gly Ala Met
            210                 215                 220
Asp Leu Val Asn Gln Phe Ile Asp Lys Phe Lys Val Pro Ala Val Ser
225                 230                 235                 240
Thr Leu Met Gly Arg Gly Val Asn Pro Ser Asp Glu Lys Leu Tyr Tyr
                245                 250                 255
Glu Gly Ile Gly Met His Gly Thr Tyr Tyr Gly Asn Tyr Ala Val Ala
            260                 265                 270
Asn Ala Asp Leu Ile Ile Ala Leu Gly Val Arg Phe Ser Asp Arg Ile
            275                 280                 285
Leu Gly Asn Pro Arg Thr Phe Ala Lys Asn Ala Arg Ile Val His Val
            290                 295                 300
Asp Ile Asp Pro Ala Glu Ile Gly Lys Asn Val Arg Val Asp Val Pro
305                 310                 315                 320
Ile Val Gly Asp Leu Lys Ser Val Leu Glu Glu Phe Leu Lys Tyr Glu
                325                 330                 335
Ile Glu Thr Asp Phe Ser Asp Trp Ile Glu Glu Leu Gln Glu Ile Lys
            340                 345                 350
Lys Lys Tyr Pro Leu Thr Tyr Lys Arg Asp Gly Lys Leu Ile Lys Pro
            355                 360                 365
Gln Tyr Val Val Glu Lys Val Asn Glu Val Phe Pro Asp Asp Thr Val
            370                 375                 380
Val Val Ala Asp Val Gly Gln Asn Gln Met Trp Val Ala Gln Phe Tyr
385                 390                 395                 400
Lys Phe Lys His Gln Arg Ser Phe Leu Cys Ser Gly Gly Leu Gly Thr
                405                 410                 415
Met Gly Tyr Ala Leu Pro Ala Gly Ile Gly Ala Lys Ile Gly Ala Pro
            420                 425                 430
Asp Lys Glu Val Val Phe Ala Gly Asp Gly Gly Phe Gln Met Asn
            435                 440                 445
Ile Gln Glu Leu Met Thr Ile Lys Arg Tyr Asn Leu Pro Val Lys Ile
            450                 455                 460
Ile Val Met Asp Asn Lys Ala Leu Gly Met Val Arg Gln Trp Gln Gln
465                 470                 475                 480
Leu Phe Phe Asn Cys Arg Tyr Ser Ala Thr Ile Leu Ser Asp Asn Pro
                485                 490                 495
Asp Phe Ala Lys Ile Ala Glu Ala Val Gly Ile Lys Ala Met Arg Ile
            500                 505                 510
Glu Lys Pro Asp Gln Val Asp Glu Ala Ile Glu Lys Leu Ala Lys Ser
            515                 520                 525
```

```
Lys Glu Pro Met Leu Ile His Ala Val Val Asp Pro Ala Glu Asn Val
            530                 535                 540
Leu Pro Met Val Pro Pro Gly Gly Asp Val Gly Thr Pro Leu Ile Glu
545                 550                 555                 560
Ala Pro Tyr Asp Glu Thr Phe Val Glu Arg Val Leu Lys Val Ile Glu
                565                 570                 575
Glu Ser Arg Arg Gly Asp Glu Arg
            580

<210> SEQ ID NO 10
<211> LENGTH: 336
<212> TYPE: PRT
<213> ORGANISM: Thermotoga maritima

<400> SEQUENCE: 10

Met Ala Val Ile Tyr Tyr Asp Lys Asp Ala Asp Leu Asn Leu Ile Lys
1               5                   10                  15
Asp Lys Lys Ile Ala Ile Ile Gly Tyr Gly Ser Gln Gly His Ala His
            20                  25                  30
Ala Leu Asn Leu Lys Asp Ser Gly Leu Asn Val Val Val Gly Leu Arg
        35                  40                  45
Glu Gly Ser Lys Ser Trp Lys Lys Ala Glu Glu Gln Gly Leu Thr Val
50                  55                  60
Lys Thr Ile Glu Glu Ala Ala Lys Glu Ala Asp Ile Ile Met Ile Leu
65                  70                  75                  80
Ile Pro Asp Glu His Gln Pro Glu Ile Tyr Lys Lys Tyr Ile Glu Lys
                85                  90                  95
His Leu Thr Glu Gly Lys Met Leu Met Phe Ala His Gly Phe Asn Ile
            100                 105                 110
His Tyr His Gln Ile Ile Pro Pro Lys Asn Val Asp Val Thr Met Ile
        115                 120                 125
Ala Pro Lys Ser Pro Gly His Ile Val Arg Arg Glu Tyr Val Glu Gly
    130                 135                 140
Arg Gly Val Pro Ala Leu Val Ala Val Tyr Gln Asp Tyr Thr Gly Lys
145                 150                 155                 160
Ala Lys Asp Ile Ala Leu Ala Tyr Ala Lys Gly Ile Gly Val Thr Arg
                165                 170                 175
Ala Gly Val Ile Glu Thr Thr Phe Lys Glu Thr Glu Thr Asp Leu
            180                 185                 190
Phe Gly Glu Gln Ala Val Leu Cys Gly Gly Val Thr Ala Leu Ile Lys
        195                 200                 205
Ala Gly Phe Glu Thr Leu Val Asp Ala Gly Tyr Gln Pro Glu Ile Ala
    210                 215                 220
Tyr Phe Glu Cys Leu Asn Glu Leu Lys Leu Ile Val Asp Leu Ile Tyr
225                 230                 235                 240
Glu Gly Gly Leu Ser Phe Met Arg Tyr Ser Val Ser Asn Thr Ala Glu
                245                 250                 255
Tyr Gly Asp Tyr Ile Ser Gln Glu Lys Ile Val Thr Lys Glu Val Arg
            260                 265                 270
Glu Asn Met Lys Gln Met Leu Lys Asp Ile Gln Thr Gly Lys Phe Ala
        275                 280                 285
Lys Asp Trp Ile Leu Glu Asn Gln Ala Gly Arg Pro Tyr Phe Tyr Thr
    290                 295                 300
Met Arg Lys Lys Glu Ser Glu His Leu Ile Glu Lys Val Gly Lys Glu
```

```
                305                 310                 315                 320
Leu Arg Lys Met Met Pro Trp Leu Lys Glu Arg Asn Val Asp Glu Glu
                    325                 330                 335

<210> SEQ ID NO 11
<211> LENGTH: 554
<212> TYPE: PRT
<213> ORGANISM: Thermotoga maritima

<400> SEQUENCE: 11

Met Arg Ser Asp Val Ile Lys Lys Gly Leu Glu Arg Val Pro His Arg
1               5                   10                  15

Ser Leu Leu Lys Ala Leu Gly Ile Thr Asp Asp Glu Met Arg Arg Pro
            20                  25                  30

Phe Ile Gly Ile Val Ser Ser Trp Asn Glu Ile Ile Pro Gly His Val
        35                  40                  45

His Leu Asp Lys Val Val Glu Ala Val Lys Ala Gly Val Arg Met Ala
    50                  55                  60

Gly Gly Val Pro Phe Val Phe Pro Thr Ile Gly Ile Cys Asp Gly Ile
65                  70                  75                  80

Ala Met Asp His Arg Gly Met Lys Phe Ser Leu Pro Ser Arg Glu Leu
                85                  90                  95

Ile Ala Asp Ser Ile Glu Ile Val Ala Ser Gly Phe Pro Phe Asp Gly
            100                 105                 110

Leu Val Phe Val Pro Asn Cys Asp Lys Ile Thr Pro Gly Met Met Met
        115                 120                 125

Ala Met Gly Arg Leu Asn Ile Pro Ser Val Leu Ile Ser Gly Gly Pro
    130                 135                 140

Met Leu Ala Gly Arg Tyr Asn Gly Arg Asp Ile Asp Leu Ile Thr Val
145                 150                 155                 160

Phe Glu Ala Val Gly Gly Tyr Lys Val Gly Lys Val Asp Glu Glu Thr
                165                 170                 175

Leu Lys Ala Ile Glu Asp Leu Ala Cys Pro Gly Ala Gly Ser Cys Ala
            180                 185                 190

Gly Leu Phe Thr Ala Asn Thr Met Asn Ser Leu Ala Glu Ala Leu Gly
        195                 200                 205

Ile Ala Pro Arg Gly Asn Gly Thr Val Pro Ala Val His Ala Lys Arg
    210                 215                 220

Leu Arg Met Ala Lys Glu Ala Gly Met Leu Val Glu Leu Val Lys
225                 230                 235                 240

Arg Asp Val Lys Pro Arg Asp Ile Val Thr Leu Asp Ser Phe Met Asn
                245                 250                 255

Ala Val Met Val Asp Leu Ala Thr Gly Gly Ser Thr Asn Thr Val Leu
            260                 265                 270

His Leu Lys Ala Ile Ala Glu Ser Phe Gly Ile Asp Phe Asp Ile Lys
        275                 280                 285

Leu Phe Asp Glu Leu Ser Arg Lys Ile Pro His Ile Cys Asn Ile Ser
    290                 295                 300

Pro Val Gly Pro Tyr His Ile Gln Asp Leu Asp Asp Ala Gly Gly Ile
305                 310                 315                 320

Tyr Ala Val Met Lys Arg Leu Gln Glu Asn Gly Leu Leu Lys Glu Asp
                325                 330                 335

Val Met Thr Ile Tyr Leu Arg Lys Ile Gly Asp Leu Val Arg Glu Ala
            340                 345                 350
```

Lys Ile Leu Asn Glu Asp Val Ile Arg Pro Phe Asp Asn Pro Tyr His
            355                 360                 365

Lys Glu Gly Gly Leu Gly Ile Leu Phe Gly Asn Leu Ala Pro Glu Gly
370                 375                 380

Ala Val Ala Lys Leu Ser Gly Val Pro Glu Lys Met Met His His Val
385                 390                 395                 400

Gly Pro Ala Val Val Phe Glu Asp Gly Glu Ala Thr Lys Ala Ile
                405                 410                 415

Leu Ser Gly Lys Ile Lys Lys Gly Asp Val Val Ile Arg Tyr Glu
            420                 425                 430

Gly Pro Lys Gly Gly Pro Gly Met Arg Glu Met Leu Ser Pro Thr Ser
            435                 440                 445

Ala Ile Val Gly Met Gly Leu Ala Glu Asp Val Ala Leu Ile Thr Asp
450                 455                 460

Gly Arg Phe Ser Gly Gly Ser His Gly Ala Val Ile Gly His Val Ser
465                 470                 475                 480

Pro Glu Ala Ala Glu Gly Gly Pro Ile Gly Ile Val Lys Asp Gly Asp
                485                 490                 495

Leu Ile Glu Ile Asp Phe Glu Lys Arg Thr Leu Asn Leu Leu Ile Ser
            500                 505                 510

Asp Glu Glu Phe Glu Arg Arg Met Lys Glu Phe Thr Pro Leu Val Lys
            515                 520                 525

Glu Val Asp Ser Asp Tyr Leu Arg Arg Tyr Ala Phe Phe Val Gln Ser
            530                 535                 540

Ala Ser Lys Gly Ala Ile Phe Arg Lys Pro
545                 550

<210> SEQ ID NO 12
<211> LENGTH: 548
<212> TYPE: PRT
<213> ORGANISM: Lactococcus lactis

<400> SEQUENCE: 12

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
            35                  40                  45

Glu Leu Asn Ala Ser Tyr Met Ala Asp Gly Tyr Ala Arg Thr Lys Lys
50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
            85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
            130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
            165                 170                 175

```
Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
            530                 535                 540

Gln Asn Lys Ser
545

<210> SEQ ID NO 13
<211> LENGTH: 366
<212> TYPE: PRT
<213> ORGANISM: Sulfolobus solfataricus
```

<400> SEQUENCE: 13

```
Met Lys Ala Ile Ile Val Lys Pro Pro Asn Ala Gly Val Gln Val Lys
1               5                   10                  15
Asp Val Asp Glu Lys Lys Leu Asp Ser Tyr Gly Lys Ile Lys Ile Arg
            20                  25                  30
Thr Ile Tyr Asn Gly Ile Cys Gly Thr Asp Arg Glu Ile Val Asn Gly
        35                  40                  45
Lys Leu Thr Leu Ser Thr Leu Pro Lys Gly Lys Asp Phe Leu Val Leu
    50                  55                  60
Gly His Glu Ala Ile Gly Val Val Glu Glu Ser Tyr His Gly Phe Ser
65                  70                  75                  80
Gln Gly Asp Leu Val Met Pro Val Asn Arg Arg Gly Cys Gly Ile Cys
                85                  90                  95
Arg Asn Cys Leu Val Gly Arg Pro Asp Phe Cys Glu Thr Gly Glu Phe
            100                 105                 110
Gly Glu Ala Gly Ile His Lys Met Asp Gly Phe Met Arg Glu Trp Trp
        115                 120                 125
Tyr Asp Asp Pro Lys Tyr Leu Val Lys Ile Pro Lys Ser Ile Glu Asp
    130                 135                 140
Ile Gly Ile Leu Ala Gln Pro Leu Ala Asp Ile Glu Lys Ser Ile Glu
145                 150                 155                 160
Glu Ile Leu Glu Val Gln Lys Arg Val Pro Val Trp Thr Cys Asp Asp
                165                 170                 175
Gly Thr Leu Asn Cys Arg Lys Val Leu Val Val Gly Thr Gly Pro Ile
            180                 185                 190
Gly Val Leu Phe Thr Leu Leu Phe Arg Thr Tyr Gly Leu Glu Val Trp
        195                 200                 205
Met Ala Asn Arg Arg Glu Pro Thr Glu Val Glu Gln Thr Val Ile Glu
    210                 215                 220
Glu Thr Lys Thr Asn Tyr Tyr Asn Ser Ser Asn Gly Tyr Asp Lys Leu
225                 230                 235                 240
Lys Asp Ser Val Gly Lys Phe Asp Val Ile Ile Asp Ala Thr Gly Ala
                245                 250                 255
Asp Val Asn Ile Leu Gly Asn Val Ile Pro Leu Leu Gly Arg Asn Gly
            260                 265                 270
Val Leu Gly Leu Phe Gly Phe Ser Thr Ser Gly Ser Val Pro Leu Asp
        275                 280                 285
Tyr Lys Thr Leu Gln Glu Ile Val His Thr Asn Lys Thr Ile Ile Gly
    290                 295                 300
Leu Val Asn Gly Gln Lys Pro His Phe Gln Gln Ala Val Val His Leu
305                 310                 315                 320
Ala Ser Trp Lys Thr Leu Tyr Pro Lys Ala Ala Lys Met Leu Ile Thr
                325                 330                 335
Lys Thr Val Ser Ile Asn Asp Glu Lys Glu Leu Leu Lys Val Leu Arg
            340                 345                 350
Glu Lys Glu His Gly Glu Ile Lys Ile Arg Ile Leu Trp Glu
        355                 360                 365

<210> SEQ ID NO 14
<211> LENGTH: 273
<212> TYPE: PRT
<213> ORGANISM: Picrophilus torridus

<400> SEQUENCE: 14
```

-continued

```
Met Glu Leu Asn Ile Glu Pro Gln Arg Leu Gly Glu Ser Pro Ile Tyr
1               5                   10                  15

Ile Arg Glu Leu Asp Thr Phe Leu Trp Val Asp Ile Leu Asn Gly Asp
            20                  25                  30

Ile Phe Ser Tyr Asn Gly Asn Ala Lys Met Glu Met His Val Asn Asp
        35                  40                  45

Met Ile Thr Ser Ile Ser Pro Tyr Lys Gly Thr Glu Val Ile Ala Ser
    50                  55                  60

Leu Arg Asp Gly Ile Ala Ile Ile Asp Trp Lys Asn Lys Ile Thr Asn
65                  70                  75                  80

Thr Leu Leu Lys Leu Asp Phe Pro Glu Asn Ile Arg Phe Asn Asp Gly
                85                  90                  95

Arg Cys Asp Ala Arg Gly Arg Phe Phe Ile Gly Thr Met Asp Met Asn
            100                 105                 110

Glu Lys Glu Pro Leu Gly Ala Leu Tyr Lys Phe Ser Gly Arg Lys Leu
        115                 120                 125

Glu Arg Val Leu Asp Asn Val Thr Ile Ser Asn Gly Ile Ala Trp Ser
    130                 135                 140

Leu Asp Ser Arg Phe Met Tyr Tyr Ile Asp Ser Pro Arg Lys Ser Val
145                 150                 155                 160

Gln Val Phe Asp Tyr Asp Leu Ser Met Gly Arg Ile Thr Arg His Leu
                165                 170                 175

Tyr Asp Ile Asp Leu Lys Asn Tyr Ser Gly Val Pro Asp Gly Met Ala
            180                 185                 190

Ile Asp Ile Asn Asn Asn Leu Trp Val Ala Ile His Gly Ser Ser Leu
        195                 200                 205

Ile Ser Val Ile Asp Pro Ala Lys Asn Glu Ile Leu Asn Glu Val Lys
    210                 215                 220

Ile Ala Ala Lys Lys Val Thr Ser Cys Thr Phe Gly Ser Val Asn Met
225                 230                 235                 240

Asp Lys Leu Phe Val Thr Ser Ala Tyr Asp Gly Thr Gly Gly Ile Pro
                245                 250                 255

Phe Ile Ile Asp Thr Gly Ser Arg Gly Val Glu Leu Asn Arg Tyr Ile
            260                 265                 270

Pro

<210> SEQ ID NO 15
<211> LENGTH: 395
<212> TYPE: PRT
<213> ORGANISM: Sulfolobus solfataricus

<400> SEQUENCE: 15

Met Arg Ile Arg Glu Ile Glu Pro Ile Val Leu Thr Ser Lys Glu Lys
1               5                   10                  15

Gly Ser Ala Thr Trp Ala Ser Ile Met Ile Val Thr Arg Val Ile Thr
            20                  25                  30

Glu Asn Gly Glu Val Gly Tyr Gly Glu Ala Val Pro Thr Leu Arg Val
        35                  40                  45

Ile Ser Val Tyr Asn Ala Ile Lys Gln Val Ser Lys Ala Tyr Ile Gly
    50                  55                  60

Lys Glu Val Glu Glu Val Lys Asn Tyr His Glu Trp Tyr Lys Gln
65                  70                  75                  80

Asp Phe Tyr Leu Ala Arg Ser Phe Glu Ser Ala Thr Ala Val Ser Ala
                85                  90                  95
```

```
Ile Asp Ile Ala Ser Trp Asp Ile Ile Gly Lys Glu Leu Gly Ala Pro
            100                 105                 110
Ile His Lys Leu Leu Gly Gly Lys Thr Arg Asp Arg Val Pro Val Tyr
        115                 120                 125
Ala Asn Gly Trp Tyr Gln Asp Cys Val Thr Pro Glu Glu Phe Ala Glu
    130                 135                 140
Lys Ala Lys Asp Val Val Lys Met Gly Tyr Lys Ala Leu Lys Phe Asp
145                 150                 155                 160
Pro Phe Gly Pro Tyr Tyr Asp Trp Ile Asp Glu Arg Gly Leu Arg Glu
                165                 170                 175
Ala Glu Glu Arg Val Lys Ala Val Arg Glu Ala Val Gly Asp Asn Val
            180                 185                 190
Asp Ile Leu Ile Glu His His Gly Arg Phe Asn Ala Asn Ser Ala Ile
        195                 200                 205
Met Ile Ala Lys Arg Leu Glu Lys Tyr Asn Pro Gly Phe Met Glu Glu
    210                 215                 220
Pro Val His His Glu Asp Val Ile Gly Leu Arg Lys Tyr Lys Ala Ser
225                 230                 235                 240
Thr His Leu Arg Val Ala Leu Gly Glu Arg Leu Ile Ser Glu Lys Glu
                245                 250                 255
Thr Ala Phe Tyr Val Glu Gly Leu Val Asn Ile Leu Gln Pro Asp
            260                 265                 270
Leu Thr Asn Ile Gly Gly Val Thr Val Gly Arg Ser Val Ile Lys Ile
        275                 280                 285
Ala Glu Ala Asn Asp Val Glu Val Ala Phe His Asn Ala Phe Gly Ser
    290                 295                 300
Ile Gln Asn Ala Val Glu Ile Gln Leu Ser Ala Val Thr Gln Asn Leu
305                 310                 315                 320
Tyr Leu Leu Glu Asn Phe Tyr Asp Trp Phe Pro Gln Trp Lys Arg Asp
                325                 330                 335
Leu Val Tyr Asn Glu Thr Pro Val Glu Gly Gly His Val Lys Val Pro
            340                 345                 350
Tyr Lys Pro Gly Leu Gly Val Ser Ile Asn Glu Lys Ile Ile Glu Gln
        355                 360                 365
Leu Arg Ala Glu Pro Ile Pro Leu Asp Val Ile Glu Glu Pro Val Trp
    370                 375                 380
Val Val Lys Gly Thr Trp Lys Asn Tyr Gly Val
385                 390                 395

<210> SEQ ID NO 16
<211> LENGTH: 308
<212> TYPE: PRT
<213> ORGANISM: Sulfolobus solfataricus

<400> SEQUENCE: 16

Met Gly Arg Gln Gly Asn Leu Glu Glu Leu Trp Cys Leu Arg Met Pro
1               5                   10                  15
Glu Ile Ile Thr Pro Ile Ile Thr Pro Phe Thr Lys Asp Asn Arg Ile
            20                  25                  30
Asp Lys Glu Lys Leu Lys Ile His Ala Glu Asn Leu Ile Arg Lys Gly
        35                  40                  45
Ile Asp Lys Leu Phe Val Asn Gly Thr Thr Gly Leu Gly Pro Ser Leu
    50                  55                  60
Ser Pro Glu Glu Lys Leu Glu Asn Leu Lys Ala Val Tyr Asp Val Thr
65                  70                  75                  80
```

```
Asn Lys Ile Ile Phe Gln Val Gly Gly Leu Asn Leu Asp Asp Ala Ile
                85                  90                  95

Arg Leu Ala Lys Leu Ser Lys Asp Phe Asp Ile Val Gly Ile Ala Ser
            100                 105                 110

Tyr Ala Pro Tyr Tyr Pro Arg Met Ser Glu Lys His Leu Val Lys
        115                 120                 125

Tyr Phe Lys Thr Leu Cys Glu Val Ser Pro His Pro Val Tyr Leu Tyr
        130                 135                 140

Asn Tyr Pro Thr Ala Thr Gly Lys Asp Ile Asp Ala Lys Val Ala Lys
145                 150                 155                 160

Glu Ile Gly Cys Phe Thr Gly Val Lys Asp Thr Ile Glu Asn Ile Ile
                165                 170                 175

His Thr Leu Asp Tyr Lys Arg Leu Asn Pro Asn Met Leu Val Tyr Ser
            180                 185                 190

Gly Ser Asp Met Leu Ile Ala Thr Val Ala Ser Thr Gly Leu Asp Gly
        195                 200                 205

Asn Val Ala Ala Gly Ser Asn Tyr Leu Pro Glu Val Thr Val Thr Ile
210                 215                 220

Lys Lys Leu Ala Met Glu Arg Lys Ile Asp Glu Ala Leu Lys Leu Gln
225                 230                 235                 240

Phe Leu His Asp Glu Val Ile Glu Ala Ser Arg Ile Phe Gly Ser Leu
                245                 250                 255

Ser Ser Asn Tyr Val Leu Thr Lys Tyr Phe Gln Gly Tyr Asp Leu Gly
            260                 265                 270

Tyr Pro Arg Pro Pro Ile Phe Pro Leu Asp Asp Glu Glu Arg Gln
        275                 280                 285

Leu Ile Lys Lys Val Glu Gly Ile Arg Ala Lys Leu Val Glu Leu Lys
        290                 295                 300

Ile Leu Lys Glu
305

<210> SEQ ID NO 17
<211> LENGTH: 501
<212> TYPE: PRT
<213> ORGANISM: Flavobacterium frigidimaris

<400> SEQUENCE: 17

Met Ser Asn Thr Ile Gln Arg Pro Glu Phe Lys Ala Lys Tyr Asp Asn
1               5                   10                  15

Tyr Ile Asn Gly Lys Phe Thr Ala Pro Val Lys Gly Glu Tyr Phe Asp
            20                  25                  30

Val Leu Ser Pro Ile Asp Gly Lys Val Phe Thr Lys Ala Ala His Ser
        35                  40                  45

Gly Lys Glu Asp Leu Glu Leu Ala Val Asp Ala Ala Tyr Glu Ala Phe
    50                  55                  60

Lys Thr Trp Gly Lys Thr Ser Val Thr Glu Arg Ser Ile Leu Leu Asn
65                  70                  75                  80

Lys Ile Ala Gln Lys Ile Glu Asp Asn Leu Glu Tyr Ile Ala Thr Val
                85                  90                  95

Glu Thr Ile Asp Asn Gly Lys Pro Ile Arg Glu Thr Leu Ala Ala Asp
            100                 105                 110

Ile Pro Leu Ala Ile Asp His Phe Arg Tyr Phe Ala Gly Val Ile Arg
        115                 120                 125

Ala Glu Glu Ser Ser Ile Ala Glu Leu Asp Ser Gln Thr Val Ser Ile
```

```
                130                 135                 140
Ala Leu Ser Glu Pro Leu Gly Val Val Ala Gln Ile Ile Pro Trp Asn
145                 150                 155                 160

Phe Pro Ile Leu Met Ala Val Trp Lys Ile Ala Pro Ala Leu Ala Ala
                165                 170                 175

Gly Asn Thr Ile Val Leu Lys Pro Ala Glu Ser Thr Pro Ile Ser Ile
            180                 185                 190

Leu Val Leu Met Glu Leu Ile Gly Asp Ile Leu Pro Pro Gly Val Leu
        195                 200                 205

Asn Ile Val Asn Gly Phe Gly Ala Glu Leu Gly Arg Pro Leu Val Thr
210                 215                 220

Asn Lys Lys Val Ala Lys Ala Ala Phe Thr Gly Ser Thr Thr Thr Gly
225                 230                 235                 240

Arg Leu Val Met Gln Tyr Ala Thr Glu Asn Ile Ile Pro Val Thr Leu
                245                 250                 255

Glu Leu Gly Gly Lys Ser Pro Asn Ile Phe Phe Pro Ser Val Ala Asp
            260                 265                 270

His Asp Asp Asp Phe Phe Asp Lys Ala Ile Glu Gly Ala Val Leu Phe
        275                 280                 285

Ala Leu Asn Gln Gly Glu Ile Cys Thr Cys Pro Ser Arg Leu Leu Ile
290                 295                 300

His Glu Asp Ile Tyr Glu Lys Phe Ile Ala Arg Val Ile Glu Arg Thr
305                 310                 315                 320

Glu Ala Ile Ile Ala Gly Asn Pro Leu Asp Lys Ser Thr Met Ile Gly
                325                 330                 335

Ala Gln Thr Ser Leu Val Gln Lys Glu Lys Ile Met Ser Tyr Ile Lys
            340                 345                 350

Leu Gly Lys Glu Gly Ala Glu Leu Leu Thr Gly Gly Asp Glu Asn
        355                 360                 365

His Leu Gly Gly Asp Leu Glu Gly Gly Tyr Tyr Ile Lys Pro Thr Leu
370                 375                 380

Phe Lys Gly His Asn Lys Met Arg Ile Phe Gln Glu Glu Ile Phe Gly
385                 390                 395                 400

Pro Val Leu Ala Val Thr Thr Phe Lys Thr Thr Glu Glu Ala Ile Glu
                405                 410                 415

Ile Ala Asn Asp Thr Met Tyr Gly Leu Gly Ala Gly Val Trp Thr Arg
            420                 425                 430

Asp Ala His Glu Ile Tyr Gln Val Pro Arg Ala Ile Gln Ser Gly Arg
        435                 440                 445

Val Trp Ile Asn Gln Tyr His Ser Tyr Pro Ala Gly Ala Pro Phe Gly
450                 455                 460

Gly Tyr Lys Gln Ser Gly Ile Gly Arg Glu Asn His Lys Met Met Leu
465                 470                 475                 480

Gly Gln Tyr Arg Gln Thr Lys Asn Met Leu Ile Ser Tyr Asp Lys Lys
                485                 490                 495

Lys Leu Gly Phe Phe
            500

<210> SEQ ID NO 18
<211> LENGTH: 400
<212> TYPE: PRT
<213> ORGANISM: Sulfolobus solfataricus

<400> SEQUENCE: 18
```

```
Met Asp Ile Val Asp Lys Ile Leu Glu Tyr Thr Asp Pro Tyr Lys Ala
1               5                   10                  15
Leu Gln Glu Lys Val Arg Val Tyr Asn Asn Ile Leu Leu Phe Asn Asn
            20                  25                  30
Glu Lys Ile Pro Phe Lys Lys Pro Ile Leu Ile Ser Ile Gly Lys Ala
        35                  40                  45
Ser Leu Pro Met Ala Arg Phe Phe Arg Glu Arg Met Glu Leu Lys Ala
50                  55                  60
Lys Leu Ile Val Thr Pro Lys Gly Thr Asn Lys Glu Asn Asp Val
65                  70                  75                  80
Ile Glu Ala Gly His Pro Leu Pro Asp Glu Asn Ser Ile Lys Ala Gly
                85                  90                  95
Lys Arg Met Ile Glu Leu Leu Ala Asn Glu Asp Tyr Asp Leu Val Ile
            100                 105                 110
Phe Ala Ile Ser Gly Gly Ala Ser Ala Leu Val Glu Tyr Ser Glu Ile
        115                 120                 125
Pro Leu Asp Glu Leu Lys Ile Ile Asn Lys Val Leu Val Thr Ser Gly
    130                 135                 140
Leu Gly Ile Asn Lys Ile Asn Ile Val Arg Lys His Leu Ser Lys Val
145                 150                 155                 160
Lys Gly Gly Lys Ile Leu Glu Tyr Val Lys Asp Lys Ile Pro Ile Val
                165                 170                 175
Ser Phe Ile Val Ser Asp Val Pro Gly Asn Asp Ile Ser Ser Ile Gly
            180                 185                 190
Ser Gly Leu Thr Ser Ile Asp Asn Ser Ser Asn Asp Ala Leu Glu
        195                 200                 205
Ile Leu Lys Ala Ile Gly Leu Glu Lys Tyr Ser Lys Tyr Leu Thr Glu
    210                 215                 220
Thr Pro Lys Ser Phe Ser Arg Ile Val Lys Asn Tyr Ile Ile Leu Asp
225                 230                 235                 240
Asn Met Glu Val Leu Arg Lys Leu Ala Asn Thr Leu Val Asn Ser Phe
                245                 250                 255
Ile Leu Thr Ser Glu Ile Arg Gly Glu Ala Arg Asp Val Gly Ala Ile
            260                 265                 270
Ile Ala Ser Ile Tyr Asn Ser Ser Glu Ser Tyr Asn Ile Pro Phe Arg
        275                 280                 285
Arg Pro Tyr Tyr Leu Leu Val Gly Gly Glu Pro Glu Val Thr Ile Gln
    290                 295                 300
Gly Lys Ala Gly Lys Gly Gly Arg Asn Gly Glu Val Cys Leu Ser Phe
305                 310                 315                 320
Leu Lys Tyr Ala Lys Lys Arg Asn Arg Phe Glu Leu Leu Gly Phe Ala
                325                 330                 335
Thr Asp Gly Ile Asp Gly Asn Ser Glu Tyr Ala Gly Cys Lys Val Ser
            340                 345                 350
Ser Asp Met Glu Ile Arg Glu Asp Glu Ile Asn Asn Ala Leu Glu Thr
        355                 360                 365
His Asn Ser Tyr Gly Leu Leu Glu Ser His Lys Ala Val Ile Lys Thr
    370                 375                 380
Gly Tyr Thr His Thr Asn Val Asn Asn Ile Tyr Val Leu Arg Ala Pro
385                 390                 395                 400

<210> SEQ ID NO 19
<211> LENGTH: 419
<212> TYPE: PRT
```

<213> ORGANISM: Sulfolobus solfataricus

<400> SEQUENCE: 19

```
Met Ile Asn Arg Phe Ser Ile Glu Lys Val Lys Gly Leu Glu Ile Val
1               5                   10                  15
Asp Ser Arg Gly Asn Pro Thr Ile Arg Val Phe Ile Arg Thr Ser Asp
            20                  25                  30
Gly Val Glu Ser Phe Gly Asp Ala Pro Ala Gly Ala Ser Lys Gly Thr
        35                  40                  45
Arg Glu Ala Val Glu Val Arg Asp Glu Asn Gly Leu Thr Val Lys Arg
50                  55                  60
Ala Val Asp Ile Val Asn Tyr Ile Ile Asp Pro Ala Leu His Gly Ile
65                  70                  75                  80
Asp Val Arg Glu Gln Gly Ile Ile Asp Lys Leu Leu Lys Asp Ile Asp
                85                  90                  95
Ser Thr Glu Asn Lys Ser Lys Leu Gly Gly Asn Thr Ile Ile Ala Thr
            100                 105                 110
Ser Ile Ala Ala Leu Lys Thr Ala Ser Lys Ala Leu Gly Leu Glu Val
        115                 120                 125
Phe Lys Tyr Ile Ser Gly Pro Arg Leu Pro Lys Ile Pro Ile Pro Leu
130                 135                 140
Leu Asn Ile Ile Asn Gly Gly Leu His Ala Gly Asn Lys Leu Lys Ile
145                 150                 155                 160
Gln Glu Phe Ile Ile Val Pro Ile Lys Phe Asn Thr Phe Lys Glu Ala
                165                 170                 175
Leu Phe Ala Ala Ile Asp Val Tyr Arg Thr Leu Lys Gly Leu Ile Thr
            180                 185                 190
Glu Arg Tyr Gly Lys Ile Tyr Thr Ala Val Gly Asp Glu Gly Gly Phe
        195                 200                 205
Ser Pro Pro Leu Glu Asp Thr Arg Glu Ala Leu Asp Leu Ile Tyr Thr
210                 215                 220
Ser Ile Asn Asn Ala Gly Tyr Glu Gly Lys Ile Tyr Met Gly Met Asp
225                 230                 235                 240
Ala Ala Gly Ser Asp Phe Tyr Asp Ser Lys Glu Lys Tyr Ile Ile
                245                 250                 255
Asp Gly Arg Glu Leu Asp Pro Asn Gln Leu Leu Glu Phe Tyr Leu Asp
            260                 265                 270
Leu Val Lys Gln Tyr Pro Ile Val Tyr Leu Glu Asp Pro Phe Glu Glu
        275                 280                 285
Asn Ser Phe Asp Met Phe Ser Gln Leu Gln Asn Lys Leu Ser Ser Thr
290                 295                 300
Ile Ile Thr Gly Asp Asp Leu Tyr Thr Thr Asn Ile Lys Tyr Leu Lys
305                 310                 315                 320
Ile Gly Ile Glu Lys Arg Ser Thr Lys Gly Val Ile Val Lys Pro Asn
                325                 330                 335
Gln Val Gly Thr Ile Ser Glu Thr Phe Glu Phe Thr Asn Leu Ala Arg
            340                 345                 350
Arg Asn Ser Met Lys Leu Ile Thr Ser His Arg Ser Gly Glu Thr Glu
        355                 360                 365
Asp Asn Phe Ile Ala Asp Phe Ala Val Gly Ile Glu Ser Asp Phe Ile
370                 375                 380
Lys Val Gly Ala Pro Ala Arg Gly Glu Arg Thr Ser Lys Tyr Asn Lys
385                 390                 395                 400
```

```
Leu Leu Glu Ile Glu Asn Lys Phe Gly Leu Glu Tyr Glu Gly Lys Tyr
            405                 410                 415

Phe Tyr Leu

<210> SEQ ID NO 20
<211> LENGTH: 452
<212> TYPE: PRT
<213> ORGANISM: Sulfolobus solfataricus

<400> SEQUENCE: 20

Met Arg Lys Thr Lys Ile Val Ala Thr Leu Gly Pro Ser Ser Glu Glu
1               5                   10                  15

Lys Val Lys Glu Leu Ala Glu Tyr Val Asp Val Phe Arg Ile Asn Phe
            20                  25                  30

Ala His Gly Asp Glu Thr Ser His Arg Lys Tyr Phe Asp Leu Ile Arg
        35                  40                  45

Thr Tyr Ala Pro Glu Ser Ser Ile Ile Val Asp Leu Pro Gly Pro Lys
    50                  55                  60

Leu Arg Leu Gly Glu Leu Lys Glu Pro Ile Glu Val Lys Lys Gly Asp
65                  70                  75                  80

Lys Ile Val Phe Ser Gln Lys Asp Gly Ile Pro Val Asp Glu Leu
            85                  90                  95

Phe Tyr Ser Ala Val Lys Glu Asn Ser Asp Ile Leu Ile Ala Asp Gly
            100                 105                 110

Thr Ile Arg Val Arg Val Lys Ser Lys Ala Lys Asp Arg Val Glu Gly
        115                 120                 125

Thr Val Ile Glu Gly Gly Ile Leu Leu Ser Arg Lys Gly Ile Asn Ile
    130                 135                 140

Pro Asn Val Asn Leu Lys Ser Gly Ile Thr Asp Asn Asp Leu Lys Leu
145                 150                 155                 160

Leu Lys Arg Ala Leu Asp Leu Gly Ala Asp Tyr Ile Gly Leu Ser Phe
            165                 170                 175

Val Ile Ser Glu Asn Asp Val Lys Lys Val Lys Glu Phe Val Gly Asp
            180                 185                 190

Glu Ala Trp Val Ile Ala Lys Ile Glu Lys Ser Glu Ala Leu Lys Asn
        195                 200                 205

Leu Thr Asn Ile Val Asn Glu Ser Asp Gly Ile Met Val Ala Arg Gly
    210                 215                 220

Asp Leu Gly Val Glu Thr Gly Leu Glu Asn Leu Pro Leu Ile Gln Arg
225                 230                 235                 240

Arg Ile Val Arg Thr Ser Arg Val Phe Gly Lys Pro Val Ile Leu Ala
            245                 250                 255

Thr Gln Val Leu Thr Ser Met Ile Asn Ser Pro Ile Pro Thr Arg Ala
            260                 265                 270

Glu Ile Ile Asp Ile Ser Asn Ser Ile Met Gln Gly Val Asp Ser Ile
        275                 280                 285

Met Leu Ser Asp Glu Thr Ala Ile Gly Asn Tyr Pro Val Glu Ser Val
    290                 295                 300

Arg Thr Leu His Asn Ile Ile Ser Asn Val Glu Lys Ser Val Lys His
305                 310                 315                 320

Arg Pro Ile Gly Pro Leu Asn Ser Glu Ser Asp Ala Ile Ala Leu Ala
            325                 330                 335

Ala Val Asn Ala Ser Lys Val Ser Lys Ala Asp Val Ile Val Val Tyr
            340                 345                 350
```

```
Ser Arg Ser Gly Asn Ser Ile Leu Arg Val Ser Arg Leu Arg Pro Glu
            355                 360                 365

Arg Asn Ile Ile Gly Val Ser Pro Asp Pro Arg Leu Ala Lys Lys Phe
    370                 375                 380

Lys Leu Cys Tyr Gly Val Ile Pro Ile Ser Ile Asn Lys Lys Met Gln
385                 390                 395                 400

Ser Ile Asp Glu Ile Ile Asp Val Ser Ala Lys Leu Met Gln Glu Lys
                405                 410                 415

Ile Lys Asp Leu Lys Phe Lys Lys Ile Val Ile Val Gly Gly Asp Pro
            420                 425                 430

Lys Gln Glu Ala Gly Lys Thr Asn Phe Val Ile Val Lys Thr Leu Glu
            435                 440                 445

Gln Gln Lys Lys
        450

<210> SEQ ID NO 21
<211> LENGTH: 297
<212> TYPE: PRT
<213> ORGANISM: Picrophilus torridus

<400> SEQUENCE: 21

Met Lys Val Ser Val Gln Val Asn Ser Tyr Tyr Asn Asn Glu Met Ser
1               5                   10                  15

Lys Lys Leu Leu Glu Leu Cys Arg Asp Ile Thr Gly Leu Asp Ala Val
            20                  25                  30

Pro Gly Phe Asp Asp Ala Glu Ile Ile Leu Phe Ser Gly Arg Pro
            35                  40                  45

Val Pro Gly Lys Lys Thr Lys Phe Met Gln Ser Leu Ser Ala Gly Val
50                  55                  60

Asn His Leu Asp Phe Ser Lys Ile Pro Asp Asn Ile Ile Ala Ser
65                  70                  75                  80

Asn Ala Asp Ala Tyr Ser Ile Pro Val Ala Glu Thr Ala Ile Gly Leu
                85                  90                  95

Met Leu Ala Trp Ala Arg Lys Ile Cys Ile Ser Asn Tyr Asn Ile His
            100                 105                 110

Asn Asn Asn Tyr Lys Arg Leu Asp Tyr Lys Glu Tyr Val Ser Leu Tyr
        115                 120                 125

Asn Lys Ser Leu Gly Ile Leu Gly Tyr Gly Gly Ile Gly Arg Arg Thr
    130                 135                 140

Ala Leu Ile Ala Lys Ser Phe Gly Met Asn Ile Tyr Ala Tyr Ser Arg
145                 150                 155                 160

Ser Tyr Lys Asn Asp Gly Ile Ser Ser Tyr Met Glu Pro Glu Asp Ile
                165                 170                 175

Met Lys Lys Ser Asp Phe Val Leu Ile Ser Leu Pro Leu Thr Lys Glu
            180                 185                 190

Thr Ala Asn Ser Ile Asn Asp Lys Met Leu Ser Leu Phe Arg Gly Leu
        195                 200                 205

Ala Ile Ile Asn Val Gly Arg Ala Gly Val Val Asp Arg Asn Ser Met
    210                 215                 220

Leu Asn Phe Leu Arg Asn His Asn Asp Lys Tyr Tyr Leu Thr Asp Val
225                 230                 235                 240

Trp Trp Asn Glu Pro Ile Ile Asn Glu Asn Ile Pro Asp Asn Val Ile
                245                 250                 255

Ile Thr Pro His Ser Ala Gly Met Ser Asp Asn Ile Tyr Gln Pro Ala
            260                 265                 270
```

Val Ala Ala Ile Glu Asn Ile Lys Asn Tyr Ile Asn Gly Lys Pro Lys
            275                 280                 285

Asn Ile Val Lys Arg Ser Asp Tyr Ile
        290                 295

<210> SEQ ID NO 22
<211> LENGTH: 384
<212> TYPE: PRT
<213> ORGANISM: Sulfolobus solfataricus

<400> SEQUENCE: 22

Met Asp Lys Leu Leu His Val Gly Pro Thr Thr Ile Lys Glu Asp
1               5                   10                  15

Val Leu Val Ala Gly Leu Glu Asn Asn Val Gly Phe Thr Ser Lys Glu
            20                  25                  30

Phe Val Glu Ala Leu Ala Tyr Ser Leu Lys Gly Leu Arg Tyr Val Met
        35                  40                  45

Gly Ala Ser Lys Asn Tyr Gln Pro Leu Ile Ile Pro Gly Gly Gly Thr
    50                  55                  60

Ser Ala Met Glu Ser Val Thr Ser Leu Leu Lys Pro Asn Asp Lys Ile
65                  70                  75                  80

Leu Val Val Ser Asn Gly Val Phe Gly Asp Arg Trp Glu Gln Ile Phe
                85                  90                  95

Lys Arg Tyr Pro Val Asn Val Lys Val Leu Arg Pro Ser Pro Gly Asp
            100                 105                 110

Tyr Val Lys Pro Gly Glu Val Glu Glu Val Arg Lys Ser Glu Tyr
        115                 120                 125

Lys Leu Val Ala Leu Thr His Val Glu Thr Ser Thr Gly Val Arg Glu
    130                 135                 140

Pro Val Lys Asp Val Ile Asn Lys Ile Arg Lys Tyr Val Glu Leu Ile
145                 150                 155                 160

Val Val Asp Gly Val Ser Ser Val Gly Ala Glu Glu Val Lys Ala Glu
                165                 170                 175

Glu Trp Asn Val Asp Val Tyr Leu Thr Ala Ser Gln Lys Ala Leu Gly
            180                 185                 190

Ser Ala Ala Gly Leu Gly Leu Leu Leu Ser Pro Lys Ala Leu Ser
    195                 200                 205

Ile Leu Asp Ser Gln Asn Ser Ile Ala Gly Tyr Tyr Leu Asp Leu Arg
    210                 215                 220

Asn Trp Leu Pro Val Met Arg Gly Ala Glu Glu Gly Lys Ala Ala Tyr
225                 230                 235                 240

Phe Ala Thr Pro Pro Val His Val Ile Leu Gln Leu Ala Glu Ala Phe
                245                 250                 255

Arg Leu Ile Glu Lys Glu Gly Ile Glu Asn Arg Ile Lys Arg His Thr
            260                 265                 270

Met Val Ala Ser Ala Ile Arg Ala Gly Leu Glu Ala Leu Gly Leu Glu
    275                 280                 285

Ile Val Ala Arg Arg Pro Glu Ser Tyr Ser Asn Thr Val Thr Gly Val
    290                 295                 300

Ile Leu Lys Val Ala Asp Pro Gln Lys Val Leu Ala Gly Thr Val Asn
305                 310                 315                 320

Glu Gly Val Glu Phe Ala Pro Gly Val His Pro Ala Phe Lys Tyr Phe
                325                 330                 335

Arg Ile Gly His Met Gly Trp Val Thr Pro Asn Asp Ala Ile Ile Ala

```
                    340                 345                 350
Ile Ser Val Ile Glu Arg Thr Leu Arg Lys Leu Gly Glu Pro Ile Arg
            355                 360                 365

Phe Gly Glu Gly Val Lys Ala Val Glu Glu Val Leu Phe Ser Ala Arg
            370                 375                 380

<210> SEQ ID NO 23
<211> LENGTH: 284
<212> TYPE: PRT
<213> ORGANISM: Thermus thermophilus

<400> SEQUENCE: 23

Met Pro Leu Thr Leu Asn Gln Leu Ala Glu Leu Ser Gly Arg Ala Ser
1               5                   10                  15

Glu His Val Leu Ala Glu Val Glu Glu Thr Gly Thr Pro Ala Glu
            20                  25                  30

Glu Ile Leu Ala Arg Leu Arg Glu Arg Leu Ala Val Met Arg Asp Ser
        35                  40                  45

Val Arg Arg Gly Leu Ala Ser Asp Ala Pro Ser Val Ala Gly Leu Val
    50                  55                  60

Gly Lys Asn Ala Lys Thr Leu Trp Glu Ala Pro Asp Pro Leu Gln Asp
65                  70                  75                  80

Pro Leu Leu Lys Arg Val Gln Ala Tyr Ala Met Ala Val Asn Glu Glu
                85                  90                  95

Asn Ala Arg Met Gly Arg Ile Val Ala Ala Pro Thr Ala Gly Ser Ala
            100                 105                 110

Gly Thr Leu Pro Gly Ala Leu Leu Gly Val Ala Asp His Leu Gly Ile
        115                 120                 125

Pro Asp Glu Glu Leu Leu Met Pro Leu Val Leu Ala Gly Gly Val Ala
    130                 135                 140

Lys Met Ile Gly Arg Val Ile His Ile Ala Gly Ala Ser Gly Gly Cys
145                 150                 155                 160

Gln Ala Glu Ile Gly Ser Ser Ala Ala Met Ala Ala Ala Ala Val Thr
                165                 170                 175

Glu Leu Leu Gly Gly Thr Pro Glu Ala Cys Ala His Ala Ala Ala Leu
            180                 185                 190

Ala Leu Gln Asn Thr Leu Gly Leu Val Cys Asp Pro Val Gly Gly Phe
        195                 200                 205

Val Glu Val Pro Cys Val Met Arg Asn Gly Phe Tyr Ala Val His Ala
    210                 215                 220

Val Ser Ala Ala Ser Met Ala Leu Ala Gly Ile Arg Ser Val Ile Pro
225                 230                 235                 240

Pro Asp Glu Val Val Leu Ala Met Ala Gly Ile Gly Arg Leu Leu Pro
                245                 250                 255

Leu Glu Leu Lys Glu Thr Gly Leu Gly Gly Leu Ala Asp Thr Pro Thr
            260                 265                 270

Gly Arg Arg Leu Ala Glu Glu Ala Leu Lys Lys Thr
        275                 280

<210> SEQ ID NO 24
<211> LENGTH: 220
<212> TYPE: PRT
<213> ORGANISM: Thermus thermophilus

<400> SEQUENCE: 24

Met Gly Leu Leu Asp Met Ile Gly Pro Val Met Val Gly Pro Ser Ser
```

```
1               5                   10                  15
Ser His Thr Ala Gly Ala Cys Arg Leu Ala Leu Leu Ala Arg His Leu
            20                  25                  30

Leu Gly Glu Lys Pro Lys Arg Val Glu Phe Gly Leu His Gly Ser Phe
            35                  40                  45

Ala Lys Thr Gly Lys Gly His Gly Thr His Leu Ala Leu Ala Ala Gly
    50                  55                  60

Val Leu Gly Leu Thr Pro Asp Asp Glu Arg Leu Lys Glu Ser Leu Ser
65              70                  75                  80

Leu Ala Glu Arg Glu Gly Val Glu Val Val Phe Lys Glu Val Glu Leu
                85                  90                  95

Gly Asp Val His Pro Asn Thr Val Arg Met Val Leu Glu Gly Glu Lys
            100                 105                 110

Glu Arg Leu Ala Val Thr Gly Ser Ser Leu Gly Gly Gly Leu Val Arg
            115                 120                 125

Val Phe Asp Val Asp Gly Phe Glu Val Arg Ile Thr Gly Ser Ala Pro
        130                 135                 140

Thr Leu Val Ile Lys Asn Val Asp Thr Pro Gly Val Val Ala Arg Val
145                 150                 155                 160

Ala Arg Ile Leu Ala Asp Asp Glu Val Asn Ile Ala Tyr Leu Thr Val
                165                 170                 175

Ser Arg Lys Lys Arg Gly Gly Glu Ala Met Met Ser Ile Glu Val Asp
            180                 185                 190

Arg Pro Leu Ser Glu Val Pro Leu Arg Tyr Leu Glu His Leu Ser Tyr
            195                 200                 205

Ile Leu Trp Val Arg Gln Ile Pro Pro Val Met Gly
            210                 215                 220

<210> SEQ ID NO 25
<211> LENGTH: 369
<212> TYPE: PRT
<213> ORGANISM: Thermus thermophilus

<400> SEQUENCE: 25

Met Val Ile Gly Val Pro Arg Glu Ile Lys Thr Leu Glu Asn Arg Val
1               5                   10                  15

Ala Leu Thr Pro Gly Gly Val Glu Ser Leu Val Arg Arg Gly His Thr
            20                  25                  30

Val Leu Val Glu Arg Gly Ala Gly Glu Gly Ser Gly Leu Ser Asp Ala
            35                  40                  45

Glu Tyr Ala Arg Ala Gly Ala Glu Leu Val Gly Arg Glu Glu Ala Trp
    50                  55                  60

Gly Ala Glu Met Val Val Lys Val Lys Glu Pro Leu Pro Glu Glu Tyr
65              70                  75                  80

Gly Phe Leu Arg Glu Gly Leu Ile Leu Phe Thr Tyr Leu His Leu Ala
                85                  90                  95

Ala Asp Arg Gly Leu Thr Glu Ala Met Leu Arg Ser Gly Val Thr Gly
            100                 105                 110

Ile Ala Tyr Glu Thr Val Gln Leu Pro Asp Gly Thr Leu Pro Leu Leu
            115                 120                 125

Val Pro Met Ser Glu Val Ala Gly Arg Met Ala Pro Gln Val Gly Ala
        130                 135                 140

Gln Phe Leu Glu Lys Pro Lys Gly Gly Arg Gly Val Leu Leu Gly Gly
145                 150                 155                 160
```

Val Pro Gly Val Ala Pro Ser Val Val Ile Leu Gly Gly Thr
                165                 170                 175

Val Gly Thr Asn Ala Ala Lys Ile Ala Leu Gly Met Gly Ala Gln Val
            180                 185                 190

Thr Ile Leu Asp Val Asn His Lys Arg Leu Gln Tyr Leu Asp Asp Val
            195                 200                 205

Phe Gly Gly Arg Val Val Thr Leu Thr Ala Thr Glu Ala Asn Ile Lys
210                 215                 220

Lys Ser Val Gln His Ala Asp Leu Leu Ile Gly Ala Val Leu Val Pro
225                 230                 235                 240

Gly Ala Lys Ala Pro Lys Leu Val Thr Arg Asp Met Leu Ser Leu Met
                245                 250                 255

Lys Glu Gly Ala Val Ile Val Asp Val Ala Val Asp Gln Gly Gly Cys
            260                 265                 270

Val Glu Thr Ile Arg Pro Thr Thr His Ala Glu Pro Thr Tyr Val Val
            275                 280                 285

Asp Gly Val Val His Tyr Gly Val Ala Asn Met Pro Gly Ala Val Pro
            290                 295                 300

Arg Thr Ser Thr Phe Ala Leu Thr Asn Gln Thr Leu Pro Tyr Val Leu
305                 310                 315                 320

Lys Leu Ala Glu Lys Gly Leu Asp Ala Leu Leu Glu Asp Ala Ala Leu
                325                 330                 335

Leu Lys Gly Leu Asn Thr His Lys Gly Arg Leu Thr His Pro Gly Val
            340                 345                 350

Ala Glu Ala Phe Gly Leu Pro Tyr Thr Pro Pro Glu Glu Ala Leu Arg
            355                 360                 365

Gly

<210> SEQ ID NO 26
<211> LENGTH: 558
<212> TYPE: PRT
<213> ORGANISM: Sulfolobus solfataricus

<400> SEQUENCE: 26

Met Pro Ala Lys Leu Asn Ser Pro Ser Arg Tyr His Gly Ile Tyr Asn
1               5                   10                  15

Ala Pro His Arg Ala Phe Leu Arg Ser Val Gly Leu Thr Asp Glu Glu
            20                  25                  30

Ile Gly Lys Pro Leu Val Ala Ile Ala Thr Ala Trp Ser Glu Ala Gly
        35                  40                  45

Pro Cys Asn Phe His Thr Leu Ala Leu Ala Arg Val Ala Lys Glu Gly
    50                  55                  60

Thr Lys Glu Ala Gly Leu Ser Pro Leu Ala Phe Pro Thr Met Val Val
65                  70                  75                  80

Asn Asp Asn Ile Gly Met Gly Ser Glu Gly Met Arg Tyr Ser Leu Val
                85                  90                  95

Ser Arg Asp Leu Ile Ala Asp Met Val Glu Ala Gln Phe Asn Ala His
            100                 105                 110

Ala Phe Asp Gly Leu Val Gly Ile Gly Gly Cys Asp Lys Thr Thr Pro
        115                 120                 125

Gly Ile Leu Met Ala Met Ala Arg Leu Asn Val Pro Ser Ile Tyr Ile
    130                 135                 140

Tyr Gly Gly Ser Ala Glu Pro Gly Tyr Phe Met Gly Lys Arg Leu Thr
145                 150                 155                 160

Ile Glu Asp Val His Glu Ala Ile Gly Ala Tyr Leu Ala Lys Arg Ile
                165                 170                 175

Thr Glu Asn Glu Leu Tyr Glu Ile Glu Lys Arg Ala His Pro Thr Leu
            180                 185                 190

Gly Thr Cys Ser Gly Leu Phe Thr Ala Asn Thr Met Gly Ser Met Ser
        195                 200                 205

Glu Ala Leu Gly Met Ala Leu Pro Gly Ser Ala Ser Pro Thr Ala Thr
    210                 215                 220

Ser Ser Arg Arg Val Met Tyr Val Lys Glu Thr Gly Lys Ala Leu Gly
225                 230                 235                 240

Ser Leu Ile Glu Asn Gly Ile Lys Ser Arg Glu Ile Leu Thr Phe Glu
                245                 250                 255

Ala Phe Glu Asn Ala Ile Thr Thr Leu Met Ala Met Gly Gly Ser Thr
            260                 265                 270

Asn Ala Val Leu His Leu Leu Ala Ile Ala Tyr Glu Ala Gly Val Lys
        275                 280                 285

Leu Thr Leu Asp Asp Phe Asn Arg Ile Ser Lys Arg Thr Pro Tyr Ile
    290                 295                 300

Ala Ser Met Lys Pro Gly Gly Asp Tyr Val Met Ala Asp Leu Asp Glu
305                 310                 315                 320

Val Gly Gly Val Pro Val Val Leu Lys Lys Leu Leu Asp Ala Gly Leu
                325                 330                 335

Leu His Gly Asp Val Leu Thr Val Thr Gly Lys Thr Met Lys Gln Asn
            340                 345                 350

Leu Glu Gln Tyr Lys Tyr Pro Asn Val Pro His Ser His Ile Val Arg
        355                 360                 365

Asp Val Lys Asn Pro Ile Lys Pro Arg Gly Gly Ile Val Ile Leu Lys
    370                 375                 380

Gly Ser Leu Ala Pro Glu Gly Ala Val Ile Lys Val Ala Ala Thr Asn
385                 390                 395                 400

Val Val Lys Phe Glu Gly Lys Ala Lys Val Tyr Asn Ser Glu Asp Asp
                405                 410                 415

Ala Phe Lys Gly Val Gln Ser Gly Glu Val Ser Glu Gly Glu Val Val
            420                 425                 430

Ile Ile Arg Tyr Glu Gly Pro Lys Gly Ala Pro Gly Met Pro Glu Met
        435                 440                 445

Leu Arg Val Thr Ala Ala Ile Met Gly Ala Gly Leu Asn Asn Val Ala
    450                 455                 460

Leu Val Thr Asp Gly Arg Phe Ser Gly Ala Thr Arg Gly Pro Met Val
465                 470                 475                 480

Gly His Val Ala Pro Glu Ala Met Val Gly Gly Pro Ile Ala Ile Val
                485                 490                 495

Glu Asp Gly Asp Thr Ile Val Ile Asp Val Glu Ser Glu Arg Leu Asp
            500                 505                 510

Leu Lys Leu Ser Glu Glu Ile Lys Asn Arg Leu Lys Arg Trp Ser
        515                 520                 525

Pro Pro Ser Pro Arg Tyr Lys Ser Gly Leu Leu Ala Lys Tyr Ala Ser
    530                 535                 540

Leu Val Ser Gln Ala Ser Met Gly Ala Val Thr Arg Pro Ala
545                 550                 555

<210> SEQ ID NO 27
<211> LENGTH: 385
<212> TYPE: PRT

<213> ORGANISM: Sulfolobus solfataricus

<400> SEQUENCE: 27

```
Met Gln Val Leu Lys Arg Lys Val Leu Ala Leu Val Gly Asn His Ala
1               5                   10                  15

Val Ala Tyr Ala Val Lys Gln Ala Lys Pro Lys Val Leu Ala Val Phe
            20                  25                  30

Pro Ile Thr Pro Gln Thr Thr Met Leu Glu Lys Leu Ser Glu Tyr Ile
        35                  40                  45

Ser Ser Glu Glu Leu Lys Ala Glu Leu Ile Lys Val Glu Ser Glu His
50                  55                  60

Ser Ala Leu Ala Ser Ile Tyr Gly Ala Ala Leu Ala Gly Ala Arg Val
65                  70                  75                  80

Phe Thr Ala Thr Ser Ser Gln Gly Leu Leu Tyr Met Thr Glu Met Ile
                85                  90                  95

Tyr Trp Ala Gly Gly Gln Arg Val Pro Ile Val Ala Ala Val Ala Thr
            100                 105                 110

Arg Ala Ile Ala Glu Pro Trp Ser Ile Trp Asp Asp His Gln Asp Phe
        115                 120                 125

Val Ser Lys Arg Asp Ala Ile Trp Ile Gln Ile Met Ala Glu Asn Val
    130                 135                 140

Gln Glu Ala Tyr Asp Met Thr Ile Gln Ala Phe Arg Ile Ser Glu Asp
145                 150                 155                 160

Glu Arg Val Ile Leu Pro Val Met Met Gly Phe Asp Gly Phe Ile Leu
                165                 170                 175

Thr His Thr Met Glu Arg Ile Glu Val Leu Glu Asp Asn Glu Val Asp
            180                 185                 190

Asn Phe Leu Pro Pro Arg Gln Phe Asn Leu Ile Asp Phe Ser Asp Pro
        195                 200                 205

Ile Ala Ile Gly Pro Ile Ala Thr Pro Glu Glu Tyr Ile Lys Tyr Arg
    210                 215                 220

Tyr Glu Ala Met Lys Ala Met Glu Arg Ala Lys Gly Val Ile Glu Glu
225                 230                 235                 240

Ile Met Gly Glu Tyr Glu Arg Ile Ser Gly Arg Lys Gln His Gly Leu
                245                 250                 255

Val Glu Cys Tyr Lys Cys Glu Asp Ala Lys Tyr Val Phe Val Thr Met
            260                 265                 270

Gly Ala Trp Ser Gly Asp Gly Lys Ala Ala Val Asp Arg Leu Arg Asp
        275                 280                 285

Ser Gly Val Lys Thr Gly Leu Leu Lys Ile Arg Val Phe Arg Pro Phe
    290                 295                 300

Pro Lys Glu Lys Val Glu Glu Tyr Leu Arg Ser Met Lys Gly Val Val
305                 310                 315                 320

Val Phe Asp Arg Ala Tyr Ser Tyr Gly Tyr Gly Ile Leu Val Asn
                325                 330                 335

Glu Ile Lys Ala Ala Leu Tyr Gly Tyr Arg Val Pro Val Tyr Ser Val
            340                 345                 350

Val Ala Gly Ile Gly Gly Lys Asp Val Arg Pro Arg His Phe Gln Lys
        355                 360                 365

Val Ile Glu Asp Leu Ile Asn Asp Asn Leu Glu Glu Arg Trp Leu
    370                 375                 380

Phe
385
```

<210> SEQ ID NO 28
<211> LENGTH: 300
<212> TYPE: PRT
<213> ORGANISM: Sulfolobus solfataricus

<400> SEQUENCE: 28

Met Ala Val Leu Ser Ser Gln Val Thr Pro Lys Arg Met Pro Lys Phe
1               5                   10                  15

Tyr Arg Gly Asn Ala Ala Cys Pro Gly Cys Pro Ile Pro Lys Glu Leu
            20                  25                  30

Asp Val Ala Leu Glu Val Leu Gly Asn Lys Thr Val Leu Val Val Pro
        35                  40                  45

Ala Ser Cys Thr Thr Ile Ile Met Gly Asp Thr Asn Gly Met Pro Ser
    50                  55                  60

Thr Val Pro Val Val His Ser Ala Phe Gly Ala Ala Ala Ile Gly
65                  70                  75                  80

Ser Gly Ile Val Arg Ser Leu Arg Met Arg Gly Asp Asn Asp Ala Ile
                85                  90                  95

Val Ala Val Trp Ala Gly Asp Gly Ser Thr Gly Asp Ile Gly Phe Ala
            100                 105                 110

Ala Val Ser Gly Ala Ala Glu Arg Asn Glu Asp Ile Leu Tyr Ile Cys
        115                 120                 125

Tyr Asp Asn Glu Ala Tyr Met Asn Thr Gly Ile Gln Arg Ser Gly Leu
    130                 135                 140

Thr Pro Lys Gly Ala Trp Thr Thr Thr Pro Glu Gly Lys Arg Glu
145                 150                 155                 160

Val Lys Lys Pro Leu Pro Phe Ile Ile Ala Glu His Lys Val Pro Tyr
                165                 170                 175

Val Ala Thr Ala Ser Ile Ala Tyr Ile Tyr Asp Tyr Glu Ala Lys Met
            180                 185                 190

Arg Lys Ala Lys Gln Ile Arg Gly Phe Arg Tyr Ile His Leu Leu Ser
        195                 200                 205

Pro Cys Pro Pro Gly Trp Arg Phe Asp Ser Lys Leu Thr Ile Asp Ile
    210                 215                 220

Ala Lys Leu Ala Val Glu Thr Gly Val Trp Pro Leu Phe Glu Ile Glu
225                 230                 235                 240

Asn Gly Glu Phe Lys Leu Thr Ser Val Ser Lys Thr Leu Val Glu Lys
                245                 250                 255

Lys Asn Arg Lys Pro Val Ala Glu Tyr Leu Lys Leu Gln Gly Arg Phe
            260                 265                 270

Lys Gln Leu Thr Glu Glu Gln Ile Lys Gly Ile Gln Glu Glu Ile Asp
        275                 280                 285

Glu Met Trp Glu Glu Ile Lys Arg Leu Ile Lys Lys
    290                 295                 300

<210> SEQ ID NO 29
<211> LENGTH: 190
<212> TYPE: PRT
<213> ORGANISM: Sulfolobus solfataricus

<400> SEQUENCE: 29

Met Glu Tyr Tyr Asn Cys Asp Lys Met Thr Leu Ile Glu Leu Ala Leu
1               5                   10                  15

Arg Gly Arg Gly Gly Gln Gly Ile Val Thr Ala Gly Glu Leu Met Thr
            20                  25                  30

```
Lys Ala Met Val Leu Glu Asp Lys Tyr Ala Gln Ser Ile Pro Phe Phe
            35                  40                  45

Gly Gly Glu Arg Arg Gly Ala Pro Val Val Ser Phe Val Arg Leu Ser
 50                  55                  60

Asp Lys Pro Ile Leu Leu His Arg Glu Val Tyr Asn Pro Asp Gly Val
 65                  70                  75                  80

Ala Ile Phe Asp Val Ser Met Ile Gln Leu Ile Asn Val Thr Glu Gly
                 85                  90                  95

Leu Lys Glu Asn Gly Phe Leu Leu Asn Thr Asn Thr Pro Lys Arg
                100                 105                 110

Ile Trp Lys Asn Glu Tyr Val Val Asp Ala Thr Asn Ile Ala Lys Glu
                115                 120                 125

Leu Gly Leu Ile Val Ala Gly Trp Ala Ile Val Asn Thr Ala Met Ile
            130                 135                 140

Gly Ala Leu Ala Arg Ile Leu Gly Gln Pro Ser Leu His Ser Leu Glu
145                 150                 155                 160

Glu Ala Val Lys Glu Gly Phe Pro Gly Lys Ile Gly Glu Leu Asn Ala
                165                 170                 175

Glu Ala Val Glu Ile Gly Tyr Lys Glu Val Lys Arg Val Asp
                180                 185                 190

<210> SEQ ID NO 30
<211> LENGTH: 363
<212> TYPE: PRT
<213> ORGANISM: Sulfolobus solfataricus

<400> SEQUENCE: 30

Met Gly Val Lys Asp Glu Val Lys Tyr Val Glu Ile Val Tyr Arg Gly
 1                5                  10                  15

Ile Phe Gln Lys Arg Leu Ala Lys Tyr Ile Ala Glu Gly Ile Val Tyr
                 20                  25                  30

Thr Ala Arg Glu Met Gly Arg Pro Ala Leu Ser Phe Gly Arg Tyr Gly
             35                  40                  45

Asp Ser Pro Glu Arg Asn Gly Val Pro Ala Lys Tyr Tyr Val Gly Ile
 50                  55                  60

Gly Asp Gly Val Asn Glu Glu Asp Leu Ile Gly Tyr Ser Thr Arg Val
 65                  70                  75                  80

Glu Pro Asp Leu Val Asp Val Ile Ile Val Leu Asp Asp Thr Leu Leu
                 85                  90                  95

Lys Gly Val Glu Ser Trp Ala Trp Gln Gly Val Gln Pro Ile Asn Leu
                100                 105                 110

Lys Leu Lys Ser Asn Gly Thr Met Leu Val Thr Ser Thr Lys Arg Ile
            115                 120                 125

Asn Glu Leu Leu Lys Met Ile Pro Lys Lys Asp Phe Asn Trp Thr Leu
130                 135                 140

Gly Val Ile Lys Thr Glu Pro Ser Phe Ser Gly Leu Trp Ala Phe Lys
145                 150                 155                 160

Asp Asp Leu Thr Met Glu Lys Val Trp Gly Gly Leu Ala Lys Leu Arg
                165                 170                 175

Pro Asp Ile Ile Asp Leu Asp His Leu Leu Lys Tyr Val Thr Lys Lys
            180                 185                 190

Gln Asp Ala Asn Lys Arg Val Ser Ala Val Arg Glu Ala Tyr Ser Ser
            195                 200                 205

Val Asp Tyr Arg Thr Val Met Lys Gly Glu Gly Ile Asp Phe Val Tyr
            210                 215                 220
```

```
Asn Pro Pro Arg Leu Leu Thr Trp Gln Glu Met Leu Glu Gly Thr Val
225                 230                 235                 240

Ile Pro Ala Val Pro Arg Gly Lys Arg Asn Glu Leu Phe Lys Arg Gly
                245                 250                 255

Thr Thr Lys Phe Glu Arg Pro Thr Val Asp Phe Asp Thr Cys Ile Lys
            260                 265                 270

Cys Lys Leu Cys Trp Val Tyr Cys Pro Asp Glu Cys Phe Asp Glu Thr
        275                 280                 285

Pro Asp Gly Tyr Tyr Asp Ile Ala Tyr Asp Tyr Cys Val Gly Cys Gly
    290                 295                 300

Ile Cys Ala Glu Val Cys Pro Val Lys Asp Cys Ile Val Met Val Asp
305                 310                 315                 320

Glu Ser Met Phe Thr Asp Tyr Arg Arg Pro Tyr Glu Met Trp Lys Glu
                325                 330                 335

Asp Lys Ala Lys Tyr Lys Glu Trp Leu Lys Thr Val Arg Gln Ala Arg
            340                 345                 350

Lys Glu Arg Val Tyr Val Pro Gly Leu Gly Arg
        355                 360

<210> SEQ ID NO 31
<211> LENGTH: 404
<212> TYPE: PRT
<213> ORGANISM: Sulfolobus solfataricus

<400> SEQUENCE: 31

Met Lys Cys Glu Tyr Leu Ile Ile Gly Ser Gly Ile Ala Gly Tyr Asn
1               5                   10                  15

Ala Leu Lys Glu Leu Leu Gln Ile Lys Pro Asn Ser Arg Ile Ile Met
            20                  25                  30

Ile Thr Ser Asp Lys Tyr Tyr Pro Tyr Asp Arg Pro Pro Leu Ser Lys
        35                  40                  45

Asp Tyr Leu Lys Gly Lys Leu Glu Lys Asp Met Leu Phe Phe Glu Ser
    50                  55                  60

Asp Asp Phe Tyr Lys Arg Asp Asn Leu Glu Val Met Leu Asn Lys Ser
65                  70                  75                  80

Val Glu Arg Ile Asp Ala Asn Leu Lys Glu Ala Ile Leu Asn Asp Gly
                85                  90                  95

Ser Val Ile Ser Phe Asp Lys Ala Leu Ile Ser Thr Gly Gly Arg Pro
            100                 105                 110

Arg Arg Leu Asn Ile Pro Gly Ser Glu Asn Ala Leu Tyr Leu Arg Ser
        115                 120                 125

Leu Asp Asp Ala Asp Arg Ile Arg Glu Ala Ala Ser Lys Gly Lys Asn
    130                 135                 140

Ala Leu Ile Ile Gly Ala Gly Phe Ile Gly Val Glu Val Ala Ser Ser
145                 150                 155                 160

Leu Ile Thr Leu Gly Val Lys Thr Thr Val Glu Val Met Pro Tyr
                165                 170                 175

Ile Trp Asn Thr Phe Val Asp Glu Lys Val Ser Arg Val Ile Gln Gln
            180                 185                 190

Tyr Leu Glu Ser Lys Gly Ile Asn Phe Ile Leu Asn Glu Ser Val Lys
        195                 200                 205

Glu Ile Gln Gly Lys Ile Ala Thr Thr Ser Ser Gly Arg Lys Ile Glu
    210                 215                 220

Ala Asp Met Phe Leu Ile Ala Val Gly Ile Ser Pro Asn Val Glu Leu
```

```
              225                 230                 235                 240
Ala Gln Arg Ser Gly Met Gln Val Asp Asn Gly Ile Val Val Asn Glu
                    245                 250                 255

Tyr Leu Glu Thr Ser Ala Arg Asp Ile Tyr Ala Ala Gly Asp Ile Ala
                    260                 265                 270

Asn Ile Phe Asp Pro Arg Glu Gly Lys Arg Lys Arg Ile Glu His Trp
                275                 280                 285

Asn Asn Ala Glu Tyr Thr Gly Lys Leu Ala Ala Arg Asn Met Ala Gly
            290                 295                 300

Ser Arg Glu Ala Tyr Asn Phe Ile Ser Ser Ile Trp Ser Asp Ile Phe
305                 310                 315                 320

Asp Leu His Ile Glu Ser Ala Gly Glu Thr Arg Asn Tyr Asp Glu Tyr
                    325                 330                 335

Ile Ile Arg Gly Lys Phe Glu Leu Glu Arg Pro Arg Phe Ser Val Ile
                340                 345                 350

Tyr Leu Lys Gly Gly Ile Ile Lys Gly Tyr Leu Ala Ile Asn Arg Asn
                355                 360                 365

Val Lys Glu Ile Ile Ala Leu Asn Lys Leu Ile Gln Lys Gln Ala Asp
            370                 375                 380

Val Ser Ser Lys Arg Asp Lys Leu Ala Asp Glu Ser Phe Asp Leu Gln
385                 390                 395                 400

Lys Leu Leu Ile

<210> SEQ ID NO 32
<211> LENGTH: 572
<212> TYPE: PRT
<213> ORGANISM: Sulfolobus solfataricus

<400> SEQUENCE: 32

Met Pro Thr Gly Ala Arg Ile Leu Val Asp Ser Leu Lys Arg Glu Gly
1               5                   10                  15

Val Lys Val Val Phe Gly Ile Pro Gly Leu Ser Asn Met Gln Ile Tyr
                20                  25                  30

Asp Ala Phe Val Glu Asp Leu Ala Asn Gly Glu Leu Arg His Val Leu
            35                  40                  45

Met Arg His Glu Gln Ala Ala His Ala Ala Asp Gly Tyr Ala Arg
        50                  55                  60

Ala Ser Gly Val Pro Gly Val Cys Thr Ala Thr Ser Gly Pro Gly Thr
65                  70                  75                  80

Thr Asn Leu Thr Thr Gly Leu Ile Thr Ala Tyr Trp Asp Ser Ser Pro
                85                  90                  95

Val Ile Ala Ile Thr Gly Asn Val Pro Arg Ser Val Met Gly Lys Met
                100                 105                 110

Ala Phe Gln Glu Ala Asp Ala Met Gly Val Phe Glu Asn Val Thr Lys
            115                 120                 125

Tyr Val Ile Gly Ile Lys Arg Ile Asp Glu Ile Pro Gln Trp Ile Lys
        130                 135                 140

Asn Ala Phe Tyr Ile Ala Thr Thr Gly Arg Pro Gly Pro Val Val Val
145                 150                 155                 160

Asp Ile Pro Arg Asp Ile Phe Tyr Glu Lys Met Glu Glu Ile Lys Trp
                165                 170                 175

Pro Glu Lys Pro Leu Val Lys Gly Tyr Arg Asp Phe Pro Thr Arg Ile
                180                 185                 190

Asp Arg Leu Ala Leu Lys Lys Ala Ala Glu Ile Leu Ile Asn Ala Glu
```

```
            195                 200                 205
Arg Pro Ile Ile Leu Val Gly Thr Gly Val Val Trp Ala Asn Ala Thr
210                 215                 220

Pro Glu Val Leu Glu Leu Ala Glu Leu Leu His Ile Pro Ile Val Ser
225                 230                 235                 240

Thr Phe Pro Gly Lys Thr Ala Ile Pro His Asp His Pro Leu Tyr Phe
                245                 250                 255

Gly Pro Met Gly Tyr Tyr Gly Arg Ala Glu Ala Ser Met Ala Ala Leu
                260                 265                 270

Glu Ser Asp Ala Met Leu Val Val Gly Ala Arg Phe Ser Asp Arg Thr
            275                 280                 285

Phe Thr Ser Tyr Asp Glu Met Val Glu Thr Arg Lys Lys Phe Ile Met
290                 295                 300

Val Asn Ile Asp Pro Thr Asp Gly Glu Lys Ala Ile Lys Val Asp Val
305                 310                 315                 320

Gly Leu Tyr Gly Asn Ala Lys Ile Ile Leu Arg Glu Leu Ile Lys Ala
                325                 330                 335

Ile Ile Thr Leu Gly Gln Lys Arg Asp Lys Ser Ala Trp Ile Lys Arg
                340                 345                 350

Val Lys Glu Tyr Lys Glu Tyr Tyr Ser Gln Phe Tyr Tyr Thr Glu Glu
            355                 360                 365

Asn Gly Lys Leu Lys Pro Trp Lys Ile Met Lys Thr Ile Arg Gln Ser
370                 375                 380

Leu Pro Arg Asp Ala Ile Val Thr Thr Gly Val Gly Gln His Gln Met
385                 390                 395                 400

Trp Ala Glu Val Phe Trp Glu Val Leu Glu Pro Arg Thr Phe Leu Thr
                405                 410                 415

Ser Ser Gly Met Gly Thr Met Gly Phe Gly Leu Pro Ala Ala Met Gly
                420                 425                 430

Ala Lys Leu Ala Arg Pro Asp Lys Ile Val Val Asp Leu Asp Gly Asp
            435                 440                 445

Gly Ser Phe Leu Met Thr Gly Thr Asn Leu Ala Thr Ala Val Asp Glu
450                 455                 460

His Ile Pro Val Ile Ser Val Ile Phe Asp Asn Arg Thr Leu Gly Leu
465                 470                 475                 480

Val Arg Gln Val Gln Asp Leu Phe Phe Gly Arg Arg Ile Val Gly Val
                485                 490                 495

Asp Tyr Gly Pro Ser Pro Asp Phe Val Lys Leu Ala Glu Ala Phe Gly
                500                 505                 510

Ala Leu Gly Phe Asn Ala Thr Thr Tyr Glu Glu Ile Glu Lys Ser Ile
            515                 520                 525

Lys Ser Ala Ile Lys Glu Asp Ile Pro Ala Val Ile Arg Val Pro Val
        530                 535                 540

Asp Lys Glu Glu Leu Ala Leu Pro Thr Leu Pro Pro Gly Gly Arg Leu
545                 550                 555                 560

Lys Gln Val Ile Leu Arg Asp Pro Arg Lys Ser Ser
                565                 570

<210> SEQ ID NO 33
<211> LENGTH: 335
<212> TYPE: PRT
<213> ORGANISM: Sulfolobus solfataricus

<400> SEQUENCE: 33
```

```
Met Lys Cys Thr Ser Lys Ile Tyr Thr Asp Asn Asp Ala Asn Leu Asp
1               5                   10                  15

Leu Ile Lys Gly Lys Arg Ile Ala Val Leu Gly Tyr Gly Ser Gln Gly
            20                  25                  30

Arg Ala Trp Ala Gln Asn Leu Arg Asp Ser Gly Leu Asn Val Val Val
            35                  40                  45

Gly Leu Glu Asp Leu Gly Lys Ser Trp Glu Leu Ala Lys Ser Asp Gly
        50                  55                  60

Ile Thr Pro Leu His Thr Lys Asp Ala Val Lys Asp Ala Asp Ile Ile
65                  70                  75                  80

Ile Phe Leu Val Pro Asp Met Val Gln Arg Thr Leu Trp Leu Glu Ser
                85                  90                  95

Val Gln Pro Tyr Met Lys Gly Ala Asp Leu Val Phe Ala His Gly
                100                 105                 110

Phe Asn Ile His Tyr Lys Leu Ile Asp Pro Lys Asp Ser Asp Val
            115                 120                 125

Tyr Met Ile Ala Pro Lys Gly Pro Gly Thr Val Arg Glu Tyr Tyr
    130                 135                 140

Lys Ala Gly Gly Val Pro Ala Leu Val Ala Val His Gln Asp Val
145                 150                 155                 160

Ser Gly Thr Ala Leu His Lys Ala Leu Ala Ile Ala Lys Gly Ile Gly
                165                 170                 175

Ala Thr Arg Ala Gly Val Ile Pro Thr Thr Phe Lys Glu Glu Thr Glu
            180                 185                 190

Thr Asp Leu Phe Gly Glu Gln Val Ile Leu Val Gly Gly Ile Met Glu
        195                 200                 205

Leu Met Arg Ala Ala Phe Glu Thr Leu Val Glu Glu Gly Tyr Gln Pro
    210                 215                 220

Glu Val Ala Tyr Phe Glu Thr Ile Asn Glu Leu Lys Met Leu Val Asp
225                 230                 235                 240

Leu Val Tyr Glu Lys Gly Ile Ser Gly Met Leu Lys Ala Val Ser Asp
                245                 250                 255

Thr Ala Lys Tyr Gly Gly Met Thr Val Gly Lys Phe Val Ile Asp Glu
            260                 265                 270

Ser Val Arg Lys Arg Met Lys Glu Ala Leu Gln Arg Ile Lys Ser Gly
        275                 280                 285

Lys Phe Ala Glu Glu Trp Val Glu Tyr Gly Arg Gly Met Pro Thr
    290                 295                 300

Val Val Asn Gly Leu Ser Asn Val Gln Asn Ser Leu Glu Glu Lys Ile
305                 310                 315                 320

Gly Asn Gln Leu Arg Asp Leu Val Gln Lys Gly Lys Pro Lys Ser
                325                 330                 335

<210> SEQ ID NO 34
<211> LENGTH: 344
<212> TYPE: PRT
<213> ORGANISM: Flavobacterium frigidimaris

<400> SEQUENCE: 34

Met Leu Pro Lys Thr Met Lys Ala Ala Val Ile Arg Glu Phe Gly Ser
1               5                   10                  15

Leu Leu Lys Ile Glu Glu Val Glu Val Lys Arg Pro Gly Arg Asn Glu
            20                  25                  30

Ile Leu Val Lys Val Ile Ala Ser Gly Val Cys His Thr Asp Leu His
            35                  40                  45
```

```
Ala Val Glu Gly Asp Trp Pro Val Lys Pro Lys Met Pro Leu Ile Pro
 50                  55                  60

Gly His Glu Ala Val Gly Tyr Val Val Ala Val Gly Gln Glu Val Lys
 65                      70                  75                  80

Asn Val Lys Glu Gly Asp Ala Val Gly Val Pro Trp Leu Tyr Ser Ala
                     85                  90                  95

Cys Gly Gly Cys Asp Gln Cys Ile Thr Gly Trp Glu Thr Leu Cys Asp
                100                 105                 110

Thr Gln Gln Asn Gly Gly Tyr Ser Val Asp Gly Gly Phe Ala Glu Tyr
                115                 120                 125

Val Ile Ala Asp Ala Arg Tyr Val Gly Leu Leu Pro Ser Asn Val Asn
130                 135                 140

Phe Met Glu Met Ala Pro Ile Leu Cys Ala Gly Val Thr Val Tyr Lys
145                 150                 155                 160

Gly Leu Lys Glu Thr Glu Val Lys Pro Gly Glu Trp Val Ala Ile Ser
                165                 170                 175

Gly Ile Gly Gly Leu Gly His Val Ala Val Gln Tyr Ala Lys Ala Met
                180                 185                 190

Gly Met His Val Ala Ala Ile Asp Val Ala Asp Asp Lys Leu Asp Leu
                195                 200                 205

Ala Lys Lys Leu Gly Ala Asp Leu Val Val Asn Ala Lys Asn Gln Asn
210                 215                 220

Pro Gly Glu Phe Leu Lys Lys Glu Val Gly Gly Met His Gly Ala Leu
225                 230                 235                 240

Ile Thr Ala Val Ser Pro Ile Ala Phe Lys Gln Gly Leu Glu Thr Leu
                245                 250                 255

Arg Arg Lys Gly Thr Met Ala Leu Asn Gly Leu Pro Pro Gly Asn Phe
                260                 265                 270

Asp Leu Ser Ile Phe Asp Thr Val Leu Asn Arg Ile Thr Ile Arg Gly
                275                 280                 285

Ser Ile Val Gly Thr Arg Lys Asp Met Lys Glu Ala Ile Glu Phe Ala
                290                 295                 300

Val Glu Gly Lys Val Lys Ala Thr Val Thr Pro Ala Lys Leu Glu Asn
305                 310                 315                 320

Ile Asn Glu Val Phe Asp Lys Met Lys Lys Gly Gln Ile Glu Gly Arg
                325                 330                 335

Val Val Leu Glu Ile Ala Lys Ala
                340

<210> SEQ ID NO 35
<211> LENGTH: 285
<212> TYPE: PRT
<213> ORGANISM: Brevibacillus brevis

<400> SEQUENCE: 35

Met Lys Lys Asn Ile Ile Thr Ser Ile Thr Ser Leu Ala Leu Val Ala
1               5                   10                  15

Gly Leu Ser Leu Thr Ala Phe Ala Ala Thr Thr Ala Thr Val Pro Ala
                20                  25                  30

Pro Pro Ala Lys Gln Glu Ser Lys Pro Ala Val Ala Ala Asn Pro Ala
                35                  40                  45

Pro Lys Asn Val Leu Phe Gln Tyr Ser Thr Ile Asn Ala Leu Met Leu
                50                  55                  60

Gly Gln Phe Glu Gly Asp Leu Thr Leu Lys Asp Leu Lys Leu Arg Gly
```

```
                65                  70                  75                  80
Asp Met Gly Leu Gly Thr Ile Asn Asp Leu Asp Gly Glu Met Ile Gln
                    85                  90                  95

Met Gly Thr Lys Phe Tyr Gln Ile Asp Ser Thr Gly Lys Leu Ser Glu
                100                 105                 110

Leu Pro Glu Ser Val Lys Thr Pro Phe Ala Val Thr Thr His Phe Glu
                115                 120                 125

Pro Lys Glu Lys Thr Thr Leu Thr Asn Val Gln Asp Tyr Asn Gln Leu
            130                 135                 140

Thr Lys Met Leu Glu Glu Lys Phe Glu Asn Lys Asn Val Phe Tyr Ala
145                 150                 155                 160

Val Lys Leu Thr Gly Thr Phe Lys Met Val Lys Ala Arg Thr Val Pro
                165                 170                 175

Lys Gln Thr Arg Pro Tyr Pro Gln Leu Thr Glu Val Thr Lys Lys Gln
            180                 185                 190

Ser Glu Phe Glu Phe Lys Asn Val Lys Gly Thr Leu Ile Gly Phe Tyr
                195                 200                 205

Thr Pro Asn Tyr Ala Ala Leu Asn Val Pro Gly Phe His Leu His
            210                 215                 220

Phe Ile Thr Glu Asp Lys Thr Ser Gly Gly His Val Leu Asn Leu Gln
225                 230                 235                 240

Phe Asp Asn Ala Asn Leu Glu Ile Ser Pro Ile His Glu Phe Asp Val
                245                 250                 255

Gln Leu Pro His Thr Asp Asp Phe Ala His Ser Asp Leu Thr Gln Val
            260                 265                 270

Thr Thr Ser Gln Val His Gln Ala Glu Ser Glu Arg Lys
            275                 280                 285

<210> SEQ ID NO 36
<211> LENGTH: 278
<212> TYPE: PRT
<213> ORGANISM: Pyrococcus furiosus

<400> SEQUENCE: 36

Met Lys Arg Val Asn Ala Phe Asn Asp Leu Lys Arg Ile Gly Asp Asp
1               5                   10                  15

Lys Val Thr Ala Ile Gly Met Gly Thr Trp Gly Ile Gly Gly Arg Glu
                20                  25                  30

Thr Pro Asp Tyr Ser Arg Asp Lys Glu Ser Ile Glu Ala Ile Arg Tyr
            35                  40                  45

Gly Leu Glu Leu Gly Met Asn Leu Ile Asp Thr Ala Glu Phe Tyr Gly
        50                  55                  60

Ala Gly His Ala Glu Glu Ile Val Gly Glu Ala Ile Lys Glu Phe Glu
65                  70                  75                  80

Arg Glu Asp Ile Phe Ile Val Ser Lys Val Trp Pro Thr His Phe Gly
                85                  90                  95

Tyr Glu Glu Ala Lys Lys Ala Ala Arg Ala Ser Ala Lys Arg Leu Gly
                100                 105                 110

Thr Tyr Ile Asp Leu Tyr Leu Leu His Trp Pro Val Asp Asp Phe Lys
            115                 120                 125

Lys Ile Glu Glu Thr Leu His Ala Leu Glu Asp Leu Val Asp Glu Gly
        130                 135                 140

Val Ile Arg Tyr Ile Gly Val Ser Asn Phe Asn Leu Glu Leu Leu Gln
145                 150                 155                 160
```

Arg Ser Gln Glu Val Met Arg Lys Tyr Glu Ile Val Ala Asn Gln Val
                165                 170                 175

Lys Tyr Ser Val Lys Asp Arg Trp Pro Glu Thr Thr Gly Leu Leu Asp
            180                 185                 190

Tyr Met Lys Arg Glu Gly Ile Ala Leu Met Ala Tyr Thr Pro Leu Glu
        195                 200                 205

Lys Gly Thr Leu Ala Arg Asn Glu Cys Leu Ala Lys Ile Gly Glu Lys
    210                 215                 220

Tyr Gly Lys Thr Ala Ala Gln Val Ala Leu Asn Tyr Leu Ile Trp Glu
225                 230                 235                 240

Glu Asn Val Val Ala Ile Pro Lys Ala Ser Asn Lys Glu His Leu Lys
                245                 250                 255

Glu Asn Phe Gly Ala Met Gly Trp Arg Leu Ser Glu Glu Asp Arg Glu
            260                 265                 270

Met Ala Arg Arg Cys Val
        275

<210> SEQ ID NO 37
<211> LENGTH: 175
<212> TYPE: PRT
<213> ORGANISM: Lactobacillus brevis

<400> SEQUENCE: 37

Met Ser Glu Ile Asp Asp Leu Val Ala Lys Ile Val Gln Gln Ile Gly
1               5                   10                  15

Gly Thr Glu Ala Ala Asp Gln Thr Thr Ala Thr Pro Thr Ser Thr Ala
            20                  25                  30

Thr Gln Thr Gln His Ala Ala Leu Ser Lys Gln Asp Tyr Pro Leu Tyr
        35                  40                  45

Ser Lys His Pro Glu Leu Val His Ser Pro Ser Gly Lys Ala Leu Asn
    50                  55                  60

Asp Ile Thr Leu Asp Asn Val Leu Asn Asp Ile Lys Ala Asn Asp
65                  70                  75                  80

Leu Arg Ile Thr Pro Asp Thr Leu Arg Met Gln Gly Glu Val Ala Asn
                85                  90                  95

Asp Ala Gly Arg Asp Ala Val Gln Arg Asn Phe Gln Arg Ala Ser Glu
            100                 105                 110

Leu Thr Ser Ile Pro Asp Arg Leu Leu Glu Met Tyr Asn Ala Leu
        115                 120                 125

Arg Pro Tyr Arg Ser Thr Lys Ala Glu Leu Leu Ala Ile Ser Ala Glu
    130                 135                 140

Leu Lys Asp Lys Tyr His Ala Pro Val Asn Ala Gly Trp Phe Ala Glu
145                 150                 155                 160

Ala Ala Asp Tyr Tyr Glu Ser Arg Lys Lys Leu Lys Gly Asp Asn
                165                 170                 175

<210> SEQ ID NO 38
<211> LENGTH: 239
<212> TYPE: PRT
<213> ORGANISM: Lactobacillus brevis

<400> SEQUENCE: 38

Met Ala Gln Glu Ile Asp Glu Asn Leu Leu Arg Asn Ile Ile Arg Asp
1               5                   10                  15

Val Ile Ala Glu Thr Gln Thr Gly Asp Thr Pro Ile Ser Phe Lys Ala
            20                  25                  30

-continued

```
Asp Ala Pro Ala Ala Ser Ser Ala Thr Thr Ala Thr Ala Ala Pro Val
            35                  40                  45

Asn Gly Asp Gly Pro Glu Pro Glu Lys Pro Val Asp Trp Phe Lys His
 50                  55                  60

Val Gly Val Ala Lys Pro Gly Tyr Ser Arg Asp Glu Val Val Ile Ala
 65                  70                  75                  80

Val Ala Pro Ala Phe Ala Glu Val Met Asp His Asn Leu Thr Gly Ile
                 85                  90                  95

Ser His Lys Glu Ile Leu Arg Gln Met Val Ala Gly Ile Glu Glu Glu
             100                 105                 110

Gly Leu Lys Ala Arg Ile Val Lys Val Tyr Arg Thr Ser Asp Val Ser
         115                 120                 125

Phe Cys Gly Ala Glu Gly Asp His Leu Ser Gly Ser Gly Ile Ala Ile
 130                 135                 140

Ala Ile Gln Ser Lys Gly Thr Thr Ile Ile His Gln Lys Asp Gln Glu
 145                 150                 155                 160

Pro Leu Ser Asn Leu Glu Leu Phe Pro Gln Ala Pro Val Leu Asp Gly
                 165                 170                 175

Asp Thr Tyr Arg Ala Ile Gly Lys Asn Ala Ala Glu Tyr Ala Lys Gly
             180                 185                 190

Met Ser Pro Ser Pro Val Pro Thr Val Asn Asp Gln Met Ala Arg Val
         195                 200                 205

Gln Tyr Gln Ala Leu Ser Ala Leu Met His Ile Lys Glu Thr Lys Gln
 210                 215                 220

Val Val Met Gly Lys Pro Ala Glu Gln Ile Glu Val Asn Phe Asn
225                 230                 235

<210> SEQ ID NO 39
<211> LENGTH: 558
<212> TYPE: PRT
<213> ORGANISM: Lactobacillus brevis

<400> SEQUENCE: 39

Met Lys Arg Gln Lys Arg Phe Glu Glu Leu Glu Lys Arg Pro Ile His
  1               5                  10                  15

Leu Asp Gly Phe Val Lys Glu Trp Pro Glu Glu Gly Phe Val Ala Met
                 20                  25                  30

Met Gly Pro Asn Asp Pro Lys Pro Ser Ile Lys Ile Glu Asn Gly Lys
             35                  40                  45

Val Thr Glu Met Asp Ser Lys Pro Ala Ala Asp Phe Asp Leu Ile Asp
 50                  55                  60

Leu Tyr Ile Ala Lys Tyr Gly Ile Lys Leu Glu Asn Ala Glu Lys Val
 65                  70                  75                  80

Met Ala Met Asp Ser Thr Lys Ile Ala Asn Met Leu Cys Asp Pro Asn
                 85                  90                  95

Val Pro Arg Lys Asp Ile Ile Glu Ile Thr Thr Ala Met Thr Pro Ala
             100                 105                 110

Lys Ala Glu Glu Val Ile Ser Lys Leu Asn Phe Ala Glu Met Ile Met
         115                 120                 125

Ala Thr Gln Lys Met Arg Pro Arg Arg Thr Pro Ala Thr Gln Cys His
 130                 135                 140

Val Thr Asn Ile Arg Asp Asn Pro Val Gln Ile Ala Ala Asp Ala Ala
 145                 150                 155                 160

Asp Ala Ala Leu Arg Gly Phe Pro Glu Gln Glu Thr Thr Thr Ala Val
                 165                 170                 175
```

```
Ala Arg Tyr Ala Pro Leu Asn Ala Ile Ser Leu Met Val Gly Ala Gln
            180                 185                 190

Thr Gly Arg Pro Gly Val Ile Thr Gln Cys Ser Val Glu Glu Ala Glu
            195                 200                 205

Glu Leu Ser Leu Gly Met Arg Gly Phe Thr Gly Tyr Ala Glu Thr Ile
    210                 215                 220

Ser Val Tyr Gly Thr Asp Lys Val Phe Thr Asp Gly Asp Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ser Gly Ser Glu Val Met Met Gly Tyr Thr
            260                 265                 270

Glu Gly Lys Ser Met Leu Tyr Leu Glu Ser Arg Cys Ile Phe Ile Thr
            275                 280                 285

Lys Ala Ser Gly Val Gln Gly Leu Gln Asn Gly Gly Val Ser Cys Ile
            290                 295                 300

Gly Ile Pro Gly Ser Val Pro Ser Gly Ile Arg Ser Val Leu Gly Glu
305                 310                 315                 320

Asn Leu Leu Cys Met Met Leu Asp Leu Glu Cys Ala Ser Ala Asn Asp
                325                 330                 335

Gln Ala Phe Ser His Ser Asp Met Arg Arg Thr Glu Arg Leu Leu Gly
            340                 345                 350

Gln Phe Ile Ala Gly Thr Asp Tyr Ile Ser Ser Gly Tyr Ser Ser Thr
            355                 360                 365

Pro Asn Tyr Asp Asn Thr Phe Ala Gly Ser Asn Thr Asp Gly Leu Asp
            370                 375                 380

Tyr Asp Asp Tyr Tyr Val Met Glu Arg Asp Leu Ala Ile Asn Gly Gly
385                 390                 395                 400

Ile His Pro Val Asp Glu Gln Thr Ile Ile Lys Ala Arg Asn Lys Ala
                405                 410                 415

Ala Arg Ala Leu Gln Gly Val Phe Glu Asp Leu Gly Leu Pro Lys Ile
            420                 425                 430

Thr Asp Glu Glu Val Glu Ala Ala Thr Tyr Ala Asn Thr Ser Lys Asp
            435                 440                 445

Met Pro Glu Arg Asn Met Val Glu Asp Met Lys Ala Ala Gln Asp Leu
    450                 455                 460

Met Asp Arg Gly Ile Thr Gly Val Asp Ile Val Lys Ala Leu Phe Asn
465                 470                 475                 480

His Gly Phe Lys Asp Val Ala Gln Ala Val Leu Asp Leu Gln Lys Gln
                485                 490                 495

Lys Val Cys Gly Asp Phe Leu Gln Thr Ser Ala Ile Phe Asp Ser Lys
                500                 505                 510

Trp His Val Ile Ser Ala Val Asn Asp Ala Asn Asp Tyr Gln Gly Pro
            515                 520                 525

Gly Thr Gly Tyr Arg Leu Glu Glu Asp Thr Glu Glu Trp Glu Arg Ile
            530                 535                 540

Lys Asn Leu Pro Phe Ala Ile Asp Pro Gln Asn Met Gln Leu
545                 550                 555
```

US 8,859,247 B2

PROCESS FOR CELL-FREE PRODUCTION OF CHEMICALS

RELATED APPLICATIONS

This application is a 35 U.S.C. §371 national stage filing of International Application No. PCT/EP2009/067954, filed Dec. 28, 2009, which is related and claims priority to EP Application Serial No.: 08 022 558.4, filed 30 Dec. 2008. The entire contents of these applications are explicitly incorporated herein by reference.

SUMMARY OF INVENTION

An enzymatic process is described for the production of chemicals from carbon sources. In particular, according to one aspect, a process for the production of a target organic compound from a carbon source by a cell-free enzyme system is disclosed.

BACKGROUND OF THE INVENTION

The invention is directed to a process for the bioconversion of a carbon source, which is preferably a carbohydrate or another carbon containing compound into a target organic compound by an enzymatic process, preferably in the absence of productive living cells. The target organic compound is preferably a hydrophobic, a hydrophilic or an intermediate chemical compound.

Hydrophobic chemicals according to the invention comprise, without limitation, C4 alcohols such as n-butanol, 2-butanol, and isobutanol, and other chemicals that have a limited miscibility with water. Limited miscibility means that at room temperature not more than 20% (w/w) can be mixed with water without phase separation. Hydrophilic and intermediate chemicals according to the invention comprise, without limitation ethanol and other chemicals.

n-Butanol is a colorless, neutral liquid of medium volatility with restricted miscibility (about 7-8% at RT) in water. n-Butanol is used as an intermediate in the production of chemicals, as a solvent and as an ingredient in formulated products such as cosmetics. n-Butanol is used in the synthesis of acrylate/methacrylate esters, glycol ethers, n-butyl acetate, amino resins and n-butylamines. n-Butanol can also be used as a fuel in combustion engines due to low vapor pressure, high energy content and the possibility to be blended with gasoline at high concentrations.

2-Butanol is a colorless, neutral liquid of medium volatility with restricted miscibility (about 12% at RT) in water. 2-Butanol is used as solvent for paints and coatings as well as food ingredients or in the production of 1-butene.

Isobutanol is a colorless, neutral liquid of medium volatility with restricted miscibility (about 9-10% at RT) in water. Isobutanol is used as solvent or as plasticizer. It is also used in the production of isobutene which is a precursor for the production of MTBE or ETBE.

n-Butanol can be produced using solventogenic *Clostridia*, such as *C. acetobuylicum* or *C. beijerinckii*, typically producing a mixture of n-butanol, acetone and ethanol. Butanol production using solventogenic *clostridia* has several drawbacks: (i) Product isolation from dilute aqueous solution is very expensive as it is either elaborate (e.g. using membrane processes) or energy consuming (e.g. using distillation). (ii) The yield is low as significant parts of the substrate go into the formation of by-products such as acetone, ethanol, hydrogen and biomass. (iii) The productivity of butanol production is low due to limited cell titres. (iv) The complex metabolism limits metabolic engineering for higher productivity and yield. (v) Limited process stability often leads to production losses and sterility is difficult to maintain. (vi) The biphasic nature of clostridial growth limits process flexibility and productivity.

Several approaches exist to overcome the limitations of classical fermentative butanol production. For example, WO2008/052596 describes recombinant modification of *Clostridia* for improved yield. Selection or engineering of variants for higher Butanol resistance is, for example, described in WO 2008/006038.

The cell-free production of chemicals has been shown as early as 1897 when Eduard Buchner used a lysate of yeast cells to convert glucose to ethanol. Later Welch and Scopes, 1985 demonstrated cell free production of ethanol, a process which, however, was technically not useful. The system lacked specificity (side reaction of enzymes, unwanted activities in the lysate) and a maximum of 9% ethanol was obtained.

A number of technical processes have been described that use isolated enzymes for the production of chemicals. For example, alcohol dehydrogenases are used in the production of chiral alcohols from ketones. Such processes require cofactor (NAD) regeneration which can be achieved, for example, by adding glucose and glucose dehydrogenase. Such processes have been designed to produce high-value chemicals but not to provide enzyme system comprising multiple enzyme reactions that convert carbohydrates into chemicals with high energy and carbon efficiency.

Zhang et al., 2008 describe the idea for cell free enzymatic conversion of glucose to n-butanol. The concept includes a minimum of 18 enzymes, several different cofactors and coenzymes (e.g. ATP, ADP, NADH, NAD, ferredoxin and coenzyme A). In addition the postulated process results in a net-production of ATP so that it requires in addition an ATPase enzyme to remove the ATP. Under practical terms control of ATPase addition while maintaining a balanced ATP level is very difficult to achieve. In summary, the described process would be expensive, technically instable and would give only low butanol yields.

In summary there is a need for a cost effective process for the production of chemicals from renewable resources, in particular ethanol and C4 alcohols such as n-butanol and its isomers.

According to one aspect, the present invention addresses this need through a cell free enzymatic system, using only a limited number of enzymes and a limited set of cofactors. In particular, according to a preferred aspect, the inventive process does not lead to net ATP production, and/or does not use phosphorylative enzyme reactions, and/or uses only enzymes that withstand the inactivating presence of the produced chemicals.

DEFINITIONS

A hydrophobic chemical is a chemical which is only partially soluble in water and which resides in the solid or liquid state at ambient pressure and temperature. Hydrophobic chemicals have a limited miscibility with water of not more than 20% (w/w) without phase separation. Particular examples of hydrophobic chemicals according to the present invention include n-butanol, 2-butanol and isobutanol.

Carbon source can be any material which can be utilized by microorganisms for growth or production of chemicals. These include carbohydrates and derivatives: polyoses such as cellulose, hemicellulose, starch; bioses such as sucrose, maltose, lactose; hexoses such as glucose, mannose, galactose; pentoses such as xylose, arabinose; uronic acids, glucosamines etc.; polyols such as sorbitol, glycerol; lipids and derivatives, lignin and derivatives.

Particularly preferred carbon sources are glucose, a glucose-containing oligomer or polymer, a non-glucose monomeric hexose, or a polymeric sugar derivative, or mixtures thereof.

DETAILED DESCRIPTION OF INVENTION

The present invention is directed to a cell-free process for the biotechnological production of chemicals from carbon sources, in particular of hydrophobic chemicals such as C4 alcohols including n-butanol, isobutanol or 2-butanol, and of hydrophilic and intermediate chemicals such as ethanol.

According to a preferred aspect, the invention discloses and claims a process for the production of a target organic compound from a carbon source by a cell-free enzyme system, comprising the conversion of glucose to pyruvate as an intermediate product wherein no net production of ATP occurs. Preferably, no net production of ATP occurs in the conversion of glucose to pyruvate as an intermediate product. More preferably, no production of ATP occurs in the overall conversion of the carbon source to the target organic compound.

According to a preferred aspect, the carbon source compound is glucose, a glucose-containing oligomer or polymer, a non-glucose monomeric hexose, or a polymeric sugar derivative.

According to a further preferred aspect, the target organic compound is ethanol, a four-carbon mono-alcohol, in particular n-butanol, iso-butanol, 2-butanol, or another organic compound derivable from pyruvate, preferably by an enzymatic pathway.

According to a preferred embodiment of the invention, the conversion of glucose to pyruvate as an intermediate product works completely without ATP and/or ADP as cofactors. More preferably, the overall conversion of the carbon source to the target organic compound (the reaction pathway) works completely without ATP and/or ADP as cofactors.

According to a further preferred embodiment of the invention and as further described herein, the production process is performed in a liquid system comprising two separate phases, and the target organic compound is mainly present in or forms one of the separate phases, and the target organic compound is collected from the separate phase.

According to a further preferred embodiment of the invention and as further described herein, an organic solvent is added to establish the two separate phases.

According to a further preferred embodiment of the invention and as further described herein, the carbon source compound is continuously fed to the process and the target organic compound is continuously removed.

According to a further preferred embodiment of the invention and as further described herein, the enzyme system comprises the following enzymes or enzyme activities, preferably for the conversion from glucose to pyruvate:
  glucose dehydrogenase (EC 1.1.1.47),
  gluconolactonase (EC 3.1.1.17),
  gluconate dehydratase (EC 4.2.1.39),
  2-keto-3-deoxy gluconate aldolase (EC 4.1.2.14),
  aldehyde dehydrogenase (EC 1.2.1.3),
  glycerate dehydrogenase (EC 1.1.1.29) or Hydroxypyruvate reductase (EC 1.1.1.81),
  serine-pyruvate transaminase (EC 2.6.1.51),
  L-serine ammonia-lyase (EC 4.3.1.17) and
  alanine dehydrogenase (EC 1.4.1.1).

According to a further preferred embodiment of the invention and as further described herein, the enzyme system comprises the following enzymes or enzyme activities, preferably for the conversion from glucose to pyruvate:
  glucose dehydrogenase (EC 1.1.1.47),
  gluconolactonase (EC 3.1.1.17),
  gluconate dehydratase (EC 4.2.1.39)
  2-keto-3-deoxy gluconate aldolase (EC 4.1.2.14)
  aldehyde dehydrogenase (EC 1.2.1.3) and
  glycerate dehydratase (EC 4.2.1.).

According to a further preferred embodiment of the invention and as further described herein, ethanol is produced from glucose by an enzyme system comprising 11, 10, 9, 8, 7 or less enzymes.

According to a further preferred embodiment of the invention and as further described herein, n-butanol is produced from glucose by an enzyme system comprising 17, 16, 15 or less enzymes.

According to a further preferred embodiment of the invention and as further described herein, iso-butanol is produced by an enzyme system comprising 14, 13 or less enzymes.

According to a further preferred embodiment of the invention and as further described herein, 2-butanol is produced by an enzyme system comprising 13 or less enzymes.

According to one preferred aspect, the inventive production process comprises the following 4 steps:
  I. Production of enzymes (the "target enzymes") for the conversion of a carbon source into a chemical (also herein referred to as the "target chemical" or "target organic compound") using microbial cells;
  II. Release of the target enzymes from the microbial cells used in step I, preferably combined with release of cofactors and with inactivation of further, non-target enzyme activities;
  III. Bringing the target enzymes of step II in contact with the carbon source under conditions suitable for the conversion of the carbon source into the target chemical;
  IV. Separating the target chemical from the reaction mixture.

FIG. 1 further illustrates a possible implementation of the concept of the invention according to a preferred embodiment.

Step I:
In step I the target enzymes are produced using microbial cells.

In one embodiment of the invention, enzyme production is done in two or more different microbial cell lines, such that the entire production route or major parts of it are not reconstituted in one microorganism. This avoids the unwanted initiation of substrate conversion towards the chemical and leads to a more efficient enzyme production. Enzyme production can be intracellular or extracellular, recombinant or non-recombinant. If enzyme production is recombinant it can be homologous or heterologous.

In a further embodiment of the invention, the target enzymes are selective for one substrate and one reaction. Preferably, the target enzymes have a substrate selectivity (kcat/kM) of at least 10 fold compared to any other naturally present substance and a reaction selectivity of at least 90%. More preferably, the target enzymes have a substrate selectivity of at least 20 fold and a reaction selectivity of at least 95%. Even more preferably, the target enzymes have a substrate selectivity of at least 100 fold and a reaction selectivity of at least 99%.

In a further embodiment of the invention, the target enzymes show no or low inhibition by the substrate or the product or other intermediates of the multistep reaction (no or low feedback inhibition). Preferably, the inhibition constants ($K_i$) for any substrate, product or intermediate of the multistep reaction are at least 10 fold higher than the $K_M$ value for the respective enzyme and substrate. More preferably, such inhibition constants are 100 fold higher than the respective $K_M$. In a further, particularly preferred embodiment the target enzymes still have 50% of their maximum activity at concentrations of any substrate, intermediate or product of the multistep reaction of 100 mM or more.

Preferably, the target enzymes have $k_{cat}$ and $K_M$ values that are adjusted to the multistep nature of the enzymatic route.

According to one embodiment of the process of the invention, the target enzymes tolerate elevated levels of the target chemical and, optionally, other organic solvents that are optionally added to support segregation of the target chemical into a separate phase. Preferably the target enzymes tolerate concentrations of the target chemical of more than 2 wt %, more preferably more than 6 wt %, and most preferably more than 12 wt %. In a particularly preferred embodiment, the target enzymes tolerate concentrations of the target chemicals up to the maximum solubility in water.

In a preferred embodiment of the invention, the target enzymes tolerate elevated levels of chaotropic substances and elevated temperatures. Preferably, the target enzymes tolerate concentrations of guanidinium chloride of more than 1 M, more preferably more than 3 M, and most preferably more than 6 M. Alternatively or in combination, the target enzymes tolerate preferably temperatures of more than 50° C., more preferably more than 70° C., and most preferably more than 90° C. In such preferred embodiment, target enzyme production is done in a host organism whose endogenous enzyme activities are mostly inactivated at elevated levels of chaotropic substances and/or at elevated temperatures. Preferably target enzyme production is done using of the following microbial species: *Escherichia coli; Pseudomonas fluorescence; Bacillus subtilis; Saccharomyces cerevisiae; Pichia pastoris; Hansenula polymorpha; Klyuveromyces lactis; Trichoderma reesei; Aspergillus niger*. More preferably target enzyme production is done using *Escherichia coli* as host organism.

In a further preferred embodiment of the invention, the target enzymes tolerate elevated levels of oxygen. Preferably, the target enzymes tolerate oxygen concentrations of more than 1 ppm, more preferably more than 7 ppm. Most preferably the target enzymes are active and stable under aerobic conditions. Preferably, the multistep reaction does not require oxygen and is not inhibited by oxygen. Thereby, no special precautions for oxygen exclusion have to be taken, making the process more stable with less effort on the production environment and/or equipment.

Preferably, enzyme production and cell growth are separated into separate phases. Thereby, no substrate is used for general metabolic activity.

Step II:

In step II the target enzymes are released from the cells.

In a preferred embodiment, the target enzymes tolerate high temperatures and chaotropic conditions, whereas the background enzymes from the producing microorganism do not tolerate these conditions. According to this embodiment, the target enzymes are produced intracellularly in microbial cells, the cells are lysed using high temperature and/or chaotropic conditions, thereby releasing the target enzymes in active form, optionally together with cofactors, while unwanted background enzyme activities are inactivated.

In another preferred embodiment, enzyme production is extracellular, the target enzymes tolerate high temperatures and chaotropic conditions, and background enzyme activities (non-target enzymes) do not tolerate these conditions. According to this embodiment, the supernatant from extracellular production is treated under conditions such as high temperatures and/or chaotropic conditions. This leads to inactivation of unwanted background enzyme activities (non-target enzymes) while the target enzymes remain active.

In one embodiment of the invention, cofactors are required for one or more of the multiple enzymatic conversion steps. In one aspect of the invention such cofactors are added to the enzyme mixture. In another, particularly preferred aspect of this embodiment such cofactors are also produced by the microbial cells intracellularly and are released by the same treatment as to release the target enzymes. In another preferred embodiment of the invention, the microbial cells are engineered in order to optimize the level of cofactors produced.

Preferably, the microbial cells are inactivated during step II. Thereby, cell growth and enzyme activity are separated in the process, and no carbon source is consumed by undesirable cell growth.

Step III:

In step III the carbon source is converted by a mixture of enzymes in a multistep enzymatic reaction to the target chemical.

According to the inventive process, the enzymes are active under the denaturing activity of the target chemical. Preferably, the microbial cells used in step I are inactive and/or are inactivated under the reaction conditions of step III.

Preferably, the concentration of each enzyme in the target enzyme mixture is adjusted to the optimal level under process conditions. In a particularly preferred embodiment one or more enzyme concentrations are increased above typical intracellular concentrations in order to improve the yield of the process (no limit by the maximal density of the microorganisms as in classical processes). In another particularly preferred embodiment, one or more enzymes are engineered for maximal catalytic efficiency (leading to lower reactor size and running costs compared to classical processes).

In a further preferred embodiment, the target chemical is added to the reaction mixture in step III at a concentration just above the maximum level that can be mixed in a single phase with water under process conditions. According to this embodiment, the target chemical continuously segregates into the second phase during the process. In a particular variant of this embodiment, a water soluble substance is added to the reaction mixture that leads to a phase separation of the target chemical at lower concentration than without the added substance. Examples of such substances are salts and are known to the person skilled in the art. In a particularly preferred variant of this embodiment, sodium chloride is added to lower the solubility of the target chemical in the water phase.

In another preferred embodiment, an additional organic solvent is added to the process that forms its own phase and extracts the produced hydrophobic chemical from the water phase. Preferred examples of such additional solvents comprise: n-hexane, cyclohexane, octanol, ethyl acetate, methyl butyl ketone or combinations thereof.

In another preferred embodiment, the yield is improved because the formation of side products is decreased by using target enzymes that are specific for the desired reactions. In another preferred embodiment, host enzymes that would catalyse side reactions are inactivated during step II and/or are inactive under the reaction conditions of step III.

In yet another preferred embodiment of the invention, contamination of the process by microorganisms is avoided by adjusting reaction conditions in step III that are toxic for typical microbial contaminants. Such conditions comprise elevated temperature, extreme pH, addition of organic chemicals. In a particularly preferred embodiment of the invention, the target chemical itself is toxic at the concentration achieved in the process (more stable process with less effort on production environment and/or equipment).

According to another preferred embodiment to the invention, no additional cofactors are added to the reaction mixture except for those cofactors that are produced by the microorganisms used in step I and that are included in the cell lysate produced in step II. Examples of such cofactors are NAD/NADH, NADP/NADPH, ATP/ADP. According to this embodiment, the cofactors that are required are produced by the microbial cells in step I and are regenerated during the process (NADH to NAD and vice versa; NADPH to NADP and vice versa, ADP to ATP and vice versa). In one embodiment of the invention, excess reduction equivalents (NADH, NADPH) or energy equivalents (ATP) are regenerated by additional enzymes (NADH oxidase for NADH; NADPH oxidase for NADPH; ATPase for ATP).

In a particularly preferred embodiment of the invention, neither ATP nor ADP is involved as a cofactor in at least a substantial part of the multistep reaction process. A substantial part of the multistep reaction pathway comprises preferably at least 20% of the enzyme activities, and more preferably at least 50% of the enzyme activities. Most preferably, none of the enzyme activities of the target enzyme mixture (the enzyme mixture produced in step I) comprises a phosphorylation step (non-phosphorylative reaction pathway). In a particularly preferred embodiment of the invention the reaction pathway involves the conversion from glucose to pyruvate and none of the target enzymes involved in this conversion comprises a phosphorylation step (non-phosphorylative pyruvate production).

Step IV:

In step IV, the one or more target chemicals are separated from the reaction mixture.

In a preferred embodiment of the invention the one or more target chemicals are hydrophobic and form a separate phase which preferably contains at least a substantial fraction of the produced chemicals. In a particularly preferred embodiment the one or more target chemicals are continuously removed from the reaction mixture.

In a further preferred embodiment of the invention, the carbon source is continuously fed to the reaction mixture to be converted into the target chemical. Likewise, the target chemical is preferably continuously removed as a separate phase and further purified by methods known in the art. Thereby, product isolation is simplified as the product is collected in a separate phase from which it can be purified further. Thereby, the yield is improved and product purification is simplified.

A major problem of the described cell free enzymatic processes (Zhang et al., 2008, Welch and Scopes 1985) is the accumulation of ATP. In the described processes this is circumvented by the addition of an ATPase. To find the right concentration of ATPase, however, is difficult as it depends on the concentration of the substrate and different intermediates as well as on the activity of the enzymes. With either too much ATPase or too little ATPase the conversion completely ceases (Welch and Scopes, 1985). In contrast, according to a particularly preferred aspect, the inventive cell-free process converts a carbon source such as glucose and its polymers to a target chemical such as ethanol, butanol and/or isobutanol without net production of ATP and without using an ATPase.

In a further preferred embodiment, the inventive process does not require ADP or ATP as cofactors. Other processes (Welch and Scopes, 1985; Algar and Scopes, 1985) require cofactors such as ADP/ATP and NAMNADH. The postulated conversion of glucose to Butanol (Zhang et al, 2008) requires the cofactors ADP/ATP, $NAD^+$/NADH, Ferredoxin and Coenzyme A.

As used herein, the term "enzyme" encompasses also term "enzyme activity" and may be used interchangeably.

Several preferred embodiments are hereinafter described regarding the production of n-butanol, isobutanol, ethanol and 2-butanol.

Production of n-Butanol

In one embodiment of the invention, the target chemical is n-butanol and the target enzyme mixture to produce n-butanol comprises less than 19 different enzyme activities. Preferably the target enzyme mixture comprises 17 or less different enzyme activities, more preferably 16 or less enzyme activities, even more preferably 15 or less enzyme activities, and most preferably only 12 different enzyme activities. Because production of enzymes is a major cost factor in the process this gives a major advantage over other processes.

In a particularly preferred embodiment, n-butanol is produced from glucose via the intermediates pyruvate and acetyl CoA. The production of n-butanol from glucose can be arbitrarily subdivided into three steps: (A) Conversion of one molecule glucose to two molecules of pyruvate. (B) Conversion of two molecules pyruvate to two molecules acetyl CoA. (C) Conversion of two molecules acetyl CoA to one molecule n-butanol.

Step (A): Conversion of Glucose to Pyruvate.

This step is common in most if not all organisms, even though different metabolic pathways exist (e.g. Embden-Meyerhof-Parnas way, Entner-Doudoroff-Way). A particular variant of step (A) uses enzymes from the Embden-Meyerhof-Parnas way, comprising the 10 enzyme activities as listed in Tab. 1 (enzyme combination A.1). The reaction pathway catalysed by this enzyme combination includes phosphorylating enzymes and leads to net ATP production (2 molecules ATP are generated per molecule glucose).

TABLE 1

Enzyme combination A.1, comprising enzymes from the Embden-Meyerhof-Parnas way

| # | Enzyme | EC # | Substrate | Product |
|---|--------|------|-----------|---------|
| 1 | Hexokinase | 2.7.1.1 | Glukose | Glukose-6-Phosphate |
| 2 | Phosphohexoisomerase | 5.3.1.9 | Glucose 6 Phosphate | Fruktose-6-Phosphate |
| 3 | Phosphofruktokinase | 2.7.1.11 | Fruktose-6-Phosphate | Fruktose-1,6-Bisphosphate |
| 4 | Aldolase | 4.1.2.13 | Fruktose-1,6-Bisphosphate | Glyceraldehyd-3-Phosphate, Dihydroxyaceton-phosphate |
| 5 | Phosphotrioseisomerase | 5.3.1.1 | Dihydroxyaceton-phosphate | Glyceraldehyd-3-Phosphate |
| 6 | Glycerinaldehyd-3-phosphat-Dehydrogenase | 1.2.1.12 | Glyceraldehyd-3-Phosphate | Glycerate-1,3 Bisphosphate |
| 7 | Phosphoglyceratkinase | 2.7.2.3 | Glycerate-1,3 Bisphosphate | Glycerate-3-Phosphate |

TABLE 1-continued

Enzyme combination A.1, comprising enzymes from the Embden-Meyerhof-Parnas way

| # | Enzyme | EC # | Substrate | Product |
|---|---|---|---|---|
| 8 | Phosphoglyceratmutase | 5.4.2.1 | Glycerate-3-Phosphate | Glycerate-2-Phosphate |
| 9 | Enolase | 4.2.1.11 | Glycerate-2-Phosphate | Phosphoenolpyruvate |
| 10 | Pyruvatkinase | 2.7.1.40 | Phosphoenolpyruvate | Pyruvate |

Another particular variant of step (A) uses enzyme activities of the Entner-Doudoroff pathway. According to a preferred embodiment of the invention, enzymes from the non-phosphorylative Entner-Doudoroff pathway known from archaea are used in step (A). This comprises the 8 enzyme activities listed in Tab. 2 (enzyme combination A.2). This enzyme combination comprises phosphorylating enzymes and, therefore, requires ATP and/or ADP as cofactors, but the conversion of glucose to pyruvate does not lead to net production of ATP.

TABLE 2

Enzyme combination A.2, comprising enzymes from the non-phosphorylative Entner-Doudoroff pathway

| # | Enzyme | EC # | Substrate | Product |
|---|---|---|---|---|
| 1 | Glucose dehydrogenase | 1.1.1.47 | Glukose | Glukonolactone |
| 2 | Gluconolactonase | 3.1.1.17 | Glukonolactone | Glukonate |
| 3 | Gluconate dehydratase | 4.2.1.39 | Glukonate | 2-keto-3-deoxy gluconate |
| 4 | 2-keto-3-deoxy gluconate aldolase | 4.1.2.14 | 2-keto-3-deoxy gluconate | Pyruvate, Glyceraldehyde |
| 5 | Aldehyde dehydrogenase | 1.2.1.3 | Glyceraldehyde | Glycerate |
| 6 | Phosphoglycerate kinase | 2.7.1._ | Glycerate | Glycerate-2-Phosphate |
| 7 | Enolase | 4.2.1.11 | Glycerate-2-Phosphate | Phosphoenolpyruvate |
| 8 | Pyruvate Kinase | 2.7.1.40 | Phosphoenolpyruvate | Pyruvate |

Another particularly preferred variant of step (A) uses an enzyme combination that neither leads to net production of ATP nor does it require ATP or ADP as cofactors. The respective enzyme combination comprises the 9 different enzyme activities as listed in Tab. 3 (enzyme combination A.3).

TABLE 3

Enzyme combination A.3, comprising enzyme activities from various pathways

| # | Enzyme | EC # | Substrate | Product |
|---|---|---|---|---|
| 1 | Glucose dehydrogenase | 1.1.1.47 | Glukose | Glukonolacton |
| 2 | Gluconolactonase | 3.1.1.17 | Glukonolactone | Glukonate |
| 3 | Gluconate dehydratase | 4.2.1.39 | Glukonate | 2-keto-3-deoxy gluconate |
| 4 | 2-keto-3-deoxy gluconate aldolase | 4.1.2.14 | 2-keto-3-deoxy gluconate | Pyruvate, Glyceraldehyde |
| 5 | Aldehyde dehydrogenase | 1.2.1.3 | Glyceraldehyde | Glycerate |
| 6 | Glycerate dehydrogenase | 1.1.1.29/ 1.1.1.81 | Glycerate | Hydroxypyruvate |
| 7 | Serine-pyruvate transaminase | 2.6.1.51 | Hydroxypyruvate + Alanine | Serine + Pyruvate |
| 8 | L-Serine ammonia-lyase | 4.3.1.17 | Serine | Pyruvate + Ammonia |
| 9 | Alanine dehydrogenase | 1.4.1.1 | Pyruvate + Ammonia | Alanine |

A further, particularly preferred variant of step (A) uses another enzyme combination that also neither leads to net production of ATP nor does it require ATP or ADP as cofactors. The respective enzyme combination comprises the 5 different enzyme activities as listed in Tab. 4 (enzyme combination A.4).

TABLE 4

Enzyme combination A.4, comprising enzyme activities from various pathways

| # | Enzyme | EC # | Substrate | Product |
|---|--------|------|-----------|---------|
| 1 | Glucose dehydrogenase | 1.1.1.47 | Glukose | Glukonolacton |
| 2 | Gluconolactonase | 3.1.1.17 | Glukonolactone | Glukonate |
| 3 | Dihydroxyacid dehydratase (with gluconate dehydratase activity) | 4.2.1.9 | Glukonate | 2-keto-3-deoxy gluconate |
| 4 | 2-keto-3-deoxy gluconate aldolase | 4.1.2.14 | 2-keto-3-deoxy gluconate | Pyruvate, Glyceraldehyde |
| 5 | Aldehyde dehydrogenase | 1.2.1.3 | Glyceraldehyde | Glycerate |
| 6 | Dihydroxyacid dehydratase (with glycerate dehydratase activity) | 4.2.1.9 | Glycerate | Pyruvate |

Step (B): Conversion of Pyruvate to Acetyl CoA

Various options exist for the conversion of pyruvate to acetyl CoA.

In one embodiment of the invention, one or more of the following enzymes is used for the conversion: (i) pyruvate oxidoreductase using ferredoxin as cofactor; (ii) pyruvate dehydrogenase using NAD(P)H as cofactor; (iii) pyruvate formate lyase; (iv) pyruvate dehydrogenase enzyme complex.

In a preferred embodiment, pyruvate dehydrogenase is used as the enzyme for this conversion, using NADH as cofactor (as listed in Tab. 5).

TABLE 5

Enzyme combination B.1

| # | Enzyme | EC # | Substrate | Product |
|---|--------|------|-----------|---------|
| 1 | Pyruvate dehydrogenase | 1.2.1.51 | Pyruvate | Acetyl CoA |

Pyruvate dehydrogenases are usually part of a multi enzyme complex (Pyruvate dehydrogenase complex, PDC) which consists of three enzymatic activities and has a molecular weight of ca. 1 Mio Da. For application in a cell-free reaction system it is beneficial to have small and robust non-complexed enzymes. It has been found that the pyruvate dehydrogenase from *Euglena gracilis* can be used in the enzyme mixture B.1. This enzyme is singular and complex-free. Furthermore it uses NADH as cofactor which is compared to NADPH the more suitable cofactor (available in higher quantities; easier to regenerate).

Alternatively, pyruvate formate lyase can be combined with a formate dehydrogenase using NADH as cofactor.

Step (C): Conversion of Acetyl CoA to n-Butanol

Various options exist for the conversion of acetyl CoA to n-butanol, as several micro-organisms produce n-butanol via this pathway (e.g. *C. acetobutylicum, C. beijerinckii*).

In a preferred variant of step (C), the enzymes as listed in Tab. 6 are used for the conversion. Depending on the enzymes (source organisms) different cofactors are used.

TABLE 6

Enzyme combination C.1 for the conversion of Acetyl CoA to n-Butanol

| # | Enzyme | EC # | Substrate | Product |
|---|--------|------|-----------|---------|
| 1 | Thiolase | 2.3.1.16 | AcetylCoA | AcetoacetylCoA |
| 2 | β-HydroxybutyrylCoA dehydrogenase | 1.1.1.157 | AcetoacetylCoA | β-HydroxybutyrylCoA |
| 3 | Crotonase | 4.2.1.55 | β-HydroxybutyrylCoA | CrotonylCoA |
| 4 | ButyrylCoA Dehydrogenase | 1.3.99.2 | CrotonylCoA | ButyrylCoA |
| 5 | CoA acylating Butanal Dehydrogenase | 1.2.1.57 | Butyrate | Butanal |
| 6 | Butanol Dehydrogenase | 1.1.1.— | Butanal | Butanol |

In another preferred variant the reaction pathway from the intermediate Butyryl CoA to Butanol does not involve butyrate but butyryl phosphate. The listed pathways and the enzymes are not exclusive. Alternative enzymes and routes known in the art can also be used.

When all reaction steps as described above are combined (enzyme combination A.1, A.2, A.3 or A.4; plus enzyme combinations B.1 and C.1) a net conversion of one molecule glucose to two molecules of $CO_2$, one molecule of water and one molecule of n-butanol is achieved. None of the enzyme combinations leads to a net production of reduction equivalents (4 molecules $H_2$ are released and subsequently used again). Depending on the route from glucose to pyruvate none (A.2, A.3 or A.4) or up to 2 molecules of ATP (A.1) are generated from ADP and phosphate.

In a particularly preferred embodiment of the invention, enzyme combinations A.4, B.1 and C.1 are combined. This target enzyme mixture comprises only 12 different enzyme activities, does not require ADP/ATP as cofactor and, consequently, does not lead to a net ATP production.

In another particularly preferred embodiment of the invention, enzyme combinations A.3, B.1 and C.1 are combined. This target enzyme mixture comprises 16 different enzyme activities, does not require ADP/ATP as cofactor and, consequently, does not lead to a net ATP production.

In another preferred embodiment of the invention, enzyme combinations A.2, B.1 and C.1 are combined. This target enzyme mixture comprises 15 different enzyme activities, requires ADP/ATP as cofactors, but does not lead to a net ATP production.

Production of Isobutanol

In another embodiment of the invention the target chemical is isobutanol.

In a particularly preferred embodiment, isobutanol is produced from glucose via the intermediate pyruvate. The production of isobutanol from glucose can be arbitrarily subdivided in two steps: (A) Conversion of one molecule glucose to two molecules pyruvate; and (D) Conversion of two molecules pyruvate to one molecule iso-butanol.

Step (A): Conversion of Glucose to Pyruvate

This step is equivalent to step (A) in the production of n-butanol (see above).

Step (D): Conversion of Pyruvate to Isobutanol

In a preferred embodiment of the invention, the enzyme activities as listed in Table 7 are used in Step (D) for the cell free production of isobutanol.

TABLE 7

Enzyme combination D.1, comprising enzyme activities for the conversion from pyruvate to isobutanol

| # | Enzyme | EC # | Substrate | Product |
|---|---|---|---|---|
| 1 | acetolactate synthase | 2.2.1.6 | Pyruvate | Acetolactate |
| 2 | ketol-acid reductoisomerase | 1.1.1.86 | Acetolactate | 2,3 dihydroxy isovalerate |
| 3 | Dihydroxyacid dehydratase | 4.2.1.9 | 2,3 dihydroxy isovalerate | a-keto-isovalerate |
| 4 | Branched-chain-2-oxo acid decarboxylase | 4.1.1.72 | a-keto-isovalerate | isobutanal |
| 5 | alcohol dehydrogenase | 1.1.1.1 | Isobutanal | isobutanol |

When all reactions as described above are combined (enzyme combinations A.1, A.2, A.3 or A.4; plus enzyme combination D.1) a net conversion of one molecule glucose to two molecules $CO_2$, one molecule water and one molecule isobutanol is achieved. None of the enzyme combinations leads to a net production of reduction equivalents (4 molecules $H_2$ are formed in the formation of two molecules pyruvate and are subsequently used up in the formation of isobutanol). Depending on the route from glucose to pyruvate none (A.2, A.3 or A.4) or up to 2 molecules of ATP (A.1) are generated from ADP and phosphate.

In a particularly preferred embodiment of the invention, enzyme combinations A.4 and D.1 are combined. This target enzyme mixture comprises only 10 different enzyme activities, does not require ADP/ATP as cofactor and, consequently, does not lead to a net ATP production.

In another particularly preferred embodiment of the invention, enzyme combinations A.3 and D.1 are combined. This target enzyme mixture comprises 14 different enzyme activities, does not require ADP/ATP as cofactor and, consequently, does not lead to a net ATP production.

In another preferred embodiment of the invention, enzyme combinations A.2 and D.1 are combined. This target enzyme mixture comprises 13 different enzyme activities, requires ADP/ATP as cofactors, but does not lead to a net ATP production.

Production of Ethanol

In another embodiment of the invention, the target chemical is ethanol. Ethanol is completely soluble in water at any ratio and does not allow easy purification by formation of a separate organic phase. The inventive process for the cell-free production nevertheless provides a cost-efficient way to produce ethanol from renewable carbon sources.

In a particularly preferred embodiment, ethanol is produced from glucose via the intermediate pyruvate. The production of ethanol from glucose can be arbitrarily subdivided in two steps:

(A) Conversion of one molecule glucose to two molecules pyruvate; and (E) Conversion of two molecules pyruvate to two molecules ethanol.

Step (A): Conversion of Glucose to Pyruvate

This step is equivalent to step (A) in the production of n-butanol (see above).

Step (E): Conversion of Pyruvate to Ethanol

In a preferred embodiment of the invention, the enzyme activities as listed in Table 8 are used for the conversion of pyruvate to ethanol.

TABLE 8

Enzyme combination E.1, comprising enzyme activities for the conversion from pyruvate to ethanol

| # | Enzyme | EC # | Substrate | Product |
|---|---|---|---|---|
| 1 | Pyruvate decarboxylase | 4.1.1.1 | Pyruvate | Acetaldehyde |
| 2 | Alcohol dehydrogenase | 1.1.1.1 | Acetaldehyde | Ethanol |

When all reactions as described above are combined (enzyme combinations A.1, A.2, A.3 or A.4; plus enzyme combination E.1) a net conversion of one molecule glucose to two molecules $CO_2$ and two molecules ethanol is achieved. None of the enzyme combinations leads to a net production of reduction equivalents. Depending on the route from glucose to pyruvate none (A.2, A.3 or A.4) or up to 2 molecules of ATP (A.1) are generated from ADP and phosphate.

In a particularly preferred embodiment of the invention, enzyme combinations A.4 and E.1 are combined. This target enzyme mixture comprises only 7 different enzyme activities, does not require ADP/ATP as cofactor and, consequently, does not lead to a net ATP production.

In another particularly preferred embodiment of the invention, enzyme combinations A.3 and E.1 are combined. This target enzyme mixture comprises 11 different enzyme activities, does not require ADP/ATP as cofactor and does not lead to a net ATP production.

In another preferred embodiment of the invention, enzyme combinations A.2 and E.1 are combined. This target enzyme mixture comprises 10 different enzyme activities, requires ADP/ATP as cofactors, but does not lead to a net ATP production.

Production of 2-Butanol

In another embodiment of the invention the target chemical is 2-butanol.

In a particularly preferred embodiment, 2-butanol is produced from glucose via the intermediate pyruvate. The production of 2-butanol from glucose can be arbitrarily subdivided in two steps: (A) Conversion of one molecule glucose to two molecules pyruvate; and (F) Conversion of two molecules pyruvate to one molecule 2-butanol.

Step (A): Conversion of Glucose to Pyruvate

This step is equivalent to step (A) in the production of n-butanol (see above).

Step (F): Conversion of Pyruvate to 2-Butanol

In a preferred embodiment of the invention, the enzyme activities as listed in Table 9 are used in Step (F) for the cell free production of 2-butanol. In a preferred embodiment an alcohol dehydrogenase is used that uses acetoin as well as 2-butanone as substrate.

TABLE 9

Enzyme combination F.1, comprising enzyme activities for the conversion from pyruvate to 2-butanol

| # | Enzyme | EC # | Substrate | Product |
|---|---|---|---|---|
| 1 | Acetolactate synthase | 2.2.1.6 | Pyruvate | Acetolactate |
| 2 | Acetolactate decarboxylase | 4.1.1.5 | Acetolactate | Acetoin |
| 3 | Alcohol (Butanediol) dehydrogenase | 1.1.1.4 | Acetoin | Butane-2,3-diol |
| 4 | Diol dehydratase | 4.2.1.28 | Butane-2,3-diol | 2-butanone |
| 3 | Alcohol dehydrogenase | 1.1.1.1 | 2-butanone | 2-butanol |

When all reactions as described above are combined (enzyme combinations A.1, A.2, A.3 or A.4; plus enzyme combination F.1) a net conversion of one molecule glucose to two molecules $CO_2$, one molecule water and one molecule 2-butanol is achieved. None of the enzyme combinations leads to a net production of reduction equivalents (4 molecules $H_2$ are formed in the formation of two molecules pyruvate and are subsequently used up in the formation of 2-butanol). Depending on the route from glucose to pyruvate none (A.2, A.3 or A.4) or up to 2 molecules of ATP (A.1) are generated from ADP and phosphate.

In a particularly preferred embodiment of the invention, enzyme combinations A.4 and F.1 are combined. This target enzyme mixture comprises only 9 different enzymes, does not require ADP/ATP as cofactor and, consequently, does not lead to a net ATP production.

In another particularly preferred embodiment of the invention, enzyme combinations A.3 and F.1 are combined. This target enzyme mixture comprises 14 different enzyme activities, does not require ADP/ATP as cofactor and, consequently, does not lead to a net ATP production.

In another preferred embodiment of the invention, enzyme combinations A.2 and F.1 are combined. This target enzyme mixture comprises 13 different enzyme activities, requires ADP/ATP as cofactors, but does not lead to a net ATP production.

Other Substrates than Glucose

The described routes of the invention for the production of ethanol, n-butanol, isobutanol, 2-butanol or other chemicals are not limited to the use of glucose as substrate. Depending on the selectivity of the glucose dehydrogenase applied in the process e.g. also other C6-sugars can be used as substrate. In addition starch can be used as substrate in combination with an amylase/glucoamylase activity. Cellulosic material can be used as substrate together with an endocellulase/exocellulase/glucosidase activity. Also lactose, sucrose and other oligomeric or polymeric sugar derivatives can be used together with the corresponding enzymes that convert these to monomeric hexoses.

For one embodiment of the invention, lignocellulosic material is converted to ethanol using only 10 enzymes in total (enzymes combinations A.4 and E.1, endocellulase, exocellulase, beta-glucosidase).

EXAMPLES

The present invention is further defined in the following examples. It should be understood that these examples are given by way of illustration only and are not limiting the scope of the invention. From the above discussion and these examples, a person skilled in the art can ascertain the essential characteristics of this invention and without departing from the spirit and scope thereof, can make various changes and modifications of the invention to adapt it to various uses and conditions.

Example 1

Conversion of Glucose to n-Butanol Using Enzyme Mixtures from Cell Lysates of *C. saccharobutylicum*, *S. cerevisae* and *Z. mobilis*

*S. cerevisae* is grown anaerobically at 30° C. on YPD-medium containing 12% glucose. The formation of ethanol is monitored by sampling every hour and analysis by gas chromatography. In a phase of highest ethanol productivity the cells are harvested and suspended with 4× volume of reaction buffer (20 mM potassium phosphate, pH 6.5; 5 mM mercaptoethanol, 10 mM NaCl, 10 mM $MgSO_4$, 500 μM $ZnSO_4$, 500 μM $CoCl_2$, 200 μM $MnCl_2$). Cells are then lysed by disruption in a French press, the cell supernatant is clarified by centrifugation and filter sterilized to remove any remaining cells.

*Z. mobilis* (ATCC10998) is grown at 35° C. on LB medium containing 12% glucose. The formation of Ethanol is monitored by sampling every hour and analysis by gas chromatography. In a phase of highest ethanol productivity the cells are harvested and suspended with 4× volume of reaction buffer (20 mM potassium phosphate, pH 6.5; 5 mM mercaptoethanol, 10 mM NaCl, 10 mM $MgSO_4$, 500 μM $ZnSO_4$, 500 μM $CoCl_2$, 200 μM $MnCl_2$). Cells are then lysed by disruption in a French press and cell supernatant is clarified by centrifugation and filter sterilized to remove any remaining cells.

*Clostridium saccharobutylicum* DSMZ 13864 is grown on TYA medium (6 g/l Tryptone peptone, 2 g/l Yeast extract, 3 g/l $NH_4$—$CH_3COO$, 0.3 g/l $MgSO_4$, 0.5 g/l $KH_2PO_4$, 1 mg/l Resazurin, 10 mg/l $MnSO_4$, 1 mg/l p-aminobenzoic acid, 1 mg/l thiamine chloride hydrochloride, 0.2 mg/l biotin) with 6% glucose concentration at 35° C. The formation of butanol is followed by sampling every 2 h and analysis by GC. After 40 h the cells are in a solvent producing phase. The cells are harvested, lysed and the lysate is filter sterilized.

One milliliter of cell lysate from *C. saccharobutylicum* is incubated with 100 mM glucose with or without equal amount of the lysate from *S. cerevisae* or *Z. mobilis*. In all reactions 10 mM ketomalonic acid (71740, Fluka) are added, which acts as inhibitor of pyruvate decarboxylase. After 2 h anaerobic incubation at 30° C. the produced n-butanol is quantified in all reactions.

Example 2

Conversion of Glucose to n-Butanol Using Isolated Enzymes and Enzymes from Cell Lysates of *C. saccharobutylicum*

The cell lysate of *C. saccharobutylicum* from example 1 is incubated with the following enzymes: hexokinase (20 u/ml), phosphohexoisomerase (15 u/ml), phosphofructokinase (4 u/ml), aldolase (16 u/ml), phosphotrioseisomerase (300 u/ml), glycerinaldehyd-3-phosphat-dehydrogenase (60 u/ml), phosphoglycerate kinase (120 u/ml), phosphoglycerate mutase (60 u/ml), enolase (11 u/ml), pyruvate kinase (15 u/ml), pyruvate dehydrogenase (20 u/ml), phosphotransacetylase (15 u/ml) (all enzymes obtained from Sigma, see table below, only phosphoglycerate mutase obtained from USB, 26111 Miles Road, Cleveland Ohio, Product number 26118 100 UG, human enzyme recombinantly expressed in *E. coli*). Incubation is done in 20 mM potassium phosphate, pH 6.5; 5 mM mercaptoethanol, 10 mM NaCl, 10 mM $MgSO_4$, 500 μM $ZnSO_4$, 500 μM $CoCl_2$, 200 μM $MnCl_2$, 4 mM ATP, 1 mM ADP, 1 mM NADH, 1 mM NAD, 1 mM Coenzyme A and 200 mM glucose at 30° C. under anaerobic conditions. All reagents used are oxygen depleted by standard methods. After 10 min ATPase (0.5 u/ml) is added to avoid early built up of ATP. After 3 hours the produced n-butanol is quantified.

TABLE 10

Enzymes (Sigma-Aldrich) for the conversion of glucose to Acetyl CoA.

| Enzyme | Substrate | Product | EC# | Prod. # | Origin |
|---|---|---|---|---|---|
| Hexokinase | Glucose | Glucose-6-Phosphate | 2.7.1.1 | H6380 | S. cerevisiae |
| Phosphohexoisomerase | Glucose 6 Phosphate | Fructose-6-Phosphate | 5.3.1.9 | P5381 | S. cerevisiae |
| Phosphofructokinase | Fructose-6-Phosphat | Fructose-1,6-Bisphosphate | 2.7.1.11 | F0137 | B. stearothermophilus |
| Aldolase | Fructose-1,6-Bisphosphate | Glyceraldehyd-3-Phosphate, Dihydroxyacetonphosphate | 4.1.2.13 | A2714 | O. cuniculus (Rabbit) |
| Phosphotriose isomerase | Dihydroxyacetonphosphate | Glyceraldehyd-3-Phosphate | 5.3.1.1 | T2507 | S. cerevisiae |
| Glycerinaldehyd-3-phosphat-Dehydrogenase | Glyceraldehyd-3-Phosphate | Glycerate-1,3 Bisphosphate | 1.2.1.12 | G5537 | S. cerevisiae |
| Phosphoglycerate kinase | Glycerate-1,3 Bisphosphate | Glycerate-3-Phosphate | 2.7.2.3 | P7634 | S. cerevisiae |
| Enolase | Glycerate-2-Phosphate | Phosphoenolpyruvate | 4.2.1.11 | E6126 | S. cerevisiae |
| Pyruvate kinase | Phosphoenolpyruvat | Pyruvate | 2.7.1.40 | P1903 | B. stearothermophilus |
| Pyruvate dehydrogenase | Pyruvate | Acetylphosphate | 1.2.1.51 | P3798 | L. delbrueckii |
| Phosphotransacetylase | AcetylPhosphate | AcetylCoA | 1.2.1.51 | P2783 | B. stearothermophilus |
| ATP phosphohydrolase | ATP | ADP and phosphate | 3.6.1.3 | A7510 | S. scrofa (Pig) |

Example 3

Conversion of Glucose to n-Butanol Using Isolated Enzymes

The enzymes Thiolase (Seq. ID No. 1; EC 2.3.1.16, *Clostridium acetobutylicum*, NCBI-GenID NP_349476.1), 3-hydroxybutyryl-CoA dehydrogenase (Seq. ID No. 2; EC 1.1.1.157, NP_349314.1), Crotonase (Seq. ID No. 3; EC 4.2.1.55, *Clostridium acetobutylicum*, NP_349318.1), Butyryl-CoA dehydrogenase (Seq. ID No. 4; EC 1.3.99.2, *Clostridium acetobutylicum*, NCBI-GenID NP_349317.1), Coenzyme A acylating aldehyde dehydrogenase (Seq. ID No. 5; EC 1.2.1.57, *Clostridium beijerinckii*, NCBI-GenID AF132754_1), NADH-dependent butanol dehydrogenase B (BDH II) (Seq. ID No. 6; EC 1.1.1.-, *Clostridium acetobutylicum*, NCBI-GenID NP_349891.1) and an electron transfer flavoprotein (Seq. ID No. 8 and Seq. ID No. 7, respectively; etfA and B, *Clostridium acetobutylicum*, NCBI-GenID NP_349315.1 and NP_349316.1) are synthesized and recombinantly expressed in *E. coli* as described. All enzymes are combined (1 mg each) in a 5 ml reaction solution (20 mM potassium phosphate, pH 6.5; 5 mM mercaptoethanol, 10 mM NaCl, 10 mM MgSO$_4$, 500 µM ZnSO$_4$, 500 µM CoCl$_2$, 200 µM MnCl$_2$, 4 mM ATP, 1 mM ADP, 1 mM NADH, 1 mM NAD, 1 mM Coenzyme A). An equal volume of the enzyme mixture as listed in Tab. 9 above (conversion of glucose to acetyl CoA) is added: hexokinase (200 u/ml), phosphohexoisomerase (150 u/ml), phosphofructokinase (40 u/ml), aldolase (160 u/ml), phosphotrioseisomerase (3000 u/ml), glycerinaldehyde-3-phosphate-dehydrogenase (600 u/ml), phosphoglycerate kinase (1200 u/ml), phosphoglycerate mutase (600 u/ml), enolase (110 u/ml), pyruvate kinase (150 u/ml), pyruvate dehydrogenase (200 u/ml), phosphotransacetylase (150 u/ml), ATPase (4.5 u/ml) combined in 20 mM potassium phosphate buffer (pH 6.5) including 500 mM glucose. The reaction is stirred under anaerobic conditions at 30° C. After 3 hours the produced n-butanol is quantified.

Alternatively, the reaction is performed under continuous addition of glucose at a rate of 120 mg/h (manual addition of 60 mg in 30 minutes intervals, beginning 2 h after start of reaction). After total reaction time of 20 hrs the produced n-butanol is quantified.

Example 4

Conversion of Glucose to Isobutanol Using Isolated Enzymes and a Cell Lysate from *T. maritima*

*T. maritima* is grown at 80° C. on 5% glucose. Before complete utilisation of glucose the cells are harvested, resuspended in 4× volume of reaction buffer (20 mM potassium phosphate, pH 6.5; 5 mM mercaptoethanol, 10 mM NaCl, 10 mM MgSO$_4$, 500 µM ZnSO$_4$, 500 µM CoCl$_2$, 200 µM MnCl$_2$) and lysed by disruption in a French press. The cell supernatant is clarified by centrifugation and sterilized by filtration. The genes ilvICD for valine biosynthesis (acetolactate synthetase, Seq. ID No. 9, EC: 2.2.1.6, NCBI-GeneID: NP_228358.1; ketol-acid reductoisomerase, Seq. ID No. 10, EC. 1.1.1.86, NCBI-GeneID: NP_228360.1 and dihydroxy-acid dehydratase, Seq. ID No. 11, EC: 4.2.1.9, NCBI-GeneID: NP_228361.1) are cloned from *Thermotoga maritima* and recombinantly expressed in *E. coli* by standard methods. α-ketoisovalerate decarboxylase from *Lactococcus lactis* (Seq. ID No. 12, EC 4.1.1.-, NCBI-GeneID: CAG34226.1) is cloned and recombinantly expressed in *E. coli* by standard methods. Alcohol dehydrogenase (EC: 1.1.1.1) from *S. cerevisiae* is purchased from Sigma-Aldrich (A3263).

All enzymes are combined in 5 ml of reaction solution (20 mM potassium phosphate, pH 6.5; 5 mM mercaptoethanol, 10 mM NaCl, 10 mM MgSO$_4$, 500 µM ZnSO$_4$, 500 µM CoCl$_2$, 200 µM MnCl$_2$, 4 mM ATP, 1 mM ADP, 1 mM NADH, 1 mM NAD) at a concentration of 100 u/ml.

An equal volume of cell lysate from *T. maritima* is added and the combined sample is incubated at 50° C. with 250 mM glucose. After 1 h the produced isobutanol is quantified.

Example 5

Conversion of Glucose to Ethanol Using Isolated Enzymes

The genes for the enzymes: glucose dehydrogenase (Seq. ID No. 13, EC 1.1.1.47, *S. solfataricus*, NCBI Gen ID: NP_344316.1), gluconolactonase (Seq. ID No. 14, EC 3.1.1.17, *Picrophilus torridus*, NCBI Gen ID YP_023685.1), gluconate dehydratase (Seq. ID No. 15, EC 4.2.1.39, *Sulfolobus solfataricus*, NCBI-Gene ID: NP_344505, Mutation 19L), 2-keto-3-deoxy gluconate aldolase (Seq. ID No. 16, EC 4.1.2.14, *Sulfobus solfataricus*, NCBI Gen ID NP_344504.1), aldehyde dehydrogenase (Seq. ID No. 17, EC 1.2.1.3, *Flavobacterium frigidimaris*, NCBI Gen ID: BAB96577.1), glycerate kinase (Seq. ID No. 18, EC 2.7.1.-, *Sulfolobus solfataricus*, NCBI Gen ID: NP_342180.1), enolase (Seq. ID No. 19, EC 4.2.1.11, *Sulfolobus solfataricus*, NCBI Gen ID: NP_342405.1) and pyruvate kinase (Seq. ID No. 20, EC 2.7.1.40, *Sulfolobus solfataricus*, NCBI Gen ID: NP_342465.1) are synthesized and cloned into expression vector pET3b by standard methods using NdeI and BamHI for cloning. Cell growth, protein expression and partial purification is done as described by Lamble et al. (2003) but in addition supplying all buffers with 5 mM mercaptoethanol and using 80° C. as general temperature for heat precipitation (for the aldehyde dehydrogenase 60° C. is used). Protein production is usually between 5 and 50 mg/l. Pyruvate decarboxylase and aldehyde dehydrogenase from *S. cerevisiae* are obtained from Sigma-Aldrich (P#29163 and 82884).

All enzymes are combined (1 mg each of the recombinantly produced enzymes and 2 u of the purchased enzymes) in 5 ml of reaction solution (20 mM potassium phosphate, pH 6.5; 5 mM mercaptoethanol, 10 mM NaCl, 10 mM MgSO$_4$, 500 µM ZnSO$_4$, 500 µM CoCl$_2$, 200 µM MnCl$_2$, 4 mM ATP, 1 mM ADP, 1 mM NADH, 1 mM NAD) containing 250 mM glucose and incubated at 47° C. Every 30 min the two yeast enzymes are added to the solution to compensate for thermal inactivation. After 6 hrs the produced ethanol is quantified. Ethanol is produced from glucose using only 10 enzymes. In addition no net ATP is produced.

Example 6

Conversion of Glucose to Ethanol Using Isolated Enzymes

While it is of advantage to produce ethanol or chemicals and fuels from glucose without a net production of ATP or any other cofactor it is more beneficial when ATP or ADP as cofactor are eliminated entirely from the process. Therefore, the enzymes as described in example 5 but without the enzymes glycerate kinase (EC 2.7.1.-), enolase (EC 4.2.1.11) and pyruvate kinase (EC 2.7.1.40) are used. The conversion of glycerate to pyruvate is achieved using the enzymes glycerate dehydrogenase (alias hydroxypyruvate reductase (EC 1.1.1.29/1.1.1.81)), serine-pyruvate transaminase (EC 2.6.1.51), L-serine ammonia-lyase (EC 4.3.1.17) and alanine dehydrogenase (EC 1.4.1.1). The genes for the enzymes: glycerate dehydrogenase/hydroxypyruvate reductase (Seq. ID No. 21, EC 1.1.1.29/1.1.1.81, *Picrophilus torridus*, NCBI Gen ID: YP_023894.1), serine-pyruvate transaminase (Seq. ID No. 22, EC 2.6.1.51, *Sulfolobus solfataricus*, NCBI Gen ID: NP_343929.1), L-serine ammonia-lyase (Seq. ID No. 23 and Seq. ID No. 24, EC 4.3.1.17, *Thermus thermophilus*, YP_144295.1 and YP_144005.1) and alanine dehydrogenase (Seq. ID No. 25, EC 1.4.1.1, *Thermus thermophilus*, NCBI-Gen ID: YP_005739.1) are synthesized (codons optimized for production in *E. coli*) and cloned into expression vector pET3b using the NdeI and BamHI. Protein expression is done in *E. coli*.

All enzymes are combined (1 mg each of the recombinantly produced enzymes and 2 u of the purchased enzymes) in 5 ml of reaction solution (20 mM Potassium phosphate, 10 mM ammoniumsulfate, pH 6.5; 5 mM mercaptoethanol, 10 mM NaCl, 10 mM MgSO$_4$, 500 µM ZnSO$_4$, 500 µM CoCl$_2$, 200 µM MnCl$_2$, 1 mM NADH, 1 mM NAD, 1 mM serine, 1 mM alanine) containing 250 mM glucose and incubated at 47° C. Every 30 min the two yeast enzymes are added again to the solution to compensate for thermal inactivation. After 6 hrs incubation the produced ethanol is quantified. Ethanol is produced from glucose without involving phosphorylation and without requiring ATP or ADP as cofactor.

Example 7

Conversion of Glucose to Ethanol Using Isolated Enzymes

The formation of pyruvate from glycerate is a critical step in the production of ethanol or other derivatives of pyruvate. Dihydroxyacid dehydratase (EC 4.2.1.9) from *S. solfataricus* has been shown to accept different substrates (Kim and Lee, 2006). The gene for dihydroxyacid dehydratase (Seq. ID No. 26, EC 4.2.1.9, *S. solfataricus*, NP_344419.1) is expressed as described by Kim and Lee (2006). The enzyme is able to convert glycerate to pyruvate (though at lower activity in comparison to the natural substrate). The enzyme is also active towards gluconate (though at lower activity in comparison to natural substrate).

The enzymes glucose dehydrogenase, gluconolactonase, 2-keto-3-deoxy gluconate aldolase and aldehyde dehydrogenase from example 9 are combined with dihydroxyacid dehydratase (as described above) and pyruvate decarboxylase and aldehyde dehydrogenase from Sigma (see example 5) (1 mg each of the recombinantly produced enzymes and 2 u of the purchased enzymes) in 5 ml of reaction solution (20 mM potassium phosphate, 10 mM ammoniumsulfate, pH 6.5; 5 mM mercaptoethanol, 10 mM NaCl, 10 mM MgSO$_4$, 500 µM ZnSO$_4$, 500 µM CoCl$_2$, 200 µM MnCl$_2$ 1 mM NADH, 1 mM NAD) containing 250 mM glucose and incubated at 47° C. Every 30 min the two yeast enzymes are added again to the solution to compensate for thermal inactivation. After 6 hrs incubation the produced ethanol is quantified.

Example 8

Conversion of Glucose to n-Butanol Using Isolated Enzymes without Net Production of ATP The genes of the 4 units of pyruvate synthase (Seq. ID No. 27, Seq. ID No. 28, Seq. ID No. 29, Seq. ID No. 30, EC 1.2.7.1., *Sulfolobus solfataricus*, NCBI-GenID: NP_342664.1, NP_342663.1, NP_342666.1, NP_343517.1) and the gene of NADH ferrodoxin reductase (Seq. ID No. 31, EC 1.18.1.3, NCBI-GenID NP_342682.1) are synthesized and cloned in pET3b using NdeI and BamHI sites. The genes are anaerobically expressed in *E. coli* and partially purified as described. Glucose dehydrogenase, gluconolactonase, gluconate dehydratase, 2-keto-3-deoxy gluconate aldolase, aldehyde dehydrogenase, glycerate kinase, enolase and pyruvate kinase are obtained as described in example 5. Thiolase, β-hydroxybutyrylCoA dehydrogenase, butyrylCoA dehydrogenase, CoA acylating butanal dehydrogenase and butanol dehydrogenase with etfA and etfB are obtained as described in example 3.

All enzymes are combined (1 mg each) in 10 ml of reaction solution (20 mM potassium phosphate, pH 6.5; 5 mM mercaptoethanol, 10 mM NaCl, 10 mM MgSO$_4$, 500 µM ZnSO$_4$, 500 µM CoCl$_2$, 200 µM MnCl$_2$ 4 mM ATP, 1 mM ADP, 1 mM NADH, 1 mM NAD, 1 mM Coenzyme A, 1 mM FAD, 1 mM FADH$_2$) containing 250 mM glucose. The solution is incubated at 45° C. After 1 h the produced butanol is quantified.

Example 9

Conversion of Glucose to n-Butanol Using Isolated Enzymes without Net Production of ATP Glucose dehydrogenase, gluconolactonase, 2-keto-3-deoxy gluconate aldolase and aldehyde dehydrogenase are obtained as described in example 5. Dihydroxyacid dehydratase is obtained as described in example 9. NADH ferrodoxin reductase and pyruvate synthase are obtained as described in example 10. Thiolase, β-hydroxybutyrylCoA dehydrogenase, butyrylCoA dehydrogenase, CoA acylating butanal dehydrogenase and butanol dehydrogenase with etfA and etfB are obtained as described in example 3.

All enzymes are combined (1 mg each) in 10 ml of reaction solution (20 mM potassium phosphate, pH 6.5; 5 mM mercaptoethanol, 10 mM NaCl, 10 mM MgSO$_4$, 500 µM ZnSO$_4$, 500 µM CoCl$_2$, 200 µM MnCl$_2$ 1 mM NADH, 1 mM NAD, 1 mM Coenzyme A, 1 mM FAD, 1 mM FADH$_2$) containing 250 mM glucose. The solution is incubated at 45° C. After 1 h the produced n-butanol is quantified.

Example 10

Conversion of Glucose to Isobutanol Using Isolated Enzymes without Net Production of ATP The catalytic unit of acetolactate synthase (Seq. ID No. 32, EC 2.2.1.6, *Sulfolobus solfataricus*, NCBI-GenID: NP_342102.1), ketol-acid reductoisomerase (Seq. ID No. 33, EC 1.1.1.86, *Sulfolobus solfataricus*, NCBI-GenID: NP_342100.1), branched-chain-2-oxo acid decarboxylase (EC 4.1.1.72, *Lactococcus lactis*, NCBI-GenID:) and an alcohol dehydrogenase (Seq. ID No. 34, EC 1.1.1.1, *Flavobacterium frigidimaris*, NCBI-GenID: BAB91411.1) are cloned in pET3b using NdeI and BamHI sites. The genes are expressed in *E. coli*. Together with dihydroxyacid dehydratase (see example 7) these enzymes constitute the pathway from pyruvate to isobutanol. Glucose dehydrogenase, gluconolactonase, gluconate dehydratase, 2-keto-3-deoxy gluconate aldolase, aldehyde dehydrogenase, glycerate kinase, enolase and pyruvate kinase are obtained as described in example 5. Dihydroxyacid dehydratase is obtained as described in example 5.

All enzymes are combined (1 mg each) in 10 ml of reaction solution (20 mM potassium phosphate, pH 6.5; 5 mM mercaptoethanol, 10 mM NaCl, 10 mM MgSO$_4$, 500 µM ZnSO$_4$, 500 µM CoCl$_2$, 200 µM MnCl$_2$ 4 mM ATP, 1 mM ADP, 1 mM NADH, 1 mM NAD) containing 250 mM glucose. The solution is incubated at 53° C. for 1 h. Every 10 min fresh branched-chain-2-oxo acid decarboxylase is added to compensate for thermal inactivation. After 1 h the produced isobutanol is quantified.

REFERENCES

Algar, E. M. and Scopes, R. K. (1985) *Journal of Biotechnology* 2(5) 275-287.

Lamble, H. J.; Heyer, N. I.; Bull, S. D.; Hough, D. W. and Danson M. J. (2003) *J. Biol. Chem.* 36 (5) 34066-72.

Welch, P and Scopes R. K: (1985) *Journal of Biotechnology* 2(5) 257-273.

Zhang Y.-H. P., Evans B. R., Mielenz J. R., Hopkins R. C., Adams M. W. W. (2007) *PLoS ONE* 2(5): e456.

Zhang Y. H. P., Ye, X. And Wang, Y. (2008) Biotechnology: Research, Technology and Applications The following are exemplary and non-limiting sequences useful in various embodiments of the invention:

```
                                                          Seq. ID No. 1
Acetyl-CoA acetyltransferase (Thiolase) (2.3.1.16)
>gi|15896127|ref|NP_349476.1| acetyl-CoA acetyltransferase [Clostridium
acetobutylicum ATCC 824]
MKEVVIASAVRTAIGSYGKSLKDVPAVDLGATAIKEAVKKAGIKPEDVNEVILGNVLQAGLGQNPARQAS

FKAGLPVEIPAMTINKVCGSGLRTVSLAAQIIKAGDADVIIAGGMENMSRAPYLANNARWGYRMGNAKFV

DEMITDGLWDAFNDYHMGITAENIAERWNISREEQDEFALASQKKAEEAIKSGQFKDEIVPVVIKGRKGE

TVVDTDEHPRFGSTIEGLAELKPAFKKDGTVTAGNASGLNDCAAVLVIMSAEKAKELGVKPLAKIVSYGS

AGVDPAIMGYGPFYATKAAIEKAGWTVDELDLIESNEAFAAQSLAVAKDLKFDMNKVNVNGGAIALGHPI

GASGARILVTLVHAMQKRDAKKGLATLCIGGGQGTAILLEKC

Seq. ID No. 2
3-hydroxybutyryl-CoA dehydrogenase (1.1.1.157)
>gi|15895965|ref|NP_349314.1| 3-hydroxybutyryl-CoA dehydrogenase
[Clostridium acetobutylicum ATCC 824]
MKKVCVIGAGTMGSGIAQAFAAKGFEVVLRDIKDEFVDRGLDFINKNLSKLVKKGKIEEATKVEILTRIS

GTVDLNMAADCDLVIEAAVERMDIKKQIFADLDNICKPETILASNTSSLSITEVASATKRPDKVIGMHFF

NPAPVMKLVEVIRGIATSQETFDAVKETSIAIGKDPVEVAEAPGFVVNRILIPMINEAVGILAEGIASVE

DIDKAMKLGANHPMGPLELGDFIGLDICLAIMDVLYSETGDSKYRPHTLLKKYVRAGWLGRKSGKGFYDY

SK
```

```
                                                                   Seq. ID No. 3
3-hydroxybutyryl-CoA dehydratase (Crotonase) (4.2.1.55)
>gi|15895969|ref|NP_349318.1| 3-Hydroxybutyryl-CoA dehydratase
[Clostridium acetobutylicum ATCC 824]
MELNNVILEKEGKVAVVTINRPKALNALNSDTLKEMDYVIGEIENDSEVLAVILTGAGEKSFVAGADISE

MKEMNTIEGRKFGILGNKVFRRLELLEKPVIAAVNGFALGGGCEIAMSCDIRIASSNARFGQPEVGLGIT

PGFGGTQRLSRLVGMGMAKQLIFTAQNIKADEALRIGLVNKVVEPSELMNTAKEIANKIVSNAPVAVKLS

KQAINRGMQCDIDTALAFESEAFGECFSTEDQKDAMTAFIEKRKIEGFKNR

Seq. ID No. 4
butyryl-CoA dehydrogenase (1.3.99.2)
>gi|15895968|ref|NP_349317.1| butyryl-CoA dehydrogenase [Clostridium
acetobutylicum ATCC 824]
MDFNLTREQELVRQMVREFAENEVKPIAAEIDETERFPMENVKKMGQYGMMGIPFSKEYGGAGGDVLSYI

IAVEELSKVCGTTGVILSAHTSLCASLINEHGTEEQKQKYLVPLAKGEKIGAYGLTEPNAGTDSGAQQTV

AVLEGDHYVINGSKIFITNGGVADTFVIFAMTDRTKGTKGISAFIIEKGFKGFSIGKVEQKLGIRASSTT

ELVFEDMIVPVENMIGKEGKGFPIAMKTLDGGRIGIAAQALGIAEGAFNEARAYMKERKQFGRSLDKFQG

LAWMMADMDVAIESARYLVYKAAYLKQAGLPYTVDAARAKLHAANVAMDVTTKAVQLFGGYGYTKDYPVE

RMMRDAKITEIYEGTSEVQKLVISGKIFR

Seq. ID No. 5
coenzyme A acylating aldehyde dehydrogenase (1.2.1.57)
>gi|4884855|gb|AAD31841.1|AF132754_1 coenzyme A acylating aldehyde
dehydrogenase [Clostridium beijerinckii]
MNKDTLIPTTKDLKLKTNVENINLKNYKDNSSCFGVFENVENAINSAVHAQKILSLHYTKEQREKIITEI

RKAALENKEVLATMILEETHMGRYEDKILKHELVAKYTPGTEDLTTTAWSGDNGLTVVEMSPYGVIGAIT

PSTNPTETVICNSIGMIAAGNAVVFNGHPGAKKCVAFAIEMINKAIISCGGPENLVTTIKNPTMESLDAI

IKHPLIKLLCGTGGPGMVKTLLNSGKKAIGAGAGNPPVIVDDTADIEKAGKSIIEGCSFDNNLPCIAEKE

VFVFENVADDLISNMLKNNAVIINEDQVSKLIDLVLQKNNETQEYFINKKWVGKDAKLFSDEIDVESPSN

IKCIVCEVNANHPFVMTELMMPILPIVRVKDIDEAVKYTKIAEQNRKHSAYIYSKNIDNLNRFEREIDTT

IFVKNAKSPAGVGYEAEGFTTFTIAGSTGEGITSARNFTRQRRCVLAG

Seq. ID No. 6
NADH-dependent butanol dehydrogenase B (1.1.1.-)
>gi|15896542|ref|NP_349891.1| NADH-dependent butanol dehydrogenase B
(BDH II) [Clostridium acetobutylicum ATCC 824]
MVDFEYSIPTRIFFGKDKINVLGRELKKYGSKVLIVYGGGSIKRNGIYDKAVSILEKNSIKFYELIGVEP

NPRVTTVEKGVKICRENGVEVVLAIGGGSAIDCAKVIAAACEYDGNPWDIVLDGSKIKRVLPIASILTIA

ATGSEMDTWAVINNMDTNEKLIAAHPDMAPKFSILDPTYTYTVPTNQTAAGTADIMSHIFEVYFSNTKTA

YLQDRMAEALLRTCIKYGGIALEKPDDYEARANLMWASSLAINGLLTYGKDTNWSVHLMEHELSAYYDIT

HGVGLAILTPNWMEYILNNDTVYKFVEYGVNVWGIDKEKNHYDIAHQAIQKTRDYFVNVLGLPSRLRDVG

IEEEKLDIMAKESVKLTGGTIGNLRPVNASEVLQIFKKSV

Seq. ID No. 7
etfB
>gi|5895967|ref|NP_349316.1| electron transfer flavoprotein subunit beta
[Clostridium acetobutylicum ATCC 824]
MNIVVCLKQVPDTAEVRIDPVKGTLIREGVPSIINPDDKNALEEALVLKDNYGAHVTVISMGPPQAKNAL

VEALAMGADEAVLLTDRAFGGADTLATSHTIAAGIKKLKYDIVFAGRQAIDGDTAQVGPEIAEHLGIPQV

TYVEKVEVDGDTLKIRKAWEDGYEVVEVKTPVLLTAIKELNVPRYMSVEKIFGAFDKEVKMWTADDIDVD

KANLGLKGSPTKVKKSSTKEVKGQGEVIDKPVKEAAAYVVSKLKEEHYI

Seq. ID No. 8
etfA
>gi|15895966|ref|NP_349315.1| electron transfer flavoprotein subunit alpha
[Clostridium acetobutylicum ATCC 824]
MNKADYKGVWVFAEQRDGELQKVSLELLGKGKEMAEKLGVELTAVLLGHNTEKMSKDLLSHGADKVLAAD
```

-continued

NELLAHFSTDGYAKVICDLVNERKPEILFIGATFIGRDLGPRIAARLSTGLTADCTSLDIDVENRDLLAT

RPAFGGNLIATIVCSDHRPQMATVRPGVFEKLPVNDANVSDDKIEKVAIKLTASDIRTKVSKVVKLAKDI

ADIGEAKVLVAGGRGVGSKENFEKLEELASLLGGTIAASRAAIEKEWVDKDLQVGQTGKTVRPTLYIACG

ISGAIQHLAGMQDSDYIIAINKDVEAPIMKVADLAIVGDVNKVVPELIAQVKAANN

Seq. ID No. 9
Acetolactate synthase (2.2.1.6)
>gi|15643314|ref|NP_228358.1| acetolactate synthase, large subunit
[*Thermotoga maritima* MSB8]
MVHVKMKGSKMLFEALLKEGVDTIFGIPGGAIINVYDELCNYEDKINFYLFRHEQGATHAADGYARVTGK

PGVVIVTSGPGATNTVTGIATAYMDSIPIVVITGQVPTSFIGTDAFQEVDVTGITMPITKHNHLVTSIEE

LPYAIKEMFYVATTGRPGPVLLDFPKDIQTAEGEFNYPDTVEIPGYKPTVKGHPKQIKKAVELLKESKRP

VVIVGGGANLSGAMDLVNQFIDKFKVPAVSTLMGRGVNPSDEKLYYEGIGMHGTYYGNYAVANADLITAL

GVRFSDRILGNPRTFAKNARIVHVDIDPAEIGKNVRVDVPIVGDLKSVLEEFLKYEIETDFSDWIEELQE

IKKKYPLTYKRDGKLIKPQYVVEKVNEVFPDDTVVVADVGQNQMWVAQFYKFKHQRSFLCSGGLGTMGYA

LPAGIGAKIGAPDKEVVVFAGDGGFQMNIQELMTIKRYNLPVKIIVMDNKALGMVRQWQQLFFNCRYSAT

ILSDNPDFAKIAEAVGIKAMRIEKPDQVDEAIEKLAKSKEPMLIHAVVDPAENVLPMVPPGGDVGTPLIE

APYDETFVERVLKVIEESRRGDER

Seq. ID No. 10
Ketol-acid reductoisomerase (1.1.1.86)
>gi|156433161|ref|NF_228360.1| ketol-acid reductoisomerase [*Thermotoga maritima* MSB8]
MAVIYYDKDADLNLIKDKKIAIIGYGSQGHAHALNLKDSGLNVVVGLREGSKSWKKAEEQGLTVKTIEEA

AKEADIIMILIPDEHQPEIYKKYIEKHLTEGKMLMFAHGFNIHYHQIIPPKNVDVTMIAPKSPGHIVRRE

YVEGRGVPALVAVYQDYTGKAKDIALAYAKGIGVTRAGVIETTFKEETETDLFGEQAVLCGGVTALIKAG

FETLVDAGYQPEIAYFECLNELKLIVDLIYEGGLSFMRYSVSNTAEYGDYISQEKIVTKEVRENMKQMLK

DIQTGKFAKDWILENQAGRPYFYTMRKKESEHLIEKVGKELRKMMPWLKERNVDEE

Seq. ID No. 11
Dihydroxy-acid dehydratase (4.2.1.9)
>gi|15643317|ref|NP_228361.1| dihydroxy-acid dehydratase [*Thermotoga maritima* MSB8]
MRSDVIKKGLERVPHRSLLKALGITDDEMRRPFIGIVSSWNEIIPGHVHLDKVVEAVKAGVRMAGGVPFV

FPTIGICDGIAMDHRGMKFSLPSRELIADSIEIVASGFPFDGLVFVPNCDKITPGMMMAMGRLNIPSVLI

SGGPMLAGRYNGRDIDLITVFEAVGGYKVGKVDEETLKAIEDLACPGAGSCAGLFTANTMNSLAEALGIA

PRGNGTVPAVHAKRLRMAKEAGMLVVELVKRDVKPRDIVTLDSFMNAVMVDLATGGSTNTVLHLKAIAES

FGIDFDIKLFDELSRKIPHICNISPVGPYHIQDLDDAGGIYAVMKRLQENGLLKEDVMTIYLRKIGDLVR

EAKILNEDVIRPFDNPYHKEGGLGILFGNLAPEGAVAKLSGVPEKMMHHVGPAVVFEDGEEATKAILSGK

IKKGDVVVIRYEGPKGGPGMREMLSPTSAIVGMGLAEDVALITDGRFSGGSHGAVIGHVSPEAAEGGPIG

IVKDGDLIEIDFEKRTLNLLISDEEFERRMKEFTPLVKEVDSDYLRRYAFFVQSASKGAIFRKP

Seq. ID No. 12
Alpha-ketoisovalerate decarboxylase (4.1.1.72)
>gi|51870502|emb|CAG34226.1| alpha-ketoisovalerate decarboxylase
[*Lactococcus lactis* subsp. *lactis*]
MYTVGDYLLDRLHELGIEEIFGVPGDYNLQFLDQIISHKDMKWVGNANELNASYMADGYARTKKAAAFLT

TFGVGELSAVNGLAGSYAENLPVVEIVGSPTSKVQNEGKFVHHTLADGDFKHFMKMHEPVTAARTLLTAE

NATVEIDRVLSALLKERKPVYINLPVDVAAAKAEKPSLPLKKENSTSNTSDQEILNKIQESLKNAKKPIV

ITGHEIISFGLEKTVTQFISKTKLPITTLNFGKSSVDEALPSFLGIYNGTLSEPNLKEFVESADFILMLG

VKLTDSSTGAFTHHLNENKMISLNIDEGKIFNERIQNFDFESLISSLLDLSEIEYKGKYIDKKQEDFVPS

NALLSQDRLWQAVENLTQSNETIVAEQGTSFFGASSIFLKSKSHFIGQPLWGSIGYTFPAALGSQIADKE

```
SRHLLFIGDGSLQLTVQELGLAIREKINPICFIINNDGYTVEREIHGPNQSYNDIPMWNYSKLPESFGAT

EDRVVSKIVRTENEFVSVMKEAQADPNRMYWIELILAKEGAPKVLKKMGKLFAEQNKS
```

Seq. ID No. 13

```
Glucose dehydrogenase (EC 1.1.1.47)
>gi|15899711|ref|NP_344316,1| glucose 1-dehydrogenase (dhg-1) [Sulfolobus
solfataricus P2]
MKAIIVKPPNAGVQVKDVDEKKLDSYGKIKIRTIYNGICGTDREIVNGKLTLSTLPKGKDFLVLGHEAIG

VVEESYHGFSQGDLVMPVNRRGCGICRNCLVGRPDFCETGEFGEAGIRKMDGFMREWWYDDPKYLVKIPK

SIEDIGILAQPLADIEKSIEEILEVQKRVPVWTCDDGTLNCRKVLVVGTGPIGVLFTLLFRTYGLEVWMA

NRREPTEVEQTVIEETKTNYYNSSNGYDKLKDSVGKFDVIIDATGADVNILGNVIPLLGRNGVLGLFGFS

TSGSVPLDYKTLQEIVHTNKTIIGLVNGQPHFQQAVVHLASWKTLYPKAAKMLITKTVSINDEKELLKV

LREKEHGEIKIRILWE
```

Seq. ID No. 14

```
Gluconolactonase (EC 3.1.1.17)
>gi|48477979|ref|YP_022685.1| gluconolactonase [Picrophilus torridus DSM
9790]
MELNIEPQRLGESPIYIRELDTFLWVDILNGDIFSYNGNAKMEMHVNDMITSISPYKGTEVIASLRDGIA

IIDWKNKITNTLLKLDFPENIRFNDGRCDARGRFFIGTMDMNEKEPLGALYKFSGRKLERVLDNVTISNG

IAWSLDSRFMYYIDSPRKSVQVFDYDLSMGRITRHLYDIDLKNYSGVPDGMAIDINNNLWVAIHGSSLIS

VIDPAKNEILNEVKIAAKKVTSCTFGSVNMDKLFVTSAYDGTGGIPFIIDTGSRGVELNRYIP
```

Seq. ID No. 15

```
Gluconate dehydratase (EC 4.2.1.39)
>gi|15899900|ref|NP_344505.1| muconate cycloisomerase related protein
[Sulfolobus solfataricus P2]
MRIREIEPIVLTSKEKGSATWASIMIVTRVITENGEVGYGEAVPTLRVISVYNAIKQVSKAYIGKEVEEV

EKNYHEWYKQDFYLARSFESATAVSAIDIASWDIIGKELGAPIHKLLGGKTRDRVPVYANGWYQDCVTPE

EFAEKAKDVVKMGYKALKFDPFGPYYDWIDERGLREAEERVKAVREAVGDNVDILIEHHGRFNANSAIMI

AKRLEKYNPGFMEEPVHHEDVIGLRKYKASTHLRVALGERLISEKETAFYVEEGLVNILQPDLTNIGGVT

VGRSVIKIAEANDVEVAFHNAFGSIQNAVEIQLSAVTQNLYLLENFYDWFPQWKRDLVYNETPVEGCHVK

VPYKYGLGVSINEKTIEQLRAEPIPLDVIEEPVWVVKGTWKNYGV
```

Seq. ID No. 16

```
2-keto-3-deoxy gluconate aldolase (EC 4.1.2.14)
>gi|5899899|ref|NP_244504.1| 2-keto-3-deoxy gluconate aldolase (eda)
[Sulfolobus solfataricus P2]
MGRQGNLEELWCLRMPEIITPIITPFTKDNRIDKEKLKIHAENLIRKGIDKLFVNGTTGLGPSLSPEEKL

ENLKAVYDVTNKIIFQVGGLNLDDAIRLAKLSKDFDIVGIASYAPYYYPRMSEKHLVKYFKTLCEVSPHP

VYLYNYPTATGKDIDAKVAKEIGCFTGVKDTIENIIHTLDYKRLNPNMLVYSGSDMLIATVASTGLDGNV

AAGSNYLPEVTVTIKKLAMERKIDEALKLQFLHDEVIEASRIFGSLSSNYVLTKYFQGYDLGYPRPPIFP

LDDEEERQLIKKVEGIRAKLVELKILKE
```

Seq. ID No. 17

```
Aldehyde dehydrogenase (EC 1.2.1.3)
>gi|21238945|dbj|BAB96577.1| aldehyde dehydrogenase [Flavobacterium
frigidimaris]
MSNTIQRPEFKAKYDNYINGKFTAPVKGEYFDVLSPIDGKVFTKAAHSGKEDLELAVDAAYEAFKIWGKT

SVTERSILLNKIAQKIEDNLEYIATVETIDNGKPIRETLAADIPLAIDHFRYFAGVIRAEESSIAELDSQ

TVSIALSEPLGVVAQIIPWNFPILMAVWKIAPALAAGNTIVLKPAESTPISILVLMELIGDILPPGVLNI

VNGFGAELGRPLVTNKKVAKAAFTGSTTTGRLVMQYATENIIPVTLELGGKSPNIFFPSVADKDDDFFDK

AIEGAVLFALNQGEICTCPSRLLIHEDIYEKFIARVIERTEAIIAGNPLDKSTMIGAQTSLVQKEKIMSY

IKLGKEEGAELLTGGDENHLGGDLEGGYYIKPTLFKGHNKMRIFQEEIFGPVLAVTTFKTTEEAIEIAND
```

TMYGLGAGVWTRDAHEIYQVPRAIQSGRVWINQYHSYPAGAPFGGYKQSGIGRENHKMMLGQYRQTKNML

ISYDKKKLGFF

Seq. ID No. 18
Glycerate kinase (EC 2.7.1.-)
>gi|15897575|ref|NP_342180.1| glycerate kinase, putative [Sulfolobus
solfataricus P2]
MDIVDKILEYTDPYKALQEKVRVYNNILLFNNEKIPFKKPILISIGKASLPMARFFRERMELKAKLIVTP

KGTNGKENDVIEAGHPLPDENSIKAGKRMIELLANEDYDLVIFAISGGASALVEYSEIPLDELKIINKVL

VTSGLGINKINIVRKHLSKVKGGKILEYVKDKIPIVSFIVSDVPGNDISSIGSGLTSIDNSSNDDALEIL

KAIGLEKYSKYLTETPKSPSRIVKNYIILDNMEVLRKLANTLVNSFILTSEIRGEARDVGAIIASIYNSS

ESYNIPFRRPYYLLVGGEPEVTIQGKAGKGGRNGEVCLSFLKYAKKRNRFELLGFATDGIDGNSEYAGCK

VSSDMEIREDEINNALETHNSYGLLESHKAVIKTGYTHTNVNNIYVLRAP

Seq. ID No. 19
Enolase (EC 4.2.1.11)
>gi|15897800|ref|NP_342405.1| enolase [Sulfolobus solfataricus 52]
MINRFSIEKVKGLEIVDSRGNPTIRVFIRTSDGVESFGDAPAGASKGTREAVEVRDENGLTVKRAVDIVN

YIIDPALHGIDVREQGIIDKLLKDIDSTENKSKLGGNTIIATSIAALKTASKALGLEVFKYISGPRLPKI

PIPLLNIINGGLHAGNKLKIQEFIIVPIKFNTFKEALFAAIDVYRTLKGLITERYGKIYTAVGDEGGFSP

PLEDTREALDLIYTSINNAGYEGKIYMGMDAAGSDFYDSKKEKYIIDGRELDPNQLLEFYLDLVKQYPIV

YLEDPFEENSFDMFSQLQNKLSSTIITGDDLYTTNIKYLKIGIEKRSTKGVIVKPNQVGTISETFEFTNL

ARRNSMKLITSHRSGETEDNFIADFAVGIESDFIKVGAPARGERTSKYNKLLEIENKFGLEYEGKYFYL

Seq. ID No. 20
Pyruvate Kinase (EC 2.7.1.40)
>gi|15897860|ref|NP_342465.1| pyruvate kinase(pyK) [Sulfolobus
solfataricus P2]
MRKTKIVATLGPSSEEKVKELAEYVDVFRINFANGDETSHRKYFDLIRTYAPESSIIVDLPGPKLRLGEL

KEPIEVKKGDKIVFSQKDGIPVDDELFYSAVKENSDILIADGTIRVRVKSKAKDRVEGTVIEGGILLSRK

GINIPNVNLKSGITDNDLKLLKRALDLGADYIGLSFVISENDVKKVKEFVGDEAWVIAKIEKSEALKNLT

NIVNESDGIMVARGDLGVETGLENLPLIQRRIVRTSRVFGKPVILATQVLTSMINSPIPTRAEIIDISNS

IMQGVDSIMLSDETAIGNYPVESVRTLHNIISNVEKSVKHRPIGPLNSESDAIALAAVNASKVSKADVIV

VYSRSGNSILRVSRLRPERNIIGVSPDPRLAKKFKLCYGVIPISINKKMQSIDEIIDVSAKLMQEKIKDL

KFKKIVIVGGDPKQEAGKTNFVIVKTLEQQKK

Seq. ID No. 21
Glycerate dehydrogenase/Hydroxypyruvate reductase (EC 1.1.1.29 bzw. 1.1.1.81)
>gi|48478188|ref|Y5_023894.1| glycerate dehydrogenase [Picrophilus torridus
DSM 9790]
MKVSVQVNSYYNNEMSKKLLELCRDITGLDAVPGFDDDAEIILFSGRPVPGKKTKFMQSLSAGVNHLDFS

KIPDNIIIASNADAYSIPVAETAIGLMLAWARKICISNYNIHNNNYKRLDYKEYVSLYNKSLGILGYGGI

GRRTALIAKSFGMNIYAYSRSYKNDGISSYMEPEDIMKKSDFVLISLPLTKETANSINDKMLSLFRGLAI

INVGRAGVVDRNSMLNFLRNHNDKYYLTDVWWNEPIINENIPDNVIITPHSAGMSDNIYQPAVAAIENIK

NYINGKPKNIVKRSDYI

Seq. ID No. 22
Serine-pyruvate transaminase (EC 2.6.1.51)
>gi|15299324|ref|NP_343929.1| Serine-pyruvate aminotransferase (agxT)
[Sulfolobus solfataricus 52]
MDKLLLHVGPTTIKEDVLVAGLENNVGFTSKEFVEALAYSLKGLRYVMGASKNYQPLIIPGGGTSAMESV

TSLLKPNDKILVVSNGVFGDRWEQIFKRYPVNVKVLRPSPGDYVKPGEVEEEVRKSEYKLVALTHVETST

GVREPVKDVINKIRKYVELIVVDGVSSVGAEEVKAEEWNVDVYLTASQKALGSAAGLGLLLLSPKALSIL

DSQNSIAGYYLDLRNWLPVMRGAEEGKAAYFATPPVHVILQLAEAFRLIEKEGIENRIKRHTMVASAIRA

```
GLEALGLEIVARRPESYSNTVTGVILKVADPQKVLAGTVNEGVEFAPGVHPAFKYFRIGHMGWVTPNDAI

IAISVIERTLRKLGEPIRFGEGVKAVEEVLFSAR
```

Seq. ID No. 23
L-Serine ammonia-lyase (EC 4.3.1.17)
>gi|55980998|ref|YP_144295.1| L-serine dehydratase, alpha subunit [*Thermus thermophilus* HE2]

```
MPLTLNQLAELSGRASEHVLAEEVEETGTPAEEILARLRERLAVMRDSVRRGLASDAPSVAGLVGKNAKT

LWEAPDPLQDPLLKRVQAYAMAVNEENARMGRIVAAPTAGSAGTLPGALLGVADHLGIPDEELLMPLVLA

GGVAKMIGRVIHIAGASGGCQAEIGSSAAMAAAAVTELLGGTPEACAHAAALALQNTLGLVCDPVGGFVE

VPCVMRNGFYAVHAVSAASMALAGIRSVIPPDEVVLAMAGIGRLLPLELKETGLGGLADTPTGRRLAEEA

LKKT
```

Seq. ID No. 24
>gi|55980708|ref|YP_144005.1| L-serine dehydratase, beta subunit [*Thermus thermophilus* PBS]

```
MGLLDMIGPVMVGPSSSHTAGACRLALLARHLLGEKPKRVEFGLHGSFAKTGKGHGTHLALAAGVLGLTP

DDERLKESLSLAEREGVEVVFKEVELGDVHPNTVRMVLEGEKERLAVTGSSLGGGLVRVFDVDGFEVRIT

GSAPTLVIKNVDTPGVVARVARILADDEVNIAYLTVSRKKRGGEAMMSIEVDRPLSEVPLRYLEHLSYIL

WVRQIPPVMG
```

Seq. ID No. 25
Alanine dehydrogenase (EC 1.4.1.1)
>gi|46200072|ref|YP_005739.1| alanine dehydrogenase [*Thermus thermophilus* HB27]

```
MVIGVPREIKTLENRVALTPGGVESLVRRGHTVLVERGAGEGSGLSDAEYARAGAELVGREEAWGAEMVV

KVKEPLPEEYGFLREGLILFTYLHLAADRGLTEAMLRSGVTGIAYETVQLPDGTLPLLVPMSEVAGRMAP

QVGAQFLEKPKGGRGVLLGGVPGVAPASVVILGGGTVGTNAAKIALGMGAQVTILDVNHKRLQYLDDVFG

GRVVTLTATEANIKKSVQHADLLIGAVLVPGAKAPKLVTRDMLSLMKEGAVIVDVAVDQGGCVETIRPTT

HAEPTYVVDGVVHYGVANMPGAVPRTSTFALTNQTLPYVLKLAEKGLDALLEDAALLKGLNTHKGRLTHP

GVAEAFGLPYTPPEEALRG
```

Seq. ID No. 26
Dihydroxyacid dehydratase (EC 4.2.1.9)
>gi|15899814|ref|Np_344419.1| dihydroxy-acid dehydratase [*Sulfolobus solfataricus* P2]

```
MPAKLNSPSRYHGIYNAPHRAFLRSVGLTDEEIGKPLVAIATAWSEAGPCNFHTLALARVAKEGTKEAGL

SPLAFPTMVVNDNIGMGSEGMRYSLVSRDLIADMVEAQFNAHAFDGLVGIGGCDKTTPGILMAMARLNVP

SIYIYGGSAEPGYFMGKRLTIEDVHEAIGAYLAKRITENELYEIEKRAHPTLGTCSGLFTANTMGSMSEA

LGMALPGSASPTATSSRRVMYVKETGKALGSLIENGIKSREILTFEAFENAITTLMAMGGSTNAVLHLLA

IAYEAGVKLTLDDFNRISKRTPYIASMKPGGDYVMADLDEVGGVPVVLKKLLDAGLLHGDVLTVTGKTMK

QNLEQYKYPNVPHSHIVRDVKNPIKPRGGIVILKGSLAPEGAVIKVAATNVVKFEGKAKVYNSEDDAFKG

VQSGEVSEGEVVIIRYEGPKGAPGMPEMLRVTAAIMGAGLNNVALVTDGRFSGATRGPMVGHVAPEAMVG

GPIAIVEDGDTIVIDVESERLDLKLSEEEIKNRLKRWSPPSPRYKSGLLAKYASLVSQASMGAVTRPA
```

Seq. ID No. 27, Seq. ID No. 28, Seq. ID No. 29, Seq. ID No. 30
Pyruvate Synthase (1.2.7.1)
>gi|15898059|ref|NP_342664.1| pyruvate synthase alpha chain (Pyruvic-ferredoxin oxidoreductase alpha chain) (porA-1) [*Sulfolobus solfataricus* P2]

```
MQVLKRKVLALVGNHAVAYAVKQAKPKVLAVFPITPQTTMLEKLSEYISSEELKAELIKVESEHSALASI

YGAALAGARVFTATSSQGLLYMTEMIYWAGGQRVPIVAAVATRAIAEPWSIWDDHQDFVSKRDAIWIQIM

AENVQEAYDMTIQAFRISEDERVILPVMMGFDGFILTHTMERIEVLEDNEVDNFLPPRQFNLIDFSDPIA

IGPIATPEEYIKYRYEAMKAMERAKGVIEEIMGEYERISGRKQHGLVECYKCEDAKYVEVTMGAWSGDGK

AAVDRLRDSGVKTGLLKIRVFRPFPKEKVEEYLRSMKGVVVFDRAYSYGYGGILVNEIKAALYGYRVPVY
```

SVVAGIGGKDVRPRHFQKVIEDLINDNLEEERWLF

>gi|15898058|ref|NP_342663.1| 2-ketoisovalerate ferredoxin oxidoreductase subunit beta [*Sulfolobus solfataricus* P2]
MAVLSSQVTPKRMPKFYRGNAACPGCPIPKELDVALEVLGNKTVLVVPASCTTIIMGDTNGMPSTVPVVH

SAFGAAAAIGSGIVRSLRMRGDNDAIVAVWAGDGSTGDIGFAAVSGAAERNEDILYICYDNEAYMNTGIQ

RSGLTPKGAWTTTTPEGKREVKKPLPFIIAEHKVPYVATASIAYIYDYEAKMRKAKQIRGFRYIHLLSPC

PPGWRFDSKLTIDIAKLAVETGVWPLFEIENGEFKLTSVSKTLVEKKNRKPVAEYLKLQGRFKQLTEEQI

KGIQEEIDEMWEEIKRLIKK

>gi|5898061|ref|NP_342666.1| pyruvate synthase gamma chain (Pyruvic-ferredoxin oxidoreductase gamma chain) (porG-1) [*Sulfolobus solfataricus* P2]
MEYYNCDKMTLIELALRGRGGQGIVTAGELMTKAMVLEDKYAQSIPFFGGERRGAPVVSFVRLSDKPILL

HREVYNPDGVAIFDVSMIQLINVTEGLKENGFLLLNTNTPKRIWKNEYVVDATNIAKELGLIVAGWAIVN

TAMIGALARILGQPSLHSLEEAVKEEFPGKIGELNAEAVEIGYKEVKRVD

>gi|15898912|ref|NP_343517.1| pyruvate synthase delta chain (Pyruvic-ferredoxin oxidoreductase delta chain) (porD-like) [*Sulfolobus solfataricus* P2]
MGVKDEVKYVEIVYRGIFQKRLAKYIAEGIVYTAREMGRPALSFGRYGDSPERNGVPAKYYVGIGDGVNE

EDLIGYSTRVEPDLVDVIIVLDDTLLKGVESWAWQGVQPINLKLKSNGTMLVTSTKRINELLKMIPKKDF

NWTLGVIKTEPSFSGLWAFKDDLTMEKVWGGLAKLRPDIIDLDHLLKYVTKKQDANKRVSAVREAYSSVD

YRTVMKGEGIDFVYNPPRLLTWQEMLEGTVIPAVPRGKRNELFKRGTTKFERPTVDFDTCIKCKLCWVYC

PDECFDETPDGYYDIAYDYCVGCGICAEVCPVKDCIVMVDESMFIDYRRPYEMWKEDKAKYKEWLKTVRQ

ARKERVYVPGLGR

Seq. ID No. 31
NADH ferrodoxin reductase (1.18.1.3)
>gi|15898077|ref|NP_3426B2.1| toluene 1,2-dioxygenase system ferredoxin--NAD(+) reductase component, (todA) [*Sulfolobus solfataricus* P2]
MKCEYLIIGSGIAGYNALKELLQIKPNSRIIMITSDKYYPYDRPPLSKDYLKGKLEKDMLFFESDDFYKR

DNLEVMLNKSVERIDANLKEAILNDGSVISFDKALISTGGRPRRLNIPGSENALYLRSLDDADRIREAAS

KGKNALIIGAGFIGVEVASSLITLGVKTTVVEVMPYIWNTFVDEKVSRVIQQYLESKGINFILNESVKEI

QGKIATTSSGRKIEADMFLIAVGISPNVELAQRSGMQVDNGIVVNEYLETSARDIYAAGDIANIFDPREG

KRKRIEHWNNAEYTGKLAARNMAGSREAYNFISSIWSDIFDLHIESAGETRNYDEYIIRGKFELERPRFS

VIYLKGGIIKGYLAINRNVKEIIALNKLIQKQADVSSKRDKLADESFDLQKLLI

Seq. ID No. 32
Acetolactate Synthase (2.2.1.6) (large subunit)
>gi|15897497|ref|N5342102.1| acetolactate synthase catalytic subunit [*Sulfolobus solfataricus* P2]
MPTGARILVDSLKREGVKVVFGIPGLSNMQIYDAFVEDLANGELRHVLMRHEQAAAHAADGYARASGVPG

VCTATSGPGTTNLTTGLITAYWDSSPVIAITGNVPRSVMGKMAFQEADAMGVFENVTKYVIGIKRIDEIP

QWIKNAFYIATTGRPGPVVVDIPRDIFYEKMEEIKWPEKPLVKGYRDFPTRIDRLALKKAAEILINAERP

IILVGTGVVWANATPEVLELAELLHIPIVSTFPGKTAIPHDHPLYFGPMGYYGRAEASMAALESDAMLVV

GARFSDRTFTSYDEMVETRKKFIMVNIDPTDGEKAIKVDVGLYGNAKIILRELIKAIITLGQKRDKSAWI

KRVKEYKEYYSQFYYTEENGKLKPWKIMKTIRQSLPRDAIVTTGVGQHQMWAEVFWEVLEPRTFLTSSGM

GTMGFGLPAAMGAKLARPDKIVVDLDGDGSFLMTGTNLATAVDEHIPVISVIFDNRTLGLVRQVQDLFFG

RRIVGVDYGPSPDFVKLAEAFGALGFNATTYEEIEKSIKSAIKEDIPAVIRVPVDKEELALPTLPPGGRL

KQVILRDPRKSS

Seq. ID No. 33
Ketol-acid reductoisomerase (1.1.1.86)
>gi|15897495|ref|N5_342100.1| ketol-acid reductoisomerase [*Sulfolobus solfataricus* P2]
MKCTSKIYTDNDANLDLIKGKRIAVLGYGSQGRAWAQNLRDSGLNVVVGLEDLGKSWELAKSDGITPLHT

KDAVKDADIIIFLVPDMVQRTLWLESVQPYMKKGADLVFAHGFNIHYKLIDPPKDSDVYMIAPKGPGPTV

REYYKAGGGVPALVAVHQDVSGTALHKALAIAKGIGATRAGVIPTTFKEETETDLFGEQVILVGGIMELM

RAAFETLVEEGYQPEVAYFETINELKMLVDLVYEKGISGMLKAVSDTAKYGGMTVGKFVIDESVRKRMKE

ALQRIKSGKFAEEWVEEYGRGMPTVVNGLSNVQNSLEEKIGNQLRDLVQKGKPKS

Seq. ID No. 34
Alcohol Dehydrogenase (1.1.1.1)
>gi|20502556|dbj|BAB91411.1| alcohol dehydrogenase [*Flavobacterium frigidimaris*]
MLPKTMKAAVIREFGSLLKIEEVEVKRPGRNEILVKVIASGVCHTDLHAVEGDWPVKPKMPLIPGHEAVG

YVVAVGQEVKNVKEGDAVGVPWLYSACGGCDQCITGWETLCDTQQNGGYSVDGGFAEYVIADARYVGLLP

SNVNFMEMAPILCAGVTVYKGLKETEVKPGEWVAISGIGGLGHVAVQYAKAMGMHVAAIDVADDKLDLAK

KLGADLVVNAKNQNPGEFLKKEVGGMHGALITAVSPIAFKQGLETLRRKGTMALNGLPPGNFDLSIFDTV

LNRITIRGSIVGTRKDMKEAIEFAVEGKVKATVTPAKLENINEVFDKMKKGQIEGRVVLEIAKA

Seq. ID No. 35
Alpha-acetolactate decarboxylase (4.1.1.5)
>gi|113592|sp|523616.1|ALDC_BREBE RecName: Full = Alpha-acetolactate decarboxylase; Short = ALDC; Flags: Precursor
MKKNIITSITSLALVAGLSLTAFAATTATVPAPPAKQESKPAVAANPAPKNVLFQYSTINALMLGQFEGD

LTLKDLKLRGDMGLGTINDLDGEMIQMGTKFYQIDSTGKLSELPESVKTPFAVTTHFEPKEKTTLTNVQD

YNQLTKMLEEKFENKNVFYAVKLTGTFKMVKARTVPKQTRPYPQLTEVTKKQSEFEFKNVKGTLIGFYTP

NYAAALNVPGFHLHFITEDKTSGGHVLNLQFDNANLEISPIHEFDVQLPHTDDFAHSDLTQVTTSQVHQA

ESERK

Seq. ID No. 36
Alcohole dehydrogenase (1.1.1.1 bzw. 1.1.1.4)
>gi|18978332|ref|NP_579689.1| aldose reductase [*Pyrococcus furiosus* DSM 3638]
MKRVNAFNDLKRIGDDKVTAIGMGTWGIGGRETPDYSRDKESIEAIRYGLELGMNLIDTAEFYGAGHAEE

IVGEAIKEFEREDIFIVSKVWPTHFGYEEAKKAARASAKRLGTYIDLYLLHWPVDDFKKIEETLHALEDL

VDEGVIRYIGVSNFNLELLQRSQEVMRKYEIVANQVKYSVKDRWPETTGLLDYMKREGIALMAYTPLEKG

TLARNECLAKIGEKYGKTAAQVALNYLIWEENVVAIPKASNKEHLKENFGAMGWRLSEEDREMARRCV

Seq. ID No. 37, Seq ID No. 38, Seq ID No. 39
Diol dehydratase (4.2.1.28)
>gi|16334194|ref|YP_795721.1| propanediol dehydratase, small subunit [*Lactobacillus brevis* ATCC 357]
MSEIDDLVAKIVQQIGGTEAADQTTATPTSTATQTQHAALSKQDYPLYSKHPELVHSPSGKALNDITLDN

VLNDDIKANDLRITPDTLRMQGEVANDAGRDAVQRNFQRASELTSIPDDRLLEMYNALRPYRSTKAELLA

ISAELKDKYKAPVNAGWFAEAADYYESRKLKGDN

>gi|116334195|ref|YP_795722.1| diol dehydratase medium subunit [*Lactobacillus brevis* ATCC 367]
MAQEIDENLLRNIIRDVIAETQTGDTPISFKADAPAASSATTATAAPVNGDGPEPEKPVDWFKHVGVAKP

GYSRDEVVIAVAPAFAEVMDHNLTGISHKEILRQMVAGIEEEGLKARIVKVYRTSDVSFCGAEGDHLSGS

GIAIAIQSKGTTIIHQKDQEPLSNLELFPQAPVLDGDTYRAIGKNAAEYAKGMSPSPVPTVNDQMARVQY

QALSALMHIKETKQVVMGKPAEQIEVNFN

>gi|116334196|ref|YP_795723.1| propanediol dehydratase, large subunit [*Lactobacillus brevis* ATCC 367]
MKRQKRFEELEKRPIHLDGFVKEWPEEGFVAMMGPNDPKPSIKIENGKVTEMDSKPAADFDLIDLYIAKY

GIKLENAEKVMAMDSTKIANMLCDPNVPRKDIIEITTAMTPAKAEEVISKLNFAEMIMATQKMRPRRTPA

TQCHVTNIRDNPVQIAADAADAALRGFPEQETTTAVARYAPLNAISLMVGAQTGRPGVITQCSVEEAAEEL

SLGMRGFTGYAETISVYGTDKVFTDGDDTPWSKGFLASCYASRGLKMRFTSGSGSEVMMGYTEGKSMLYL

ESRCIFITKASGVQGLQNGGVSCIGIPGSVPSGIRSVLGENLLCMMLDLECASANQAAFSHSDMRRTERL

-continued

LGQFIAGTDYISSGYSSTPNYDNTFAGSNTDGLDYDDYYVMERDLAINGGIHPVDEQTIIKARNKAARAL

QGVFEDLGLPKITDEEVEAATYANTSKDMPERNMVEDMKAAQDLMDRGITGVDIVKALFNHGFKDVAQAV

LDLQKQKVCGDFLQTSAIFDSKWHVISAVNDANDYQGPGTGYRLEEDTEEWERIKNLPFAIDPQNMQL

---

The invention claimed is:

1. A process for the production of a target organic compound from a carbon source compound selected from glucose or a glucose-containing oligomer or polymer by a cell-free enzyme system, the process comprising (i) converting glucose to pyruvate, wherein no net production of ATP occurs;

wherein the enzyme system comprises the following enzyme activities, for the conversion from glucose to pyruvate:

glucose dehydrogenase (EC 1.1.1.47),
gluconate dehydratase (EC 4.2.1.39) and
2-keto-3-deoxy gluconate aldolase (EC 4.1.2.14) and
(ii) converting pyruvate to the target organic compound.

2. The process of claim 1, wherein the target organic compound is ethanol, n butanol, iso-butanol, or 2-butanol.

3. The process of claim 1 or 2, wherein the production process is performed in a liquid system comprising two separate phases, and the target organic compound is mainly present in or forms one of the separate phases, and
wherein the process further comprises collecting the target organic compound from the separate phase.

4. The process of claim 3, wherein an organic solvent is added to establish the two separate phases.

5. The process of claim 1, wherein the carbon source compound is continuously fed to the process and the target organic compound is continuously removed.

6. The process of claim 1, wherein the enzyme system comprises the following enzymes, for the conversion from glucose to pyruvate:
glucose dehydrogenase (EC 1.1.1.47),
gluconolactonase (EC 3.1.1.17),
gluconate dehydratase (EC 4.2.1.39),
2-keto-3-deoxy gluconate aldolase (EC 4.1.2.14),
aldehyde dehydrogenase (EC 1.2.1.3),
glycerate dehydrogenase (EC 1.1.1.29) or Hydroxypyruvate reductase (EC 1.1.1.81),
serine-pyruvate transaminase (EC 2.6.1.51),
L-serine ammonia-lyase (EC 4.3.1.17) and
alanine dehydrogenase (EC 1.4.1.1).

7. The process of claim 1, wherein the enzyme system comprises the following enzyme activities for the conversion from glucose to pyruvate:
glucose dehydrogenase (EC 1.1.1.47),
gluconolactonase (EC 3.1.1.17),
gluconate dehydratase (EC 4.2.1.39),
2-keto-3-deoxy gluconate aldolase (EC 4.1.2.14),
aldehyde dehydrogenase (EC 1.2.1.3) and
glycerate dehydratase (EC 4.2.1).

8. The process of claim 1, wherein ethanol is produced from glucose by an enzyme system comprising from 6 to 11 enzymes.

9. The process of claim 1, wherein n-butanol is produced from glucose by an enzyme system comprising from 6 to 17 enzymes.

10. The process of claim 1, wherein iso-butanol is produced by an enzyme system comprising from 6 to 14 enzymes.

11. The process of claim 1, wherein 2-butanol is produced by an enzyme system comprising from 6 to 13 enzymes.

12. The process of claim 1, wherein the conversion of glucose to pyruvate works completely without ATP and/or ADP as cofactors.

13. The process of claim 1, wherein the enzyme system further comprises the following enzyme activities, for the conversion from glucose to pyruvate:
aldehyde dehydrogenase (EC 1.2.1.3)
phosphoglycerate kinase (EC 2.7.1),
enolase (EC 4.2.1.11),
pyruvate kinase (EC 2.7.1.40).

14. The process of claim 1, wherein the enzyme system further comprises the following enzyme activities, for the conversion from glucose to pyruvate:
aldehyde dehydrogenase (EC 1.2.1.3),
glycerate dehydrogenase (EC 1.1.1.29)
serine-pyruvate transaminase (EC 2.6.1.51),
L-serine ammonia-lyase (EC 4.3.1.17) and
alanine dehydrogenase (EC 1.4.1.1).

15. The process of claim 1, wherein the enzyme system further comprises the following enzyme activities, for the conversion from glucose to pyruvate:
aldehyde dehydrogenase (EC 1.2.1.3),
dihydroxyacid dehydratase (EC 4.2.1.9).

* * * * *